United States Patent [19]

Hogan et al.

[11] Patent Number: 5,424,413
[45] Date of Patent: Jun. 13, 1995

[54] BRANCHED NUCLEIC ACID PROBES

[75] Inventors: James J. Hogan, Coronado; Lyle J. Arnold, Jr.; Norman C. Nelson, both of San Diego; Robert Bezverkov, Cardiff by the Sea, all of Calif.

[73] Assignee: Gen-Probe Incorporated, San Diego, Calif.

[21] Appl. No.: 940,652

[22] Filed: Sep. 4, 1992

Related U.S. Application Data

[62] Division of Ser. No. 827,021, Jan. 22, 1992, abandoned.

[51] Int. Cl.[6] ............................................. C07H 21/04
[52] U.S. Cl. .............................. 536/24.31; 536/24.3; 536/24.32; 435/6
[58] Field of Search .................. 536/24.3, 24.31, 24.32; 435/6

[56] References Cited

U.S. PATENT DOCUMENTS

| | | | |
|---|---|---|---|
| 4,775,619 | 10/1988 | Urdea | 435/6 |
| 4,820,630 | 4/1989 | Taub | 435/5 |
| 5,118,801 | 6/1992 | Lizardi et al. | 536/27 |

FOREIGN PATENT DOCUMENTS

| | | |
|---|---|---|
| 8500813 | 2/1985 | WIPO . |
| 8704165 | 7/1987 | WIPO . |
| 8909284 | 10/1989 | WIPO . |

OTHER PUBLICATIONS

Sambrook et al., *Molecular Cloning*, Cold Spring Harbor Laboratory Press, 1989.
Arnold et al., Clin. Chem. 35(8), 1588–1594 (1989).
Zon, Pharmac. Res. 5(9), 539–549 (1988).
Beal et al., Science 251, 1360–1363 (1991).
Matthews et al., Analyt. Biochem. 169, 1–25 (1988).
Meinkoth et al., Analyt. Biochem. 138, 267–284 (1984).
Mueller et al., Proc. Natl. Acad. Sci, USA, 85:9441, 1988.
Murchie et al., Nucleic Acids Research 18(9):2599, 1990.
Evans and Kolodner, J. Biological Chemistry, 262(19):9160, 1987.
West et al., J. Biological Chemistry, 262(26):12752, 1987.
Bianchi, EMBO Journal, 7(3):843, 1988.
Lu et al., J. Biological Chemistry, 264(35):20851, 1989.
Taylor and Smith, J. Mol. Biol. 211:117, 1990.
Guo et al., Biochemistry, 28(6):2355, 1989.
Guo et al., Biochemistry, 29:570, 1990.
Lu et al., Biochemistry, 29:1614, 1990.
Jensch and Kemper, EMBO Journal, 5(1):181, 1986.
Parsons et al., EMBO Journal, 8(1):239, 1989.
Parsons and West, Cell, 52:621, 1988.
Evans and Kolodner, J. Biological Chemistry, 201:69, 1987.
Murchie et al., Nature, 341:763, 1989.
Seeman et al., Electrophoresis, 10:345, 1989.
Cooper and Hagerman, J. Mol. Biol, 198:711, 1987.
Cooper and Hagerman, Proc. Natl. Acad. Sci. USA, 86:7336, 1989.
Bell and Byers, Analytical Biochemistry 103:527, 1983.
Seeman & Kallenbach, Biophysical Journal 44:201, 1983.

(List continued on next page.)

Primary Examiner—Margaret Parr
Assistant Examiner—Kenneth R. Horlick
Attorney, Agent, or Firm—Lyon & Lyon

[57] ABSTRACT

Nucleic acid hybridization probes having at least one nucleic acid strand which has at least two separate target specific regions that hybridize to a target nucleic acid sequence, and at least two distinct arm regions that do not hybridize with the target nucleic acid but possess complementary regions that are capable of hybridizing with one another. These regions are designed such that, under appropriate hybridization conditions, the complementary arm regions will not hybridize to one another in the absence of the target nucleic acid; but, in the presence of target nucleic acid the target-specific regions of the probe will anneal to the target nucleic acid, and the complementary arm regions will anneal to one another, thereby forming a branched nucleic acid structure.

37 Claims, 51 Drawing Sheets

OTHER PUBLICATIONS

Petrillo et al., Biopolymers 27:1337, 1988.
Marky et al., Biopolymers, 26:1621, 1987.
Chen et al., J. Am. Chem. Soc. 111:6402, 1989.
Kallenbach et al., Nature, 305:829, 1983.
Wemmer et al., Biochemistry 24:5745, 1985.
Duckett et al., EMBO Journal, 9(2):583, 1990.
Seeman et al., Molecular Basis of Cancer, Part A: Macromolecular Structure, Carcinogens, and Oncogenes, pp. 99–108, 1985.
Kallenbach et al., Journal of Biomolecular Structure and Dynamics, ISSN 0739–1102, vol. 1, 1983, pp. 159–168.
Chen et al., Monomobile DNA Junctions, 27(16):6032, 1988.
Ma et al., Nucleic Acids Research 14(24):9745, 1986.
Seeman, Journal of Biomolecular Structure & Dynamics, ISSN 0735–1102 vol. 5, No. 5, 1988, pp. 997–1004.
Smithies, Science 169:882, 1970.
Sigal and Alberts, J. Mol. Biol. 71:789, 1972.
Sobell, Proc. Natl. Acad. Sci. USA, 69(9):2483, 1972.
von Kitzing et al., Nucleic Acids Research 18(9):2671, 1990.
Seeman, Journal of Biomolecular Structure and Dynamics, ISSN 0739–1102 vol. 3, No. 1, 1985, pp. 11–34.
Bell and Byers, Proc. Natl. Acad. Sci. USA, 76(7):3445, 1979.
Hsu and Landy, Nature, 311:721, 1984.
Churchill et al., Proc. Natl. Acad. Sci. USA 85:4653, 1988.
Duckett et al., Cell, 55:79, 1988.
Gough et al., EMBO Journal 5(1):191, 1986.
Furlong and Lilley, Nucleic Acids Research, 14:3995, 1986.
Gough and Lilley, Nature 313:154, 1985.
Diekmann and Lilley, Nucleic Acids Research, 15(14):5765, 1987.
Frappier et al., J. Mol. Biol. 193:751, 1987.
Mifflin, 35 Clin. Chem. 1819, 1989.
Bloomfield et al., (1974) *Physical Chemistry of Nucleic Acids,* Harper and Row, N.Y.

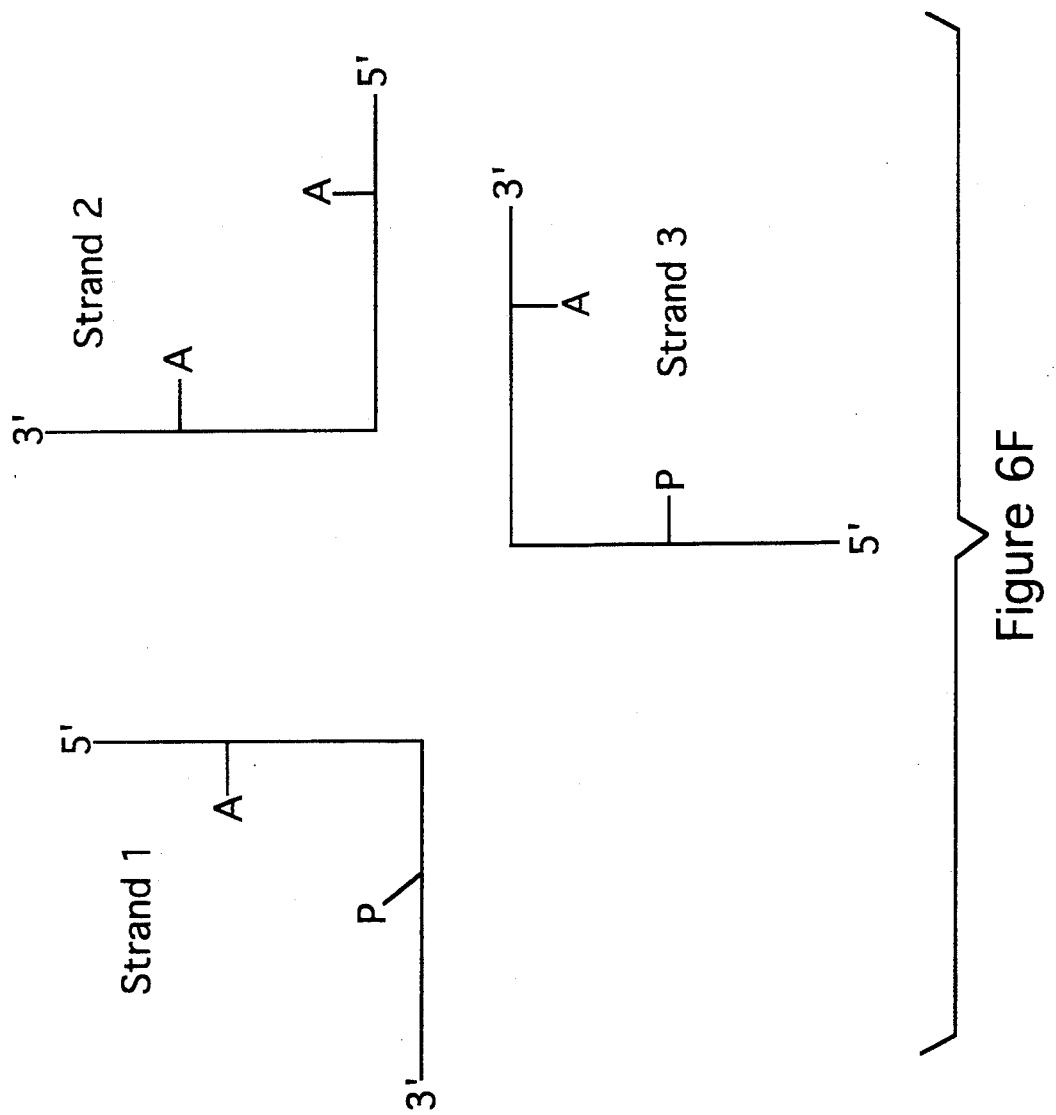

| | | Half-Life (min) | | | |
|---|---|---|---|---|---|
| | | Hybrid | Control | DH Ratio | Tm (°C) |
| 1. |  | 18.19 | 0.53 | 34.3 | 66.5 |
| 2. |  | 6.10 | 0.70 | 8.7 | 66.3 |
| 3. |  | 22.32 | 0.55 | 40.6 | 66.1 |
| 4. |  | 9.41 | 0.56 | 16.8 | 68.8 |
| 5. |  | 7.67 | 0.72 | 10.7 | 67.8 |
| 6. |  | 8.75 | 0.73 | 12.0 | — |
| 7. |  | 10.02 | 0.56 | 17.9 | 67.9 |
| 8. |  | 8.44 | 0.72 | 11.37 | 69.3 |
| 9. |  | 8.83 | 0.75 | 11.8 | 64.5 |
| 10. |  | 3.31 | 0.56 | 5.9 | 58.4 |
| 11. |  | 3.97 | 0.63 | 6.3 | 58.4 |
| 12. |  | 5.42 | 0.57 | 9.5 | 58.7 |
| 13. |  | 7.37 | 0.62 | 11.9 | — |
| 14. |  | 6.76 | 0.60 | 11.3 | — |
| 15. |  | 7.51 | 0.58 | 12.9 | 62.2 |
| 16. |  | 5.79 | 0.73 | 7.9 | 62.0 |
| 17. |  | 5.21 | 0.62 | 8.4 | 61.6 |
| 18. |  | 6.36 | 0.64 | 9.9 | 61.4 |

Samples 10-12 are bracketed as N. men.

↑ = Site of attachment. For samples 10-12, target = *N. men.*; for all other samples, target = *N. gon.* Amounts for all samples: target strand = 0.6 pmol; AE-labeled strand(s) = 0.1 pmol; unlabeled probe strands = 2 pmol.

Figure 12C

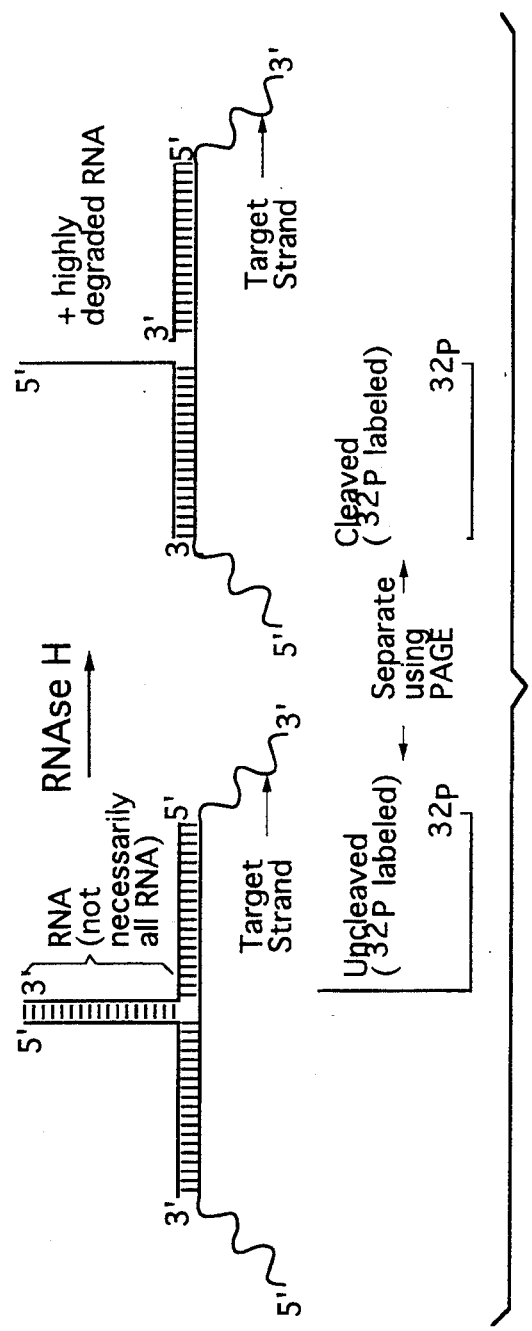
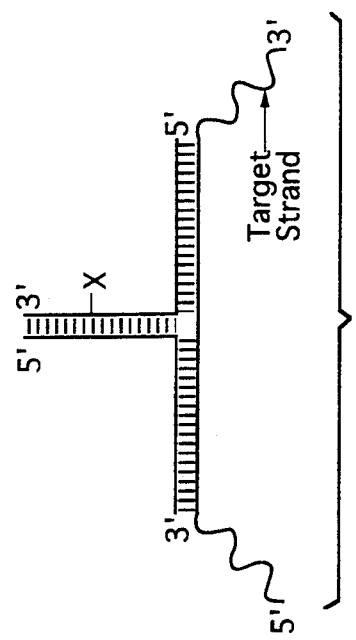
Figure 15E
Figure 15F

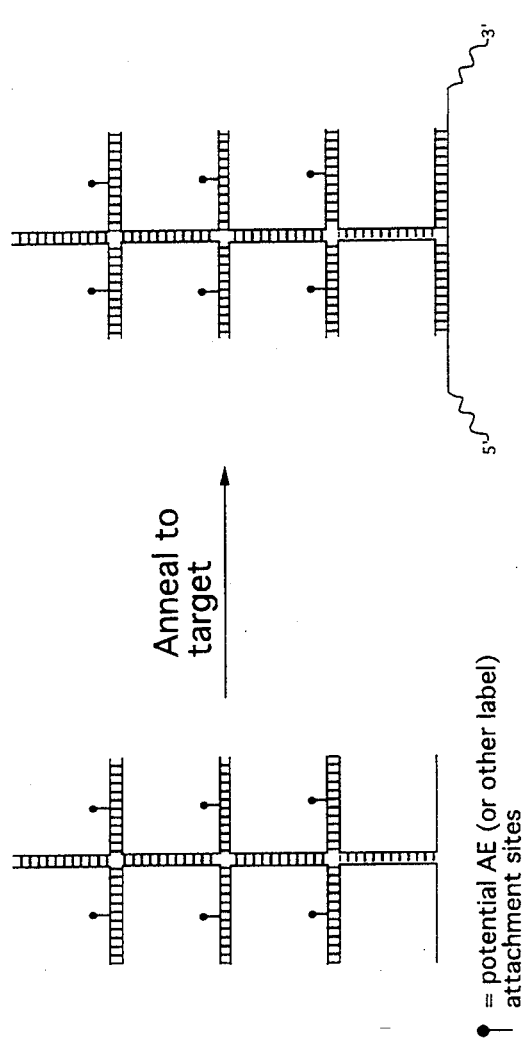
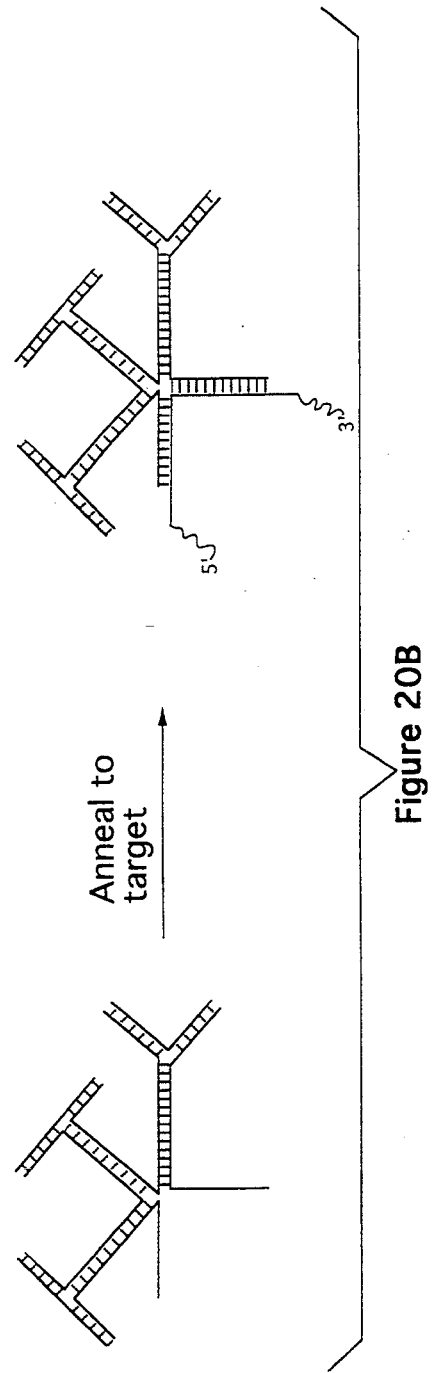
● = potential AE (or other label) attachment sites
Figure 20A
Figure 20B

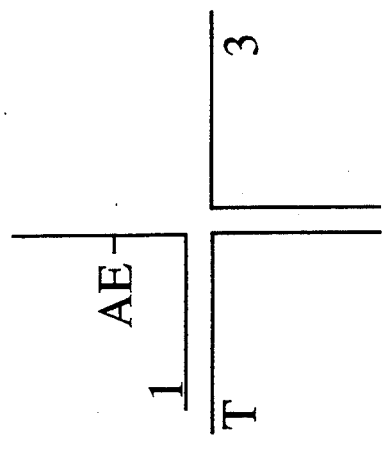
Figure 22C
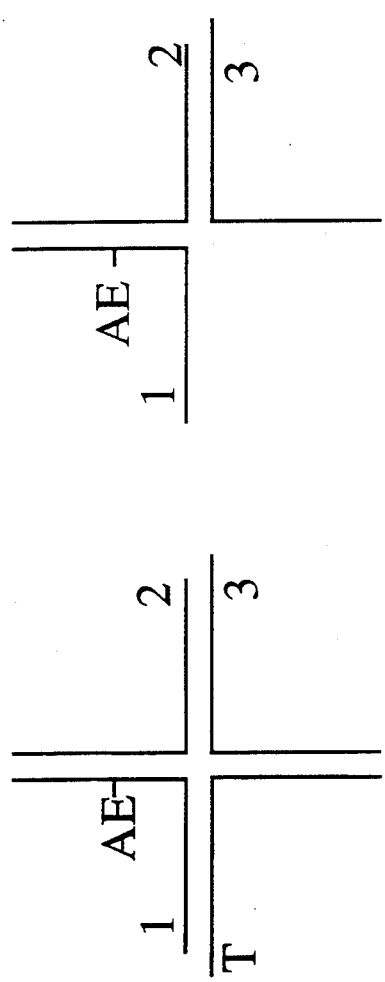
Figure 22A
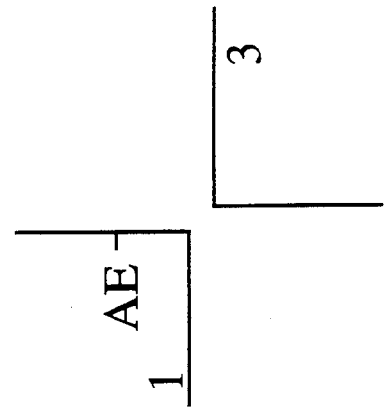
Figure 22F
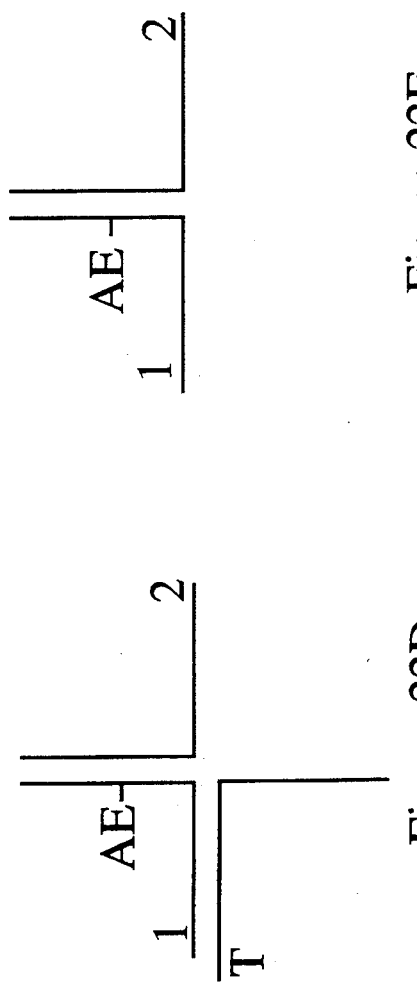
Figure 22B
Figure 22E
Figure 22D

SEQUENCE LISTING ( 1 ) GENERAL INFORMATION:

( i i i ) NUMBER OF SEQUENCES: 31

( 2 ) INFORMATION FOR SEQ ID NO: 1:

( i ) SEQUENCE CHARACTERISTICS:
        ( A ) LENGTH:32
        ( B ) TYPE:nucleic acid
        ( C ) STRANDEDNESS:single
        ( D ) TOPOLOGY:linear ( i i ) SEQUENCE DESCRIPTION: SEQ ID NO: 1:

```
ATCTTGGTTA CCTGGTCATA TCCTCCCACA AC                32
```

( 2 ) INFORMATION FOR SEQ ID NO: 2:

( i ) SEQUENCE CHARACTERISTICS:
        ( A ) LENGTH:31
        ( B ) TYPE:nucleic acid
        ( C ) STRANDEDNESS:single
        ( D ) TOPOLOGY:linear ( i i ) SEQUENCE DESCRIPTION: SEQ ID NO: 2:

```
CGGGTAGCGC TGAGAACCAG GTAACCAAGA T                 31
```

( 2 ) INFORMATION FOR SEQ ID NO: 3:

( i ) SEQUENCE CHARACTERISTICS:
        ( A ) LENGTH:20
        ( B ) TYPE:nucleic acid
        ( C ) STRANDEDNESS:single
        ( D ) TOPOLOGY:linear ( i i ) SEQUENCE DESCRIPTION: SEQ ID NO: 3:

CGGGTAGCGC TGAGAACCAG                    20

( 2 ) INFORMATION FOR SEQ ID NO: 4:

( i ) SEQUENCE CHARACTERISTICS:
        ( A ) LENGTH:33
        ( B ) TYPE:nucleic acid
        ( C ) STRANDEDNESS:single
        ( D ) TOPOLOGY:linear ( i i ) SEQUENCE DESCRIPTION: SEQ ID NO: 4:

GTTCCGATAT GTGCCGATAT GTTACTCACC CGT          33

( 2 ) INFORMATION FOR SEQ ID NO: 5:

( i ) SEQUENCE CHARACTERISTICS:
        ( A ) LENGTH:26
        ( B ) TYPE:nucleic acid
        ( C ) STRANDEDNESS:single
        ( D ) TOPOLOGY:linear ( i i ) SEQUENCE DESCRIPTION: SEQ ID NO: 5:

GGCCTGCATA ATCCGCTACC CGGTAC              26

( 2 ) INFORMATION FOR SEQ ID NO: 6:

( i ) SEQUENCE CHARACTERISTICS:
        ( A ) LENGTH:46
        ( B ) TYPE:nucleic acid
        ( C ) STRANDEDNESS:single
        ( D ) TOPOLOGY:linear ( i i ) SEQUENCE DESCRIPTION: SEQ ID NO: 6:

GGCCTGCAGA ATCGTTCCGA TATGTTCCGA TATGTTACTC ACCCGT    46

( 2 ) INFORMATION FOR SEQ ID NO: 7:

( i ) SEQUENCE CHARACTERISTICS:
        ( A ) LENGTH:22
        ( B ) TYPE:nucleic acid
        ( C ) STRANDEDNESS:single
        ( D ) TOPOLOGY:linear ( i i ) SEQUENCE DESCRIPTION: SEQ ID NO: 7:

CCGCTACCCG GTTCTGCAGG CC                  22

( 2 ) INFORMATION FOR SEQ ID NO: 8:

( i ) SEQUENCE CHARACTERISTICS:
        ( A ) LENGTH:63
        ( B ) TYPE:nucleic acid
        ( C ) STRANDEDNESS:single
        ( D ) TOPOLOGY:linear ( i i ) SEQUENCE DESCRIPTION: SEQ ID NO: 8:

GGGTAGCGCT GAGAATACCA GGTGACTCCC TCAATCTAAC CTGGTATCAT    50

ATCCTCCCAC AAC                                        63

( 2 ) INFORMATION FOR SEQ ID NO: 9:

( i ) SEQUENCE CHARACTERISTICS:
        ( A ) LENGTH:43
        ( B ) TYPE:nucleic acid
        ( C ) STRANDEDNESS:single
        ( D ) TOPOLOGY:linear ( i i ) SEQUENCE DESCRIPTION: SEQ ID NO: 9:

TGCGGGGTTG TGGGAGGATA TGTCTCAGCG CTACCCGGCT GAG    43

( 2 ) INFORMATION FOR SEQ ID NO: 10:

( i ) SEQUENCE CHARACTERISTICS:
        ( A ) LENGTH:17
        ( B ) TYPE:nucleic acid
        ( C ) STRANDEDNESS:single
        ( D ) TOPOLOGY:linear ( i i ) SEQUENCE DESCRIPTION: SEQ ID NO: 10:

CGGCTGCTTA ATACGTT    17

( 2 ) INFORMATION FOR SEQ ID NO: 11:

( i ) SEQUENCE CHARACTERISTICS:
        ( A ) LENGTH:33
        ( B ) TYPE:nucleic acid
        ( C ) STRANDEDNESS:single
        ( D ) TOPOLOGY:linear ( i i ) SEQUENCE DESCRIPTION: SEQ ID NO: 11:

GCGCACTCAT TCCGCTACCC GGTTAAGCAG CCG    33

( 2 ) INFORMATION FOR SEQ ID NO: 12:

( i ) SEQUENCE CHARACTERISTICS:
        ( A ) LENGTH:19
        ( B ) TYPE:nucleic acid
        ( C ) STRANDEDNESS:single
        ( D ) TOPOLOGY:linear ( i i ) SEQUENCE DESCRIPTION: SEQ ID NO: 12:

GTTATCCCAA TGACTGCGC    19

( 2 ) INFORMATION FOR SEQ ID NO: 13:

( i ) SEQUENCE CHARACTERISTICS:
        ( A ) LENGTH:66
        ( B ) TYPE:nucleic acid
        ( C ) STRANDEDNESS:single
        ( D ) TOPOLOGY:linear ( i i ) SEQUENCE DESCRIPTION: SEQ ID NO: 13:

GGCTAACCAC CTCTATCGCA GAACTTCGGT GACGTATTGA ACTCTGCTTA    50

AATCCAGTGG CTGAGT    66

( 2 ) INFORMATION FOR SEQ ID NO: 14:

( i ) SEQUENCE CHARACTERISTICS:
        ( A ) LENGTH:56
        ( B ) TYPE:nucleic acid
        ( C ) STRANDEDNESS:single
        ( D ) TOPOLOGY:linear ( i i ) SEQUENCE DESCRIPTION: SEQ ID NO: 14:

AGTCAGATGC TACTGGCCGC TGAAGGGCTT TACGTCACCG ATACATCTAA    50

CCTCCG    56

( 2 ) INFORMATION FOR SEQ ID NO: 15:

( i ) SEQUENCE CHARACTERISTICS:
        ( A ) LENGTH:31
        ( B ) TYPE:nucleic acid
        ( C ) STRANDEDNESS:single
        ( D ) TOPOLOGY:linear ( i i ) SEQUENCE DESCRIPTION: SEQ ID NO: 15:

```
          CGGAGGTTAG ATGTATAAGT TCTGCGATGA A           31
```

( 2 ) INFORMATION FOR SEQ ID NO: 16:

( i ) SEQUENCE CHARACTERISTICS:
        ( A ) LENGTH:56
        ( B ) TYPE:nucleic acid
        ( C ) STRANDEDNESS:single
        ( D ) TOPOLOGY:linear ( i i ) SEQUENCE DESCRIPTION: SEQ ID NO: 16:

```
GTCATCGTCC ACTCAGCCAC TGGATTTAAG CAGAGTTCAA ATACATCTAA     50

CCTCCG                                              56
```

( 2 ) INFORMATION FOR SEQ ID NO: 17:

( i ) SEQUENCE CHARACTERISTICS:
        ( A ) LENGTH:56
        ( B ) TYPE:nucleic acid
        ( C ) STRANDEDNESS:single
        ( D ) TOPOLOGY:linear ( i i ) SEQUENCE DESCRIPTION: SEQ ID NO: 17:

```
CAGACTGTCC ACAGCATTCC GCTGACCATC AATAAGGAAG ATACATCTAA     50

CCTCCG                                              56
```

( 2 ) INFORMATION FOR SEQ ID NO: 18:

( i ) SEQUENCE CHARACTERISTICS:
        ( A ) LENGTH:56
        ( B ) TYPE:nucleic acid
        ( C ) STRANDEDNESS:single
        ( D ) TOPOLOGY:linear ( i i ) SEQUENCE DESCRIPTION: SEQ ID NO: 18:

```
TGGCCCAACG ATGGCGAGGG CGCCTTCCAT GGAGACGCAG ATACATCTAA     50

CCTCCG                                              56
```

( 2 ) INFORMATION FOR SEQ ID NO: 19:

( i ) SEQUENCE CHARACTERISTICS:
        ( A ) LENGTH:56
        ( B ) TYPE:nucleic acid
        ( C ) STRANDEDNESS:single
        ( D ) TOPOLOGY:linear ( i i ) SEQUENCE DESCRIPTION: SEQ ID NO: 19:

```
CGGAGGTTAG ATGTATAAGC CCTTCAGCGG CCAGTAGCAT CTGACTTTGA     50

GCCTCA                                              56
```

( 2 ) INFORMATION FOR SEQ ID NO: 20:

( i ) SEQUENCE CHARACTERISTICS:
        ( A ) LENGTH:49
        ( B ) TYPE:nucleic acid
        ( C ) STRANDEDNESS:single
        ( D ) TOPOLOGY:linear ( i i ) SEQUENCE DESCRIPTION: SEQ ID NO: 20:

```
GCGCAGTCAT TTAAAATAGT AAGAATGTAT AGCCCTACCA GCATTCTGG      49
```

( 2 ) INFORMATION FOR SEQ ID NO: 21:

( i ) SEQUENCE CHARACTERISTICS:
        ( A ) LENGTH:49
        ( B ) TYPE:nucleic acid
        ( C ) STRANDEDNESS:single ( D ) TOPOLOGY:linear ( i i ) SEQUENCE DESCRIPTION: SEQ ID NO: 21:

GGAGAAATTT ATAAAGATG GATAATCCTG GGATTAAAAA TGACTGCGC    49

( 2 ) INFORMATION FOR SEQ ID NO: 22:

( i ) SEQUENCE CHARACTERISTICS:
        ( A ) LENGTH:53
        ( B ) TYPE:nucleic acid
        ( C ) STRANDEDNESS:single
        ( D ) TOPOLOGY:linear ( i i ) SEQUENCE DESCRIPTION: SEQ ID NO: 22:

GGCCACCAGG TGCAGTAAAA TAGTAAGAAT GTATAGCCCT ACCAGCATTC TGG    53

( 2 ) INFORMATION FOR SEQ ID NO: 23:

( i ) SEQUENCE CHARACTERISTICS:
        ( A ) LENGTH:53
        ( B ) TYPE:nucleic acid
        ( C ) STRANDEDNESS:single
        ( D ) TOPOLOGY:linear ( i i ) SEQUENCE DESCRIPTION: SEQ ID NO: 23:

GGAGAAATTT ATAAAGATG GATAATCCTG GGATTAAACT GCACCTGGTG GCC    53

( 2 ) INFORMATION FOR SEQ ID NO: 24:

( i ) SEQUENCE CHARACTERISTICS:
        ( A ) LENGTH:32
        ( B ) TYPE:nucleic acid
        ( C ) STRANDEDNESS:single
        ( D ) TOPOLOGY:linear ( i i ) SEQUENCE DESCRIPTION: SEQ ID NO: 24:

ATCTTGGTTA CCTGGTCATA TCCTCCCACA AC    32

( 2 ) INFORMATION FOR SEQ ID NO: 25:

( i ) SEQUENCE CHARACTERISTICS:
        ( A ) LENGTH:31
        ( B ) TYPE:nucleic acid
        ( C ) STRANDEDNESS:single
        ( D ) TOPOLOGY:linear ( i i ) SEQUENCE DESCRIPTION: SEQ ID NO: 25:

CGGGTAGCGC TGAGAACCAG GTAACCACGC T    31

( 2 ) INFORMATION FOR SEQ ID NO: 26:

( i ) SEQUENCE CHARACTERISTICS:
        ( A ) LENGTH:22
        ( B ) TYPE:nucleic acid
        ( C ) STRANDEDNESS:single
        ( D ) TOPOLOGY:linear ( i i ) SEQUENCE DESCRIPTION: SEQ ID NO: 26:

GCCGTGGTTA GAACTATGCG TC    22

( 2 ) INFORMATION FOR SEQ ID NO: 27:

( i ) SEQUENCE CHARACTERISTICS:
        ( A ) LENGTH:78
        ( B ) TYPE:nucleic acid
        ( C ) STRANDEDNESS:single
        ( D ) TOPOLOGY:linear ( i i ) SEQUENCE DESCRIPTION: SEQ ID NO: 27:

```
GCCGTGGTTA GAACTATGCG TCTCCCTAAT AGTGAGTCGT ATTAATTTCG      50

AATGCGTTCA TATCCTCCCA CAACCGCC                              78
```

( 2 ) INFORMATION FOR SEQ ID NO: 28:

( i ) SEQUENCE CHARACTERISTICS:
        ( A ) LENGTH:27
        ( B ) TYPE:nucleic acid
        ( C ) STRANDEDNESS:single
        ( D ) TOPOLOGY:linear ( i i ) SEQUENCE DESCRIPTION: SEQ ID NO: 28:

```
       CCGGGTAGCG CTGAGAAACG CATTCGA                        27
```

( 2 ) INFORMATION FOR SEQ ID NO: 29:

( i ) SEQUENCE CHARACTERISTICS:
        ( A ) LENGTH:32
        ( B ) TYPE:nucleic acid
        ( C ) STRANDEDNESS:single
        ( D ) TOPOLOGY:linear ( i i ) SEQUENCE DESCRIPTION: SEQ ID NO: 29:

```
       ATCTTGGTTA CCTGGTCATA TCCTCCCACA AC                  32
```

( 2 ) INFORMATION FOR SEQ ID NO: 30:

( i ) SEQUENCE CHARACTERISTICS:
        ( A ) LENGTH:33
        ( B ) TYPE:nucleic acid
        ( C ) STRANDEDNESS:single
        ( D ) TOPOLOGY:linear ( i i ) SEQUENCE DESCRIPTION: SEQ ID NO: 30:

```
       CGGGTATAGC GCTGAGAACC AGGTAACCAA GAT                 33
```

( 2 ) INFORMATION FOR SEQ ID NO: 31:

( i ) SEQUENCE CHARACTERISTICS:
        ( A ) LENGTH:37
        ( B ) TYPE:nucleic acid
        ( C ) STRANDEDNESS:single
        ( D ) TOPOLOGY:linear ( i i ) SEQUENCE DESCRIPTION: SEQ ID NO: 31:

```
       ATCGCCAGAA TGCTGGTCTC AGCGCTATAC GGCTGAC             37
```

BRANCHED NUCLEIC ACID PROBES

This is a division of application Ser. No. 07/827,021, filed Jan. 22, 1992, now abandoned.

FIELD OF THE INVENTION

This invention concerns nucleic acid probes, generally designed for use in hybridization assays.

BACKGROUND OF THE INVENTION

Nucleic acid is formed from nucleotide bases, e.g., uracil (U) cytidine (C), adenine (A), thymine (T) and guanine (G), formed as a single stranded linear molecule. Such a linear molecule can form a hybrid complex, or double stranded molecule (also called a duplex), with another linear molecule by forming specific base pairs, e.g., between A and T, A and U, or G and C. Such paired molecules are called complementary molecules.

Nucleic acid hybridization is a method in which two single stranded complementary molecules form a double stranded molecule. This method is commonly used to detect the presence of one single stranded molecule in a sample (the target nucleic acid) by use of a labelled probe formed of a complementary single stranded molecule. For example, Muran et al., WO 87/04165, published Jul. 16, 1987, describe a probe having a single stranded region complementary to the nucleic acid to be detected, and a double stranded region having a non-radioactive label. The general uses and design of nucleic acid probes are well known in the art, see e.g., Mifflin 35 *Clin. Chem.* 1819, 1989, and Matthews and Kricka, 169 *Anal. Biochem.* 1, 1988.

SUMMARY OF THE INVENTION

This invention features novel nucleic acid probes and methods for their use it is based upon the use of one or more probes which can form a detectable structure only in the presence of a target nucleic acid. In general, at least two portions of a nucleic acid molecule (which may be on different molecule:;) must hybridize with the target nucleic acid to create this structure. Thus, the probe ensures that little or no false positive results are observed. Such probes can be used to detect nucleic acids, and also can be used as therapeutic agents. They allow novel detection methods to be practiced, independent of the structure of the target nucleic acid. In addition, amplification of a label signal can be readily achieved, such that the probes allow extremely sensitive levels of detection of target nucleic acid.

Thus, in a first aspect, the invention features a nucleic acid hybridization probe having at least one nucleic acid strand which has at least two separate target specific regions that hybridize to a target nucleic acid sequence, and at least two distinct arm regions that do not hybridize with the target nucleic acid but possess complementary regions that are capable of hybridizing with one another. These regions are designed such that, under appropriate hybridization conditions, the complementary arm regions will not hybridize to one another in the absence of the target nucleic acid; but, in the presence of target nucleic acid the target-specific regions of the probe will anneal to the target nucleic acid, and the complementary arm regions will anneal to one another, thereby forming a branched nucleic acid structure.

In a related aspect, the invention features a method for use of such a probe to detect the presence or amount of a target nucleic acid in a sample. In this method one or more nucleic acid molecules are provided which together include at least two separate regions which hybridize with the target nucleic acid under a predetermined environmental condition. The molecules also include at least two arm regions, which (under the predetermined environmental condition) do not hybridize with the target nucleic acid, or with each other in the absence of the target nucleic acid. In the presence of the target nucleic acid, however, the arm regions do hybridize with each other. The method further includes contacting the nucleic acid molecules with a sample under the predetermined environmental conditions to allow hybridization of the arm regions if the target nucleic acid is present. Any hybridization of the arm regions is then detected as an indication of the presence or amount of the target nucleic acid.

In preferred embodiments, the detecting step includes contacting the arm regions with a resolvase (by which term is meant an enzyme able to resolve a junction by junction-specific cleavage, e.g., a 4-way junction or a 3-way junction) and detecting cleavage of the one or more nucleic acid molecules by the resolvase, performing a DNA footprint analysis of the one or more nucleic acid molecules, observing the mobility of the one or more nucleic acid molecules within a gel matrix, detecting the binding of an intercalator to the one or more nucleic acid molecules, contacting the one or more nucleic acid molecules with S1 nuclease and detecting any cleavage of the one more nucleic acid molecules by the nuclease, contacting the one or more nucleic acid molecules with a restriction endonuclease and detecting cleavage of the one more nucleic acid molecules by the endonuclease, or determining the thermal stability of the one or more nucleic acid molecules.

In other preferred embodiments, the one or more nucleic acid molecules include an intercalating molecule or nucleic acid binding molecule, e.g., an acridinium ester, or other molecule which is susceptible to chemical modification by an acid or a base, or other modification, when that molecule forms part of a single stranded nucleic acid molecule or a double stranded nucleic acid molecule, and is not susceptible to such chemical cleavage when the molecule is present in the other of the single stranded nucleic acid molecule or double stranded nucleic acid molecule; and the detecting step includes contacting the one or more nucleic acid molecules with the chemical and determining the amount of chemical modification of the molecule; at least one of the one or more nucleic acid molecules has a target region having between eight and 30 (or 8–100) complementary bases in a region of 50 (or 1000) contiguous bases of the target nucleic acid; the arm regions form a duplex in the absence of target nucleic acid with a melting temperature (commonly referred to as Tm, which is measured as described below) 4° C. lower than the hybridization temperature in the predetermined environmental condition, most preferably 7° C. or even 10° C. lower, and in the presence of target nucleic acid form a duplex having a Tm at least 4° C. (or 7° C., or even 10° C.) greater than the hybridization temperature in the predetermined environmental condition.

In yet other preferred embodiments, one nucleic acid molecule is provided and the nucleic acid molecule has a loop region connecting the at least two arm regions; the one or more nucleic acid molecules consists of two nucleic acid molecules each having a target region and an arm region; the one or more nucleic acid molecules consists of three nucleic acid molecules each having at least one arm region, and at least two of the nucleic acid molecules having a separate target region, wherein the three nucleic acid molecules hybridize with the target nucleic acid to form at least two separate hybridized or duplex arm regions; the one or more nucleic acid molecules consists of four nucleic acid molecules each having at least one arm region, and at least two of the nucleic acid molecules have separate target regions, wherein the four nucleic acid molecules and the target nucleic acid hybridize to form at least three separate duplexes between the arm regions.

In still other preferred embodiments, the target regions hybridize with the target nucleic acid, and the arm regions hybridize together to form an arm, such that a junction is formed at the base of the arm between the two separate target regions. The one or more nucleic acid molecules or the target nucleic acid may include nucleic acid adjacent the junction which does not form a duplex with the arm regions or the target regions or the target nucleic acid, and loops out from the junction. Alternatively, the target regions include along their length, or at the ends distant from the arm regions, nucleic acid which does not form a duplex with the target nucleic acid and therefore either loops from a duplex formed between the target nucleic acid and the target region, or extends as a single stranded region from the end of the target region. In yet another alternative, the arm regions include nucleic acid which does not form a duplex with the other arm region and forms a loop extending from the arm region or extends as a single stranded molecule from the end of the arm region distant from the target region. In one example, the target regions hybridize with the target nucleic acid, and the arm regions hybridize together to form an arm, and a junction is formed at the base of the arm between the two separate target regions. One or both arm regions further has a single stranded region at the end furthest from the target region which fails to hybridize to the other arm region, and thus is available for duplex formation with another nucleic acid molecule to form a second arm. In this example, the one or more nucleic acid molecules may include a portion able to form a duplex with the single stranded regions to form a second or third arm and a second junction between the arms.

In related preferred embodiments, the at least two arm regions form an arm when hybridized with the target nucleic acid, and this arm includes a biologically or chemically active site, e.g., a restriction endonuclease site, a duplex region and a single stranded region, wherein the duplex region acts as a primer for a DNA polymerase, a promoter for an RNA polymerase, e.g., which can be transcribed to form a plurality of RNA transcripts, a DNA-RNA duplex susceptible to cleavage by RNAseH, and a chemical active to cleave adjacent duplex nucleic acid, e.g., Fe.EDTA.

In addition, an arm region or target region may include a single stranded region which is able to loop over a duplex region to form triple-stranded nucleic acid. Such triple stranded structures are well known in the art and can be readily designed as part of the present invention. Such a single stranded nucleic acid may also be provided separate from the rest of the nucleic acid molecules, if desired, and can be labelled by standard methodology. Alternatively, it may form part of an arm or even target region. Detection of triple stranded nucleic acid is readily performed by methods known in the art.

The method may also include the step of contacting the one or more nucleic acid molecules and the target nucleic acid with other nucleic acid molecules able to hybridize with the arm regions, or single stranded regions extending from these arm regions, to form one or more duplex regions or arms, and these other nucleic acid molecules are then able to further hybridize among themselves to form a plurality of arms or arm regions.

Thus, the above probes can be incubated under suitable hybridization conditions with a sample suspected of containing the target nucleic acid, and detection of hybridization of the complementary arm regions used as an indication of the presence of target nucleic acid. Generally, the probe is formed from two or more separate nucleic acid molecules, e.g., strands of lengths between 20 and 50 bases; and the presence of hybridization is monitored by detection of an acridinium ester within the strands.

In another related aspect, the invention features a method for creating a biologically or chemically significant site which may be distant from the target nucleic acid yet is formed only in the presence of the target nucleic acid. This site is a segment of nucleic acid which is relatively inert in relation to a specific chemical or biochemical activity when it is in the single-stranded form, but becomes active in relation to specific chemical or biochemical activity when it is hybridized with its complementary strand, or vice versa. Examples of chemical or biochemical activity include, but are not limited to, a site susceptible to double-strand specific chemical cleavage (e.g., using an Iron-EDTA complex, or providing phenanthroline to duplex nucleic acid to make the duplex susceptible to copper cleavage), restriction endonuclease digestion, RNAse H digestion (one strand of the duplex is RNA and one strand is DNA), or a site which can be acted upon by a T7 RNA polymerase, or a DNA polymerase activity, e.g., allowing primer extension activity (e.g., using Taq DNA polymerase). Other examples include sites which are digested when in the form of single stranded nucleic acid (with S1 nuclease) but is protected from such digestion when in a double stranded form. The nucleic acid hybridization probe having this site is designed as described above, except that it includes such a site, or such a site-created when the probe is hybridized with a complementary arm region. The probe is thus incubated with target nucleic acid to form a branched nucleic acid structure, as well as the desired site. Further chemistry or biochemistry is then performed as desired. This can be used, e.g., as a mode of detection, a mode of amplification, or a mode of target-mediated cleavage of nucleic acid.

In yet another related aspect, the invention features a method for mediating a biological activity within a target cell by hyridizing a probe, similar to those discussed above, to a specific target site. As described above, a probe is incubated with target nucleic acid to form a branched nucleic acid structure, including a duplex region formed between complementary arm regions. Examples of target nucleic acid in this method include essential sequences within the genome of a pathogenic organism, essential mRNA sequences produced by a pathogenic organism, and essential sequences within cancer cells. (By essential is meant that the viability of the organism or cell is reduced by at least 30%, as measured by techniques well known in the art, when such a sequence is deleted.) The duplex region formed between complementary arm regions of the probe is designed as a specific recognition site for one of a variety of therapeutic approaches, including a sequence-specific antibody recognition site (a specifically bound antibody will mediate therapy through any of a variety of well known mechanisms, e.g., a cell toxin linked to the antibody will kill the cell), and a sequence specific protein/enzyme binding (therapy is mediated by enzymatic cleavage, blocking of transcription, blocking of translation, and the like). Furthermore, the junction between nucleic acid strands can serve as the recognition site for such antibodies or proteins.

Other features and advantages of the invention will be apparent from the following description of the preferred embodiments thereof, and from the claims.

DESCRIPTION OF THE PREFERRED EMBODIMENTS

The drawings will first briefly be described.

Drawings

FIGS. 1A-1F, 4A-4B, 6A-6H, 9A-9F, and 11A-11F are general diagrammatic representation of probes of this invention (the short lines between probes in each of the Figures represent hydrogen bonding between the probes, and are not representative of actual number of bases or hydrogen bonds);

FIGS. 2A-2E, and 3A-3B, 5A-5G, 7, 8, 10, and 12A-12C are specific examples of the probe shown respectively in FIG. 1A, 4A, 6A, 7, 9F, and 11E;

FIGS. 15A-15F are diagrammatic representations of various detection systems useful in the invention;

Figure 21:
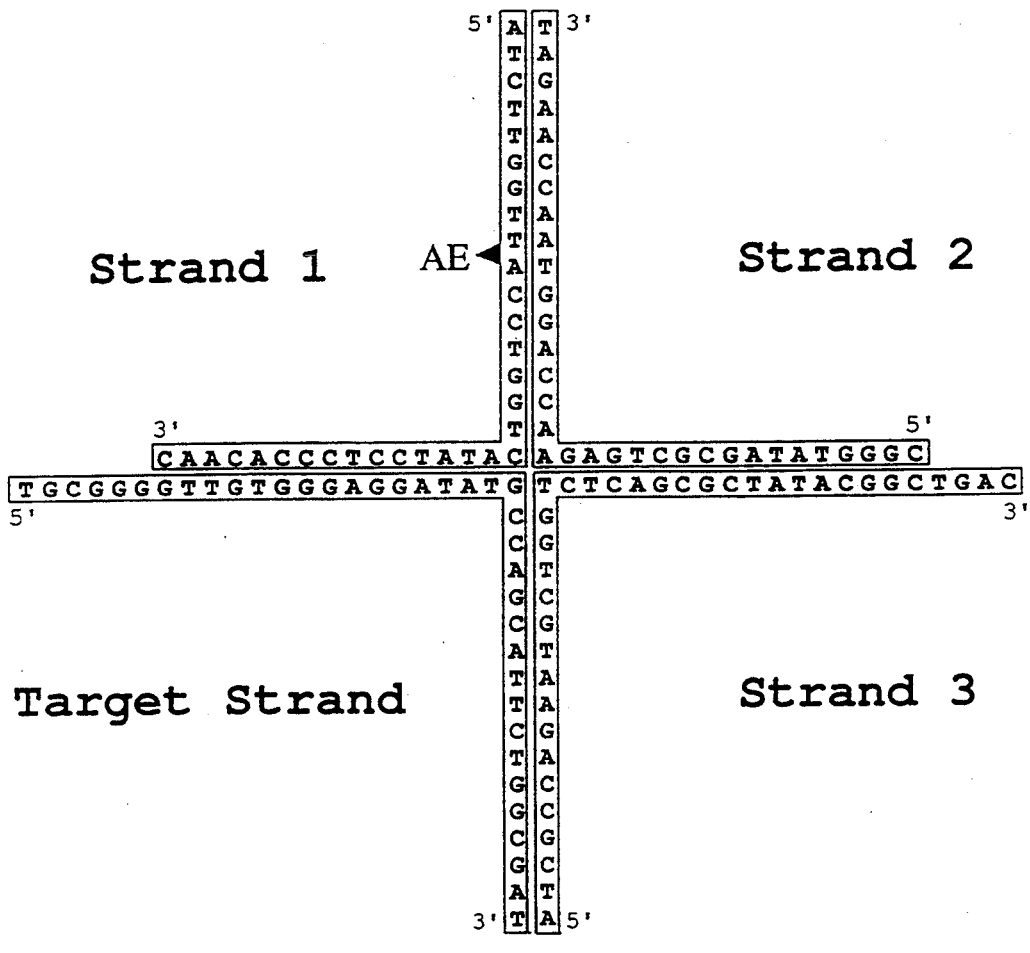
Figure 22I:
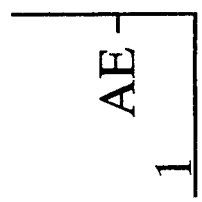
Figure 22H:
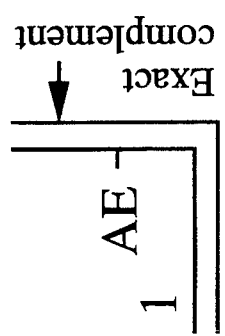
Figure 22G:
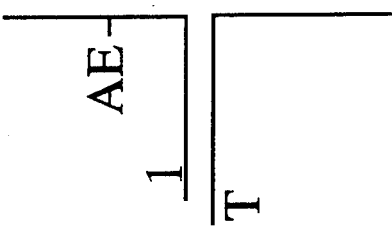

FIGS. 19A and 19B, and 20A-20C are diagrammatic representations of target independent probe amplification systems;

FIG. 21 is a diagrammatic representation of three probes producing a 4-way junction; and FIGS. 22A-22I are diagrammatic representations of various embodiments of the probes shown in FIG. 21.

Probes

Figure 1A:
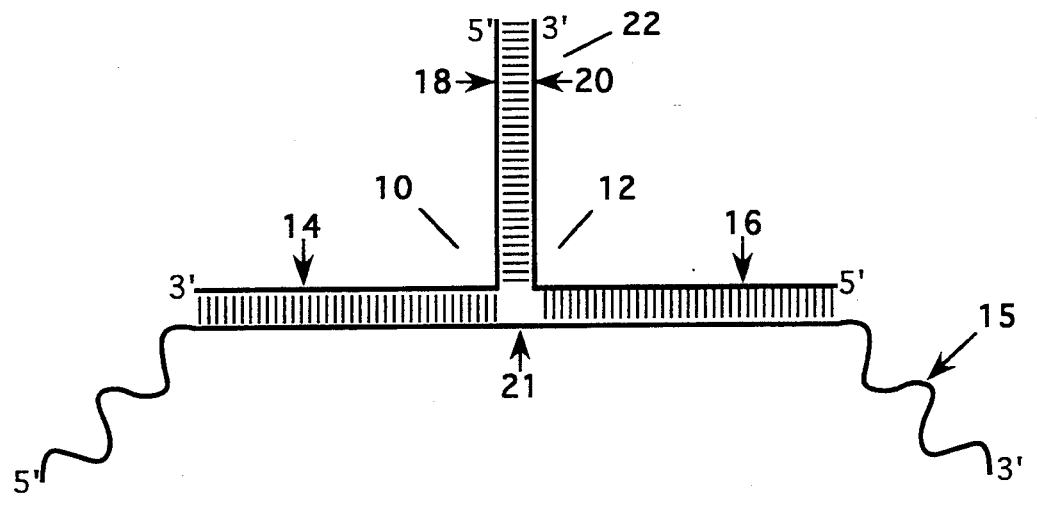
Figure 1B:
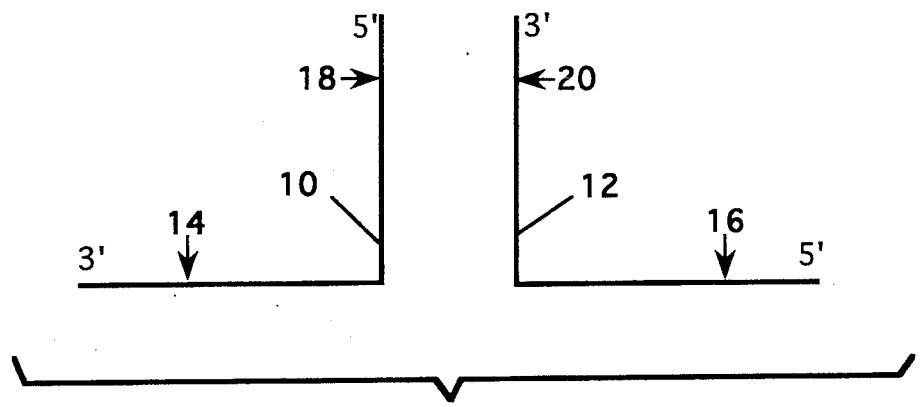
Figure 1C:
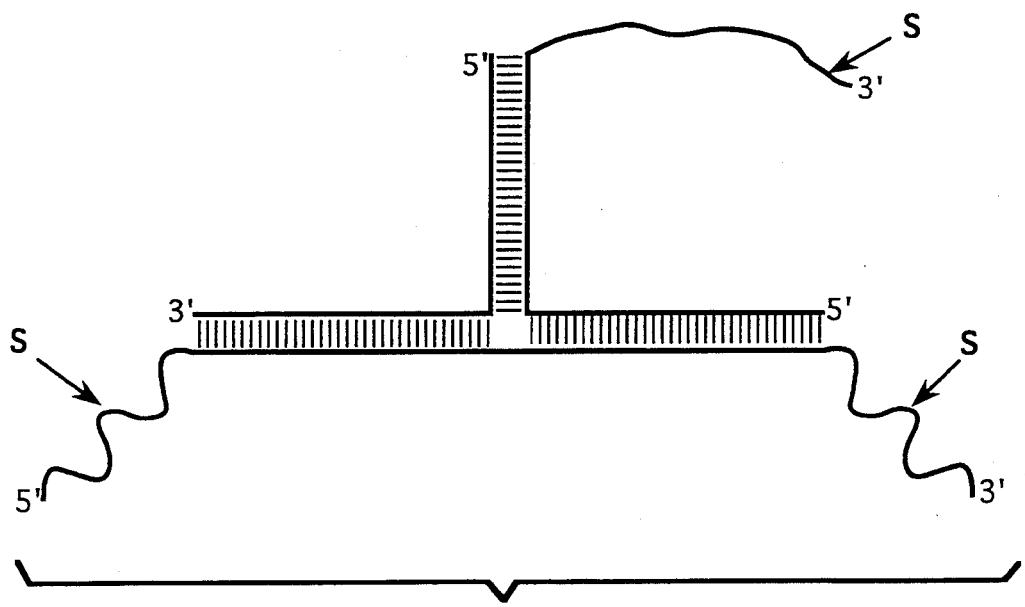
Figure 1D:
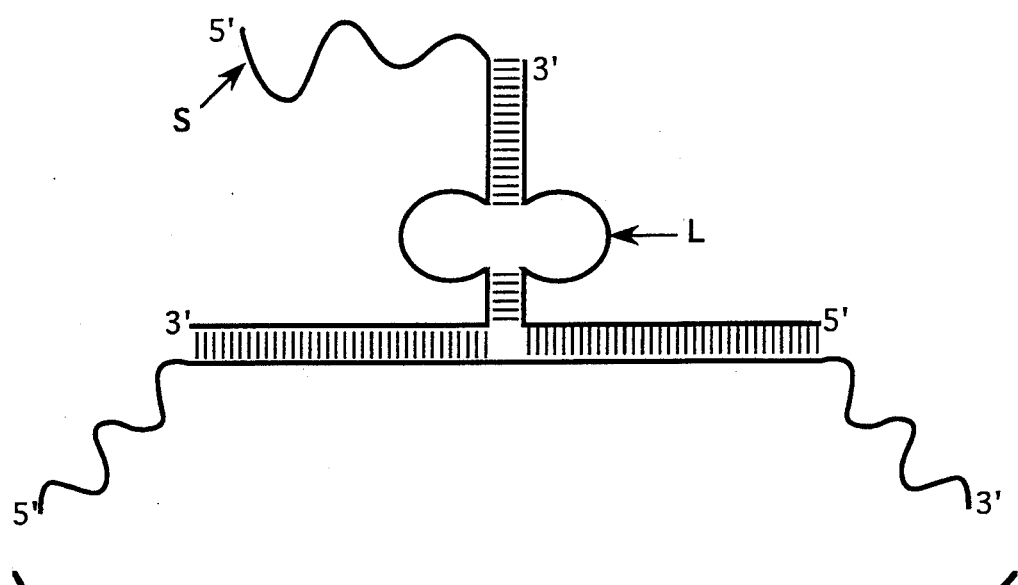
Figure 1E:
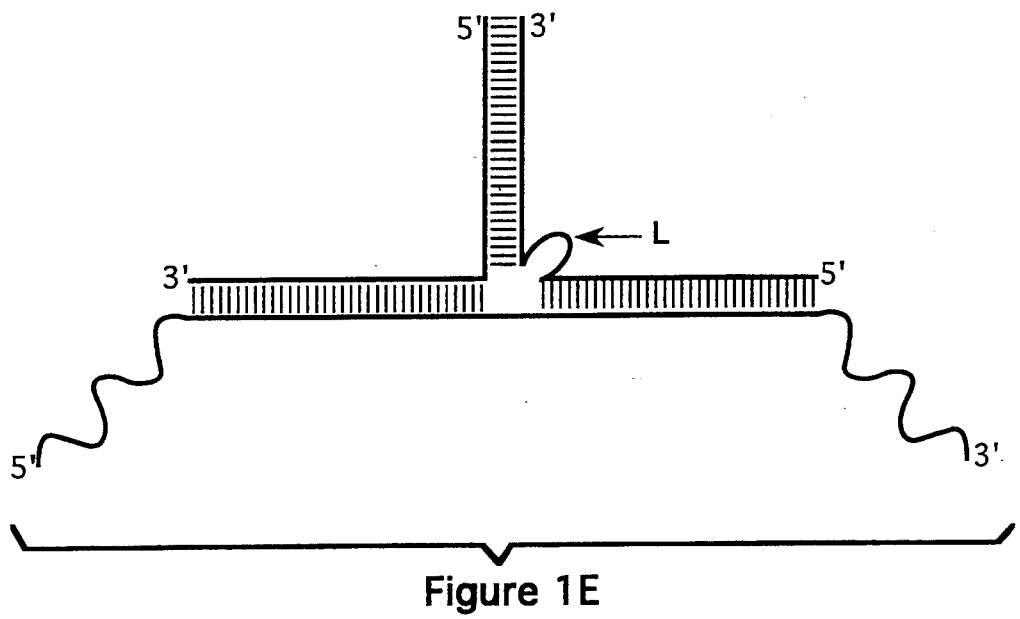
Figure 1F:
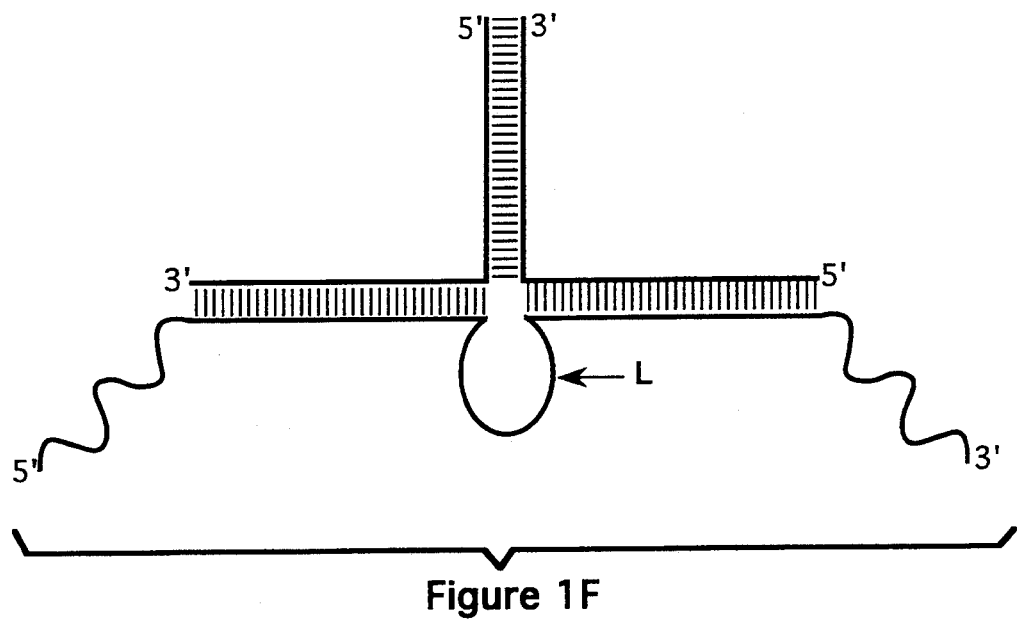

Referring to FIGS. 1A and 1B, there is shown one example of a probe of this invention demonstrating the general structure of each probe of this invention. The probe shown is formed from two separate strands 10, 12 each of which possess a target specific region 14, 16 able to hybridize under hybridizing conditions to a target nucleic acid 15. Each strand also possesses an arm region 18, 20 which hybridize together to form an arm 22 generally only in the presence of the target nucleic acid. When an arm is formed so also is a junction 21 between the arm and hybridized target regions. Arm regions and target specific regions can be designed so that hybridization of the target specific regions to target nucleic acid is observed under hybridization conditions only when both strands are present in the hybridization mixture, and both are hybridized to target nucleic acid and to each other at their arm regions.

Thus, as generally discussed above, nucleic acid hybridization probes of this invention form branched nucleic acid structures (i.e, structures having at least one arm extending from a target nucleic acid and not directly hybridized with the target nucleic acid) upon interaction with and hybridization to a target nucleic acid. The probes are designed so that formation of this branched structure is target-dependent. Therefore, detection of branch formation is a measure of the presence and the amount (if detection is quantitative) of target nucleic acid in a sample. More than one branch can be formed, but only one branch must be formed in a target-dependent manner. The probe can be a single nucleic acid strand or can be multiple strands. Furthermore, the strand (or strands) can be DNA, modified DNA, RNA, modified RNA, or various combinations thereof. By "modified DNA or RNA" is meant any nucleic acid structure differing from naturally occurring DNA or RNA molecules, e.g., DNA or RNA, containing modified bases (e.g., methyl cytosine, or inosine), or modified internucleotide linkages (e.g., phosphorothioate, or methyl phosphonate). The probe must have at least two separate regions that hybridize specifically with the target nucleic acid, and at least two arm regions (i.e., regions that do not hybridize with the target) that are complementary to one another and form a stable duplex only in the presence of target. Since these complementary arm regions hybridize only in the presence of target nucleic acid, detection of this duplex region is the preferred method to assay for the presence of the target nucleic acid.

There are numerous methods for detecting hybridization of branched nucleic acid probes with target. Examples of detection of branched nucleic acids include use of junction specific cleavage with a resolvase enzyme (e.g., where cleavage of a labelled probe strand is detected), DNAse footprinting, gel retardation assays, and binding of a labeled, junction specific intercalating compound (where the target is captured and the presence of label detected). While purified 4-way junction cleaving resolvases are known in the art, 3-way junction cleaving enzymes and other junction specific enzymes can be readily purified by art known methods, for example, by purifying enzymes biochemically which have an activity which cleaves a desired 3-way junction. Examples of detection of the duplex formed between complementary arm regions include DNAse footprinting, S1 nuclease digestion (an arm region is labelled; if the arms form a duplex, they will not be digested with nuclease S1; if the arms do not form a duplex, they will be digested with nuclease S1), restriction endonuclease cleavage of a site created by duplex formation between complementary arm regions, capture of target nucleic acid followed by analysis of the thermal stabilities of the associated duplex(es) (using a labelled probe strand(s); the complete branched nucleic acid structure will have a higher thermal stability than any partial formation; if no formation has occurred, a different signal will be associated with the captured target nucleic acid compared to when a branch is formed). Also the juxtapositioning of two synergistic labels on opposite probe arms can be detected. More generally, it will be readily recognized by those skilled in the art that any method that detects the formation of branched DNA, or the formation of a complementary arm duplex, can be utilized in this method to indicate the presence of target.

The preferred method of detection is the use of the Hybridization Protection Assay (HPA) described by Arnold et al., 35 Clin. Chem. 1588, 1989. This method utilizes a chemiluminescent acridinium ester (AE) label covalently attached to a synthetic oligonucleotide probe. The assay format is completely homogeneous (i.e., requires no physical separation steps) and is based on chemical hydrolysis of the ester bond of the AE molecule, cleavage of which renders the AE permanently non-chemiluminescent. Conditions have been developed where the hydrolysis of this ester bond is rapid for unhybridized AE-labeled probe (AE-probe) but slow for hybridized AE-probe. Therefore, after hybridization of the AE-probe with its complementary nucleic acid (under conditions that do not promote ester hydrolysis), the reaction conditions are adjusted so that the chemiluminescence associated with unhybridized AE-probe is rapidly reduced to low levels, while the chemiluminescence associated with hybridized AE-probe is minimally affected. Following this differential hydrolysis process, any remaining chemiluminescence is a direct measure of the amount of duplex formed. This assay method is used in the present invention by attaching one or more AE labels to one or more of the nucleic acid strands of the probe and assaying for duplex formation using the differential hydrolysis procedure described above.

Two Component Probes

One configuration of branched nucleic acid probe used for the detection of target nucleic acids is shown schematically in FIGS. 1A and 1B. In this configuration the probe consists of two separate nucleic acid strands; these strands are preferably synthetic oligonucleotides. Each strand possesses a probe region which hybridizes with the target nucleic acid and an arm region. The two arm regions are complementary to one another (by which is meant not that they are necessarily perfectly complementary, since they may possess portions that are not complementary to each other at all, but that under hybridizing conditions a stable duplex is formed). These arm regions are designed such that the melting temperature, or Tm, of the associated duplex in the absence of target is less than the operating temperature of the assay, preferably 4° C. less (more preferably 7° C. or 10° C.) than the operating temperature, so that little or no hybridization of the arm regions occurs in the absence of target nucleic acid. The Tm is defined as the temperature at which 50% of a given nucleic acid duplex has melted (i.e., has become single-stranded). The Tm is dependent on environmental conditions such as the cation concentration of the solution. The desired Tm is typically achieved by manipulation of the length and nucleotide base composition of the complementary regions. Other methods can also be utilized to adjust duplex Tm, including but not limited to incorporation of mismatches, replacement of some or all of the guanosine residues with inosine, and modifying the phosphate backbone, e.g., with phosphorothioate internucleotide linkages. When utilizing the HPA format at 60° C., the preferred length of exactly complementary, unmodified arm regions is approximately 8 to 20 contiguous bases (dependent on base composition and sequence). Other environmental conditions would potentially lead to a different size range; this is easily determined empirically.

Upon contacting the probe with a solution containing the target nucleic acid, the probe regions of the two strands will hybridize to their respective target regions, which are typically adjacent to one another, as shown in FIG. 1 (they do not have to be immediately adjacent, see infra). When this occurs, the arm regions of the two probe strands are constrained to be in close proximity to one another, thus increasing the stability of the associated duplex. The arm regions are designed such that the Tm of the duplex formed in the presence of target is approximately equal to or above the operating temperature of the assay, preferably 4° C. above (more preferably 7° C. or 10° C.) the operating temperature such that the arms will form a duplex. As indicated above, when utilizing the HPA format at 60° C., the preferred length of the arms is approximately 8 to 20 contiguous complementary bases (dependent on base composition and sequence).

The probe regions of the two separate strands can be designed in a variety of manners. For example, these regions can be designed similarly to the arm regions in that the Tm of either region alone (i.e., one probe strand plus the target strand) is below the operating temperature, but is above the operating temperature when both probe strands and the target strand are present and the arm regions are hybridized. They can also be designed such that the Tm's of the probe regions are both above the operating temperature, or they can be designed such that one Tm is above and one Tm is below the operating temperature. Whatever design is chosen, the requirement that the arm regions form a stable duplex only in the presence of target must be met. The probe regions are preferably between 8 and 50 nucleotides in length, more preferably between 8 and 30 nucleotides in length. These regions can be longer, but most applications do not require this additional length, and synthesis of these longer oligomers is more costly and time consuming than the shorter oligomers.

One or both probe sequences is chosen to react with the desired target nucleic acid(s) and preferably to not react with any undesired target nucleic acid(s) (i.e., cross-react). If one probe region hybridizes with an undesired target but the other probe region does not, the assay will still function properly since both probe segments have to hybridize in order for the arm regions to hybridize.

When utilizing the HPA format, the AE label is typically placed in the arm region of the probe. In the absence of target, this region will be single-stranded and the AE will be susceptible to rapid ester hydrolysis. In the presence of target, this region will be double-stranded and the AE will be protected from ester hydrolysis. An AE label can be placed in one strand, the other strand, or both strands (thereby leading to an increase in signal and assay sensitivity). Multiple labels can be placed in each strand, further improving assay sensitivity. The AE label can also be placed in one or the other (or both) of the probe regions. Multiple labels could also be used in this configuration. Furthermore, AE could be utilized in any combination of the placements just described.

To detect a target nucleic acid in a sample using the branched nucleic acid probe described above in the HPA format, the following general procedure is used: 1) add the branched nucleic acid probe to the sample, 2) incubate to allow annealing of the appropriate regions to occur, 3) add a reagent to effect differential hydrolysis of the AE label(s), and 4) detect any remaining chemiluminescence as an indication of the presence or amount of any target nucleic acid present. The annealing conditions can be varied depending on the exact application, the design of the probe, the nature of the target nucleic acid and the composition of the sample in which the target is contained. The conditions must be chosen, however, to fulfill the Tm requirements stated above. For the HPA format, the incubation temperature is preferably between 5° and 70° C., more preferably between 30° and 65° C.; the pH of the annealing step is preferably between 4.5 and 8.5, and most preferably between 4.5 and 5.5 (greater stability of the AE during the annealing step is achieved in the lower pH range; however, methods exist to stabilize the AE in the higher pH range, as described by Hammond et al., 6 *J. Biolum. and Chemilum.* 35, 1991). The concentration of the monovalent salt counterion is preferably between 50 and 1000 mM, more preferably between 200 and 800 mM; it is preferred to include detergent in the annealing step (this prevents the AE from aggregating and from sticking to the walls of the tube, and the piper tips), preferably at concentrations between 0.1 and 10% (w/v), and more preferably between 1 and 10%. One skilled in the art will recognize that alternate annealing conditions that lead to the desired hybridization characteristics may also be used in this invention.

Although a specific example is provided below, this is not limiting in the invention. Those of ordinary skill in the art will recognize many variations, examples of which are provided in FIGS. 1C–1F, where various loops (labelled L) are shown in an arm, target nucleic acid or at a junction, and single stranded nucleic acid (labeled S) may also be present (e.g., for later duplex function with more probes as described below).

EXAMPLE 1

Figure 2A:
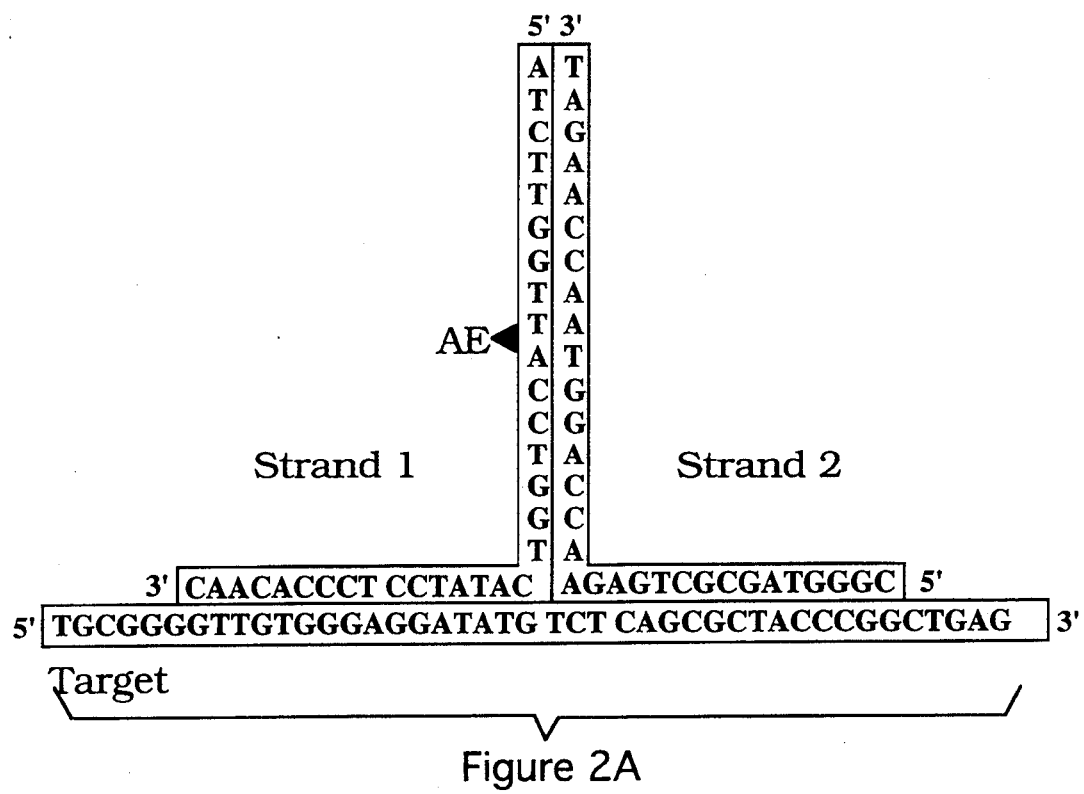

A specific example of the general configuration shown in FIG. 1 is shown in FIG. 2A. The target strand is a synthetic DNA oligomer 43 bases in length with a sequence corresponding to a region of the 23S ribosomal RNA (rRNA) subunit of *Mycobacterium tuberculosis*. The 2 strands of the branched nucleic acid probe form a 3-way junction with the target strand as shown in FIG. 2A. A single AE is covalently tethered to strand 1 between a T and an A residue as shown.

Oligonucleotides were synthesized using standard phosphoramidite solid-phase chemistry (Caruthers et al., 154 *In Methods Enzymol.* 287, 1987) on a Biosearch Model 8750 or ABI 380A DNA-Synthesizer and purified using standard polyacrylamide gel electrophoresis. Strand 1 was AE-labeled as previously described by Arnold and Nelson, PCT Publication No. WO 89/02896, published Apr. 6, 1989.

The following annealing reactions were carried out for 1 hour at 60° C. in 30 μl of 0.1M lithium succinate buffer, pH 5.2, 2 mM EDTA, 2 mM EGTA, and 10% (w/v) lithium lauryl sulfate: Hybrid—0.5 pmol of target strand, 0.05 pmol of probe strand 1 (the AE-labeled strand), and 2.5 pmol of probe strand 2. Control 1—0.05 pmol of probe strand 1, and 2.5 pmol of probe strand 2. Control 2—0.05 pmol of probe strand 1. Reagent Blank—No target or probe.

To demonstrate that the arm regions were hybridizing only in the presence of target, the half-life of AE hydrolysis for each of the reactions above were measured using the protocol described previously (Arnold et al., 35 *Clin Chem.* 1588, 1989). The following results were obtained:
Hybrid: 11.5 minutes
Control 1: 0.54 minutes
Control 2: 0.51 minutes These data reveal that the AE is not protected from ester hydrolysis in the absence of target (compare Control 1 with Control 2), but is protected from hydrolysis in the presence of target (Hybrid), thus demonstrating the hybridization of the arm regions only in the presence of target nucleic acid.

Figure 2B:
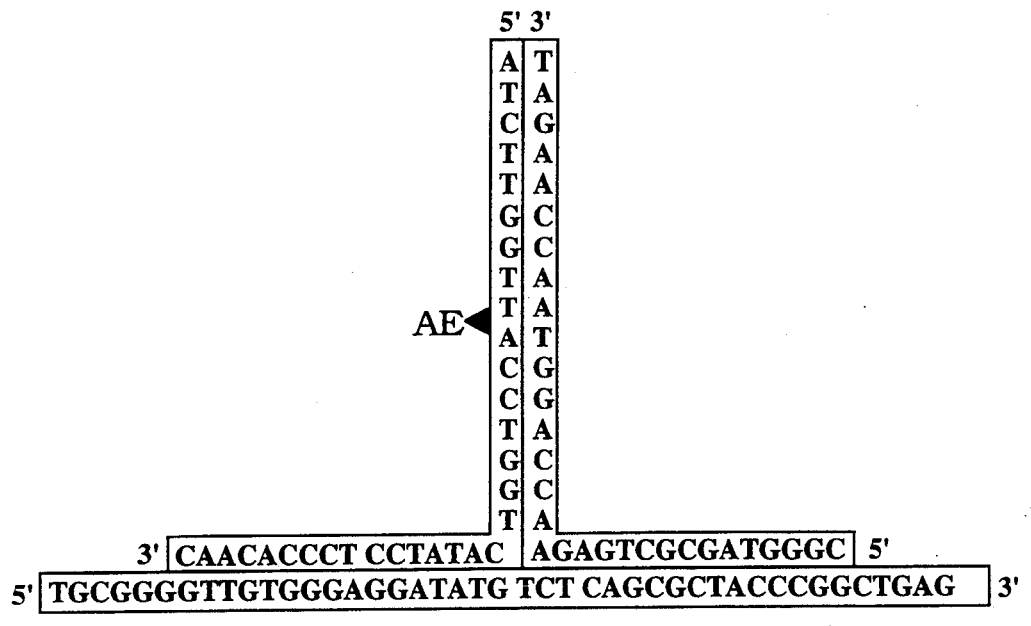

This system was further evaluated by measuring the Tm's of the various configurations represented schematically in FIG. 2B. The Tm's were measured according to the following protocol:

1. After annealing as described above, samples to be analyzed were diluted in 0.1M lithium succinate buffer, pH 5.2, 2 mM EDTA, 2 mM EGTA, 10% (w/v) lithium lauryl sulfate to approximately 100,000 relative light units (RLU; this is the unit of chemiluminescence used in these protocols; see Arnold et al., 35 *Clin Chem.* 1588, 1989) per 100 μl.

2. Separate 100 μl aliquots were pipetted into 12×75 mm assay tubes. Each sample to be analyzed was incubated for 7 minutes at each of the following temperatures—40°, 43°, 46°, 49°, 52°, 55°, 58°, and 62° C. for oligomers with Tm's of 56° C. and below; and 50°, 53°, 56°, 59°, 62°, 65°, 68°, and 71° C. for oligomers with Tm's above 56° C. After incubation, each tube was placed in an ice bath.

3. After all incubations were complete, all tubes were removed from the ice bath and to each 300 μl of 0.15M sodium tetraborate buffer, pH 7.6, 5% (v/v) Triton X-100 added, and vortex mixed. All tubes were incubated at 40° C. for 20 minutes for oligomers with Tm's of 56° C. and below, and at 50° C. for 15 minutes for oligomers with Tm's above 56° C. The tubes were placed on ice for 30 seconds, and then at room temperature (20°–25° C.).

4. Chemiluminescence was measured in a luminometer (LEADER I, Gen-Probe, CA) by the automatic injection of 200 μl of 0.1% $H_2O_2$, 1N NaOH, followed by measurement of signal for 5 seconds. The tubes were blotted with a moist tissue or paper towel before measuring the chemiluminescence.

5. The Control value was subtracted from each corresponding Hybrid value, and the resulting data plotted as chemiluminescence versus temperature. The Tm was determined graphically as the temperature at which 50% of the maximum chemiluminescence is lost.

The temperature range and the exact temperature intervals used can vary with the exact characteristics of the AE-oligomer being characterized.

Figure 2C:
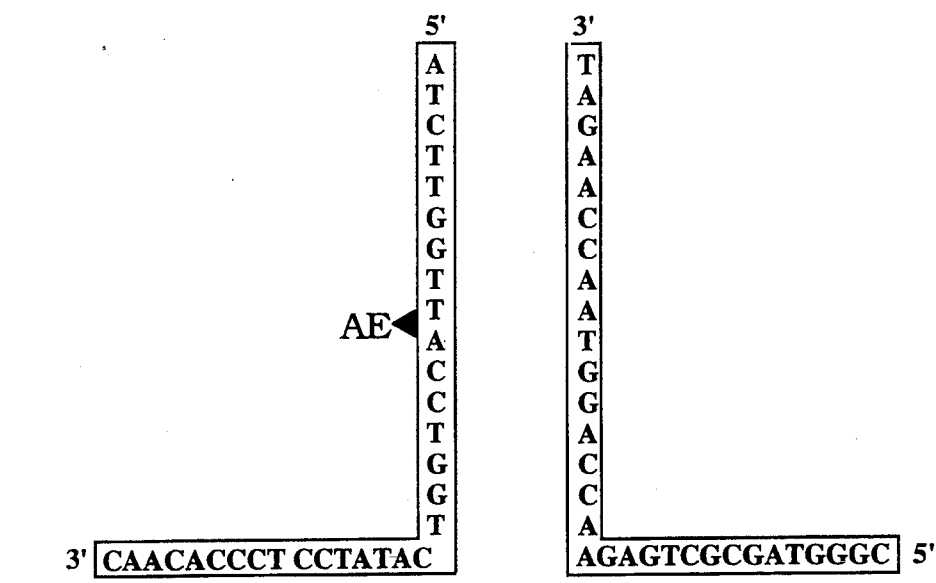
Figure 2D:
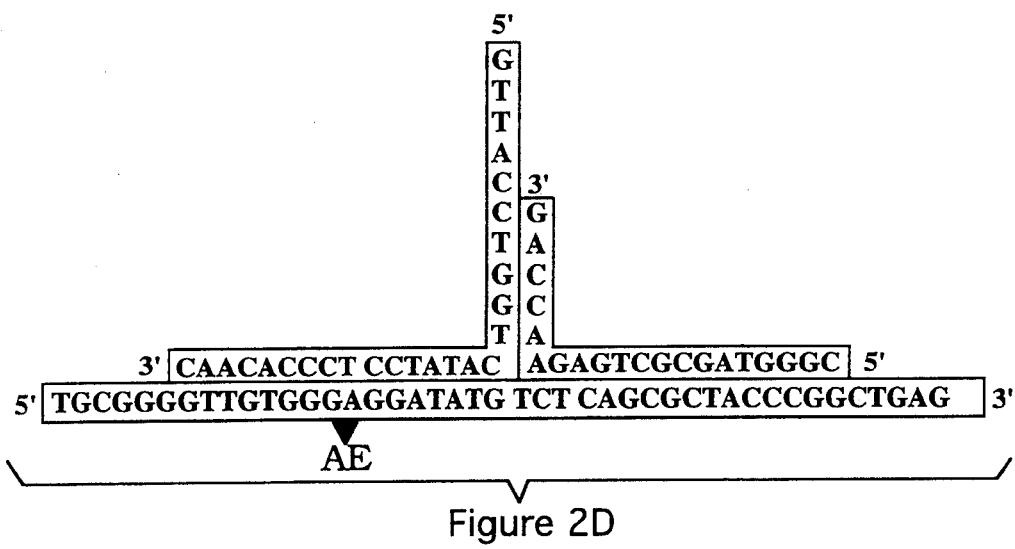
Figure 2E:
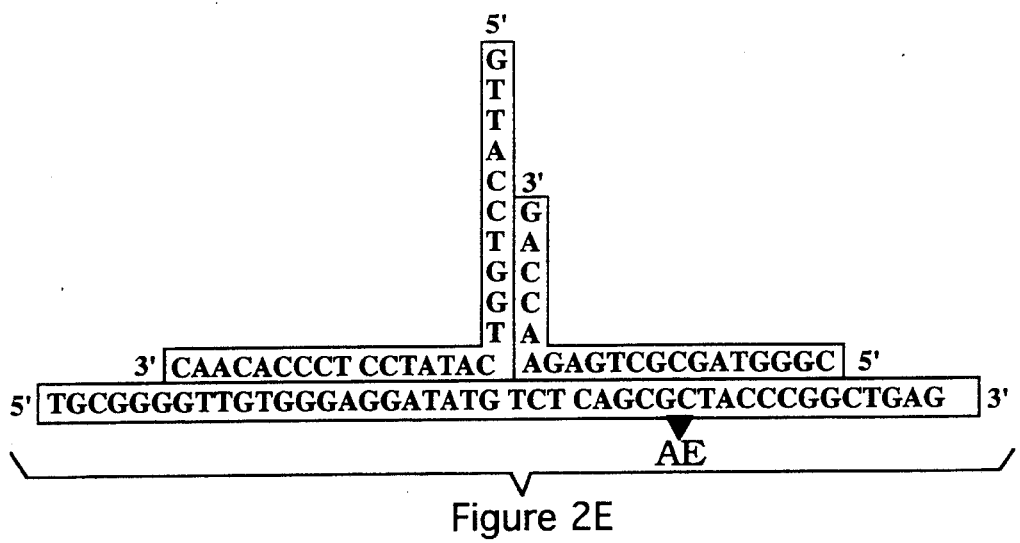

The following Tm's were obtained:
Structure 1 (FIG. 2B) Tm=62° C.
Structure 2 (FIG. 2C) Tm=50° C.

These data demonstrate that the duplex associated with the arm regions has a Tm well below 60° C. (the operating temperature used above in the hydrolysis rate determination) in the absence of target, and a Tm above 60° C. in the presence of target.

The system was further characterized by measuring Tm's of the various structures depicted in FIG. 2B–2E in 8 mM lithium succinate buffer, pH 5.5, 100 mM NaCl, 10 mM $MgCl_2$, and 10 mM Tris-HCl (this reagent replaces the diluting reagent in step 1 of the above protocol). The following Tm's were obtained: 0
Structure 1 (FIG. 2B) Tm=59° C.
Structure 2 (FIG. 2C) Tm=47° C.
Structure 3 (FIG. 2D) Tm=47° C.
Structure 4 (FIG. 2E) Tm=45° C.

For this particular design, not only is the Tm of the arm region much lower in the absence of target than in the presence of target, but the duplex regions formed between the target and the probe regions are less stable in the absence of the complete arm duplex (see FIG. 2)

than in the presence of the complete arm duplex. This demonstrates that the branched nucleic acids of this invention can be used to manipulate the Tm of a nucleic acid duplex.

Other possible configurations for acridinium ester label locations, or use of a restriction enzyme (BstIII) for duplex detection are shown in FIGS. 2B–2E.

EXAMPLE 2

Figure 3A:
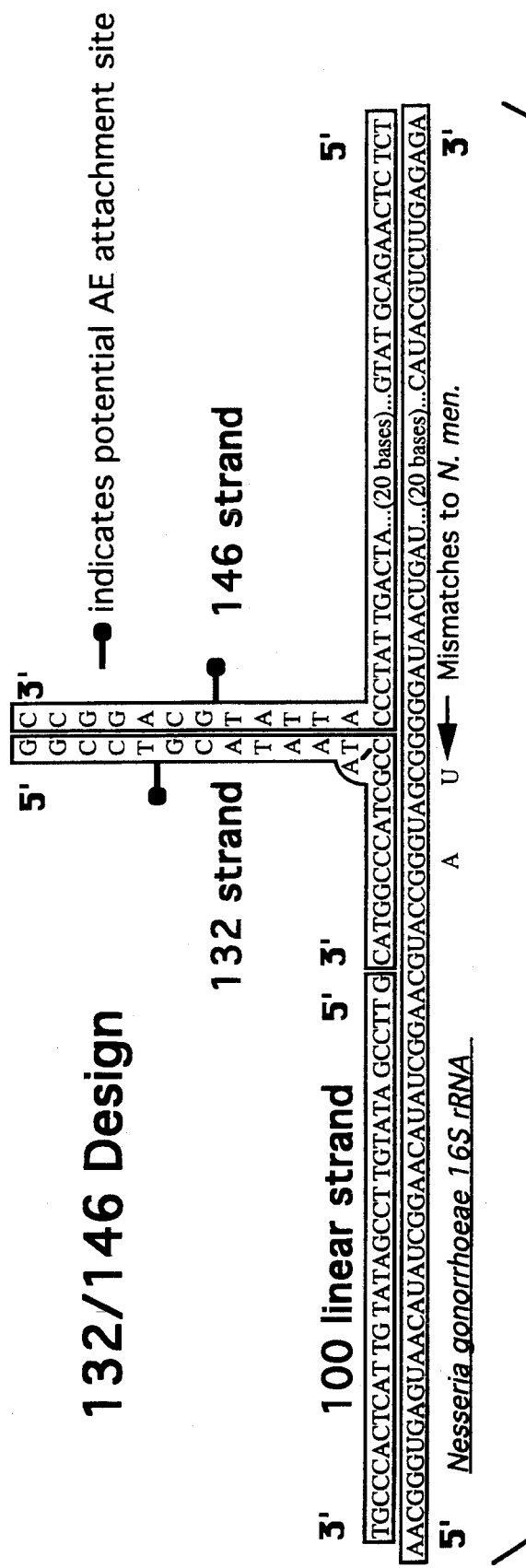
Figure 3B:
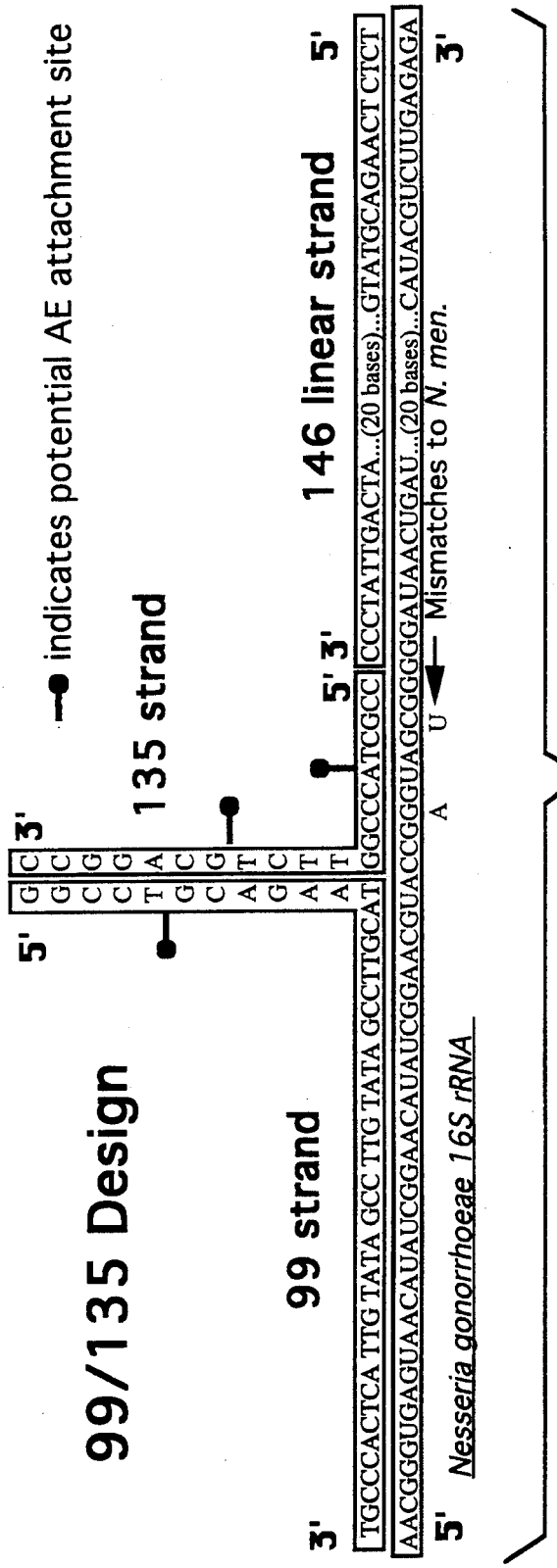

Another example of the general structure shown in FIG. 1 is shown in FIGS. 3A and 3B. In this design ribosomal RNA (rRNA) from *Neisseria gonorrhoeae* is the target nucleic acid. All oligomers were synthesized and AE-labeled as described in Example 1 above. Two basic designs were evaluated, with junctions at slightly different locations within a given region of the rRNA (99/135 FIG. 3B and 132/146 FIG. 3A designs). A variety of linker-arm placements were evaluated, as indicated below. Furthermore, the exactly complementary target nucleic acid (*N. gonorrhoeae*) as well as a potentially cross-reacting target nucleic acid with 2 mismatches (*N. meningitidis*) were evaluated.

Hybridization characteristics of the different regions were evaluated using differential hydrolysis and Tm analyses as described in Example 1 with the following specific conditions:

| Sample | Target nucleic acid (RNA) Type | Amount | Label | Amount | Label | Amount | Label | Amount |
|---|---|---|---|---|---|---|---|---|
|  |  |  | Oligo 99 |  | Oligo 135 |  | Oligo 146 |  |
| 1 | N. gon. | 0.6 pmol | AE | 0.1 pmol | none | 2 pmol | none | 2 pmol |
| 2 | N. gon. | 0.6 pmol | none | 2 pmol | AE(1) | 0.1 pmol | none | 2 pmol |
| 3 | N. gon. | 0.6 pmol | AE | 0.1 pmol | AE(1) | 0.1 pmol | none | 2 pmol |
| 4 | N. gon. | 0.6 pmol | none | 2 pmol | AE(2) | 0.1 pmol | none | 2 pmol |
| 5 | N. men. | 0.6 pmol | AE | 0.1 pmol | none | 2 pmol | none | 2 pmol |
| 6 | N. men. | 0.6 pmol | none | 2 pmol | AE(1) | 0.1 pmol | none | 2 pmol |
| 7 | N. men. | 0.6 pmol | AE | 0.1 pmol | AE(1) | 0.1 pmol | none | 2 pmol |
| 8 | N. gon. | 0.6 pmol | none | 2 pmol | AE(2) | 0.1 pmol | none | 2 pmol |
|  |  |  | Oligo 132 |  | Oligo 146 |  | Oligo 100 |  |
| 9 | N. gon. | 0.6 pmol | AE | 0.1 pmol | none | 2 pmol | none | 2 pmol |
| 10 | N. gon. | 0.6 pmol | none | 2 pmol | AE | 0.1 pmol | none | 2 pmol |
| 11 | N. gon. | 0.6 pmol | AE | 0.1 pmol | AE | 0.1 pmol | none | 2 pmol |
| 12 | N. men. | 0.6 pmol | AE | 0.1 pmol | none | 2 pmol | none | 2 pmol |
| 13 | N. men. | 0.6 pmol | none | 2 pmol | AE(1) | 0.1 pmol | none | 2 pmol |
| 14 | N. men. | 0.6 pmol | AE | 0.1 pmol | AE(1) | 0.1 pmol | none | 2 pmol |

Hybridizations with *N. gonorrhoeae* were performed at 60° C.; hybridizations with *N. meningitidis* were performed at 45° or 50° C.; controls contained all the components except target; linear oligonucleotides 100 and 146 are "helper" probes that open the secondary structure of the rRNA, and are not related to the branched nucleic acid probes of this invention. The following results were obtained:

| Sample | Target | Tm (°C.) | Hydrolysis Half-life (min) Hybrid | Control | D.H. Ratio |
|---|---|---|---|---|---|
| 1 | N. gon. | 68.2 | 14.3 | 0.48 | 29.8 |
| 2 | N. gon. | 70.0 | 6.1 | 0.51 | 12.7 |
| 3 | N. gon. | 68.0 | 8.2 | 0.50 | 16.4 |
| 4 | N. gon. | 68.5 | 18.8 | 0.47 | 40.0 |
| 9 | N. gon. | 70.0 | 12.8 | 0.49 | 26.1 |
| 10 | N. gon. | 72.0 | 8.0 | 0.43 | 18.6 |
| 11 | N. gon. | 67.5 | 8.6 | 0.43 | 20.0 |
| 5 | N. men. | 59.0 |  |  |  |
| 6 | N. men. | 59.0 |  |  |  |
| 7 | N. men. | 54.5 |  |  |  |
| 8 | N. men. | 56.0 |  |  |  |
| 12 | N. men. | 58.5 |  |  |  |
| 13 | N. men. | 61.0 |  |  |  |

-continued

| Sample | Target | Tm (°C.) | Hydrolysis Half-life (min) Hybrid | Control | D.H. Ratio |
|---|---|---|---|---|---|
| 14 | N. men. | 57.0 |  |  |  |

DH ratio is the ratio of half-life for hybrid and control. *Neisseria meningitidis* DH ratios were near unity (data not shown). Thus, no hybridization was observed.

The DH ratios for the *N. gonorrhoeae* target clearly demonstrate that the arm regions form a stable duplex only in the presence of an RNA nucleic acid target. These two designs each have a strand with a long probe region and a strand with a short probe region, thus demonstrating the flexibility of this design parameter. Furthermore, the data demonstrate that several different AE placements yield similar results, including 2 AE's per probe (one per each strand; samples 3 and 11). Some AE placements yield higher DH ratios than other placements, but all show protection only in the presence of target. The Tm data for the *N. gonorrhoeae* target show that all structures tested yield Tm's well above the operating temperature (60° C. in this case).

The data generated with the *N. meningitidis* target demonstrate that the system can be tuned to not significantly cross-react with a closely related target nucleic acid, thus improving its utility as an assay. The differences in Tm for each structure between *N. gonorrhoeae* and *N. meningitidis* range between 9.2° and 13.5° C.

The 99/135 system was also evaluated for its ability to detect decreasing amounts of target nucleic acid (*N. gonorrhoeae*); cross-reaction with $10^{-1}$ μg (63 fmol) of *N. meningitidis* was also tested. The assay format was as follows: Target and probe were annealed in 100 μl of 0.1M lithium succinate buffer, pH 5.2, 2 mM EDTA, 2 mM EGTA, and 10% (w/v) lithium lauryl sulfate for 60 min at 60° C. 300 μl of 0.15M sodium borate buffer, pH 7.6, containing 5% Triton X-100 detergent were added, vortexed and incubated at 60° C. for 10 minutes. Chemiluminescence was measured in a luminometer (LEADER I, Gen-Probe, CA) by the automatic injection of 200 μl of 0.4N $HNO_3$, 0.1% $H_2O_2$, and then 200 μl of 1N NaOH, followed by measurement of signal for 5 seconds.

In this example, the following probe mixtures were used: Probe mix 1—0.1 pmol of AE-labeled oligo 99, 0.5 pmol of oligo 135, and 2 pmol of oligo 146; Probe mix 2—0.1 pmol of AE-labeled oligo 135, 0.5 pmol of oligo 99, and 2 pmol of oligo 146; Probe mix 3—0.1 pmol of AE-labeled oligo 99, 0.1 pmol of AE-labeled oligo 135, and 2 pmol of oligo 146. The amounts of target assayed and the results are indicated below:

|  | Probe Mix | | |
| --- | --- | --- | --- |
|  | 1 | 2 | 3 |
| [N. gon.] (μg) | | | |
| $5 \times 10^{-2}$ | 370,848 | 188,161 | 475,161 |
| $10^{-2}$ | 66,398 | 37,016 | 112,844 |
| $10^{-3}$ | 9,242 | 4,730 | 14,249 |
| [N. men.] (μg) | | | |
| $10^{-1}$ | 2,358 | 5,363 | 2,362 |

These data demonstrate that the designs shown here are useful in detecting small amounts of nucleic acid in a full assay format. Furthermore, label amplification is demonstrated in probe mix 3, which contains 2 AE-labeled strands instead of 1 (as in probe mixes 1 and 2). Cross-reaction with the very closely related *N. meningitidis* RNA was minimal for probe mixes 1 and 3; the slight cross-reaction seen in probe mix 2 is approximately 100-fold lower than the positive signal, and was reduced to minimal levels by slightly increasing the operating temperature of the assay.

One Component Probes

Figure 4A:
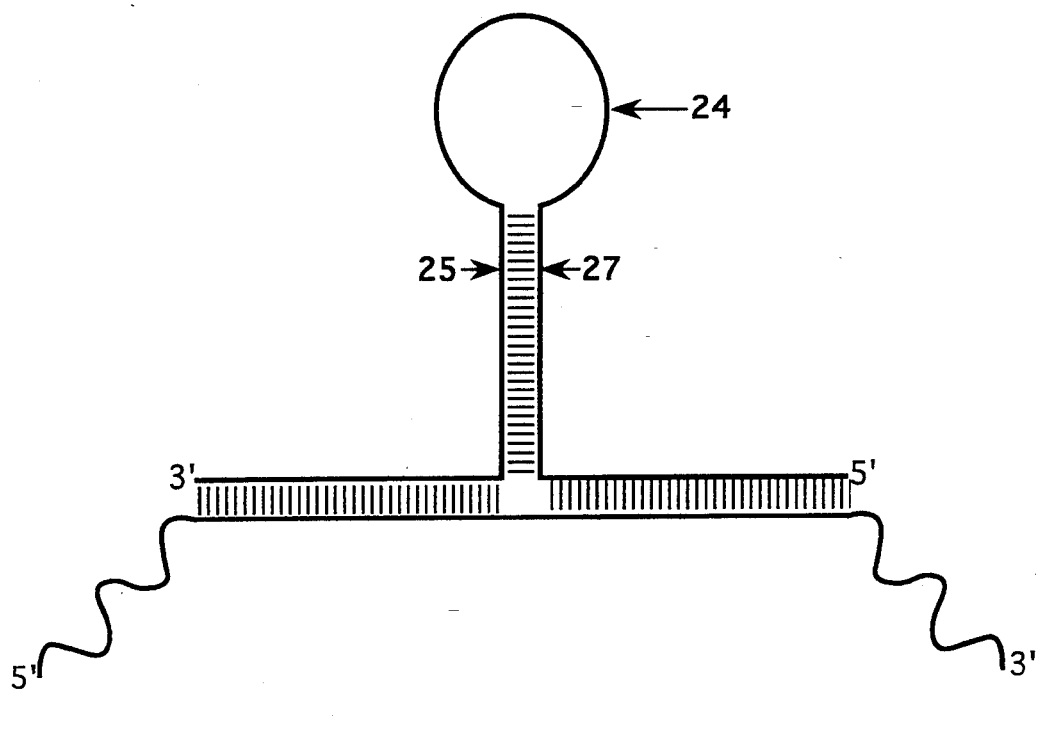
Figure 4B:
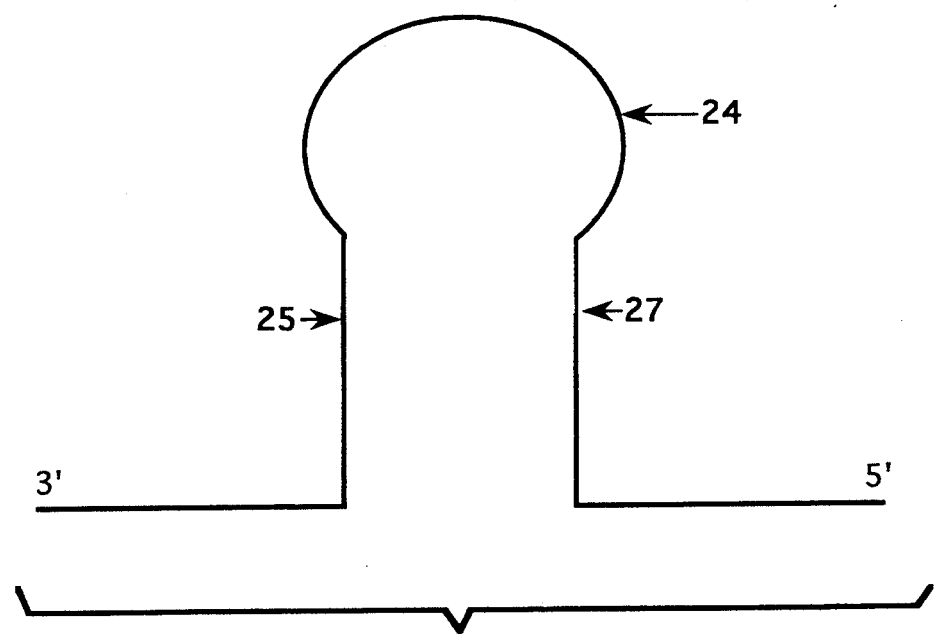

Another configuration of branched nucleic acid probe used for the detection of target nucleic acids is shown schematically in FIGS. 4A and 4B. In this configuration the probe consists of a single nucleic acid strand. The desired characteristics are the same as those described for the design shown in FIG. 1, but now the 2 strands of the probe are connected and therefore become 1 strand. A segment 24 connecting the two halves of the probe can be nucleotide or non-nucleotide in nature, and should be of a length that yields the desired probe characteristics described above. When utilizing the HPA format at 60° C., the preferred length of the complementary, unmodified arms 25, 27 in this configuration is somewhat shorter than described for the design shown in FIG. 1 due to the intramolecular nature of the interaction. Therefore, the preferred arm length is approximately 4 to 16 bases. As mentioned above, other environmental conditions would potentially lead to a different size range; this is easily determined experimentally by standard procedures.

EXAMPLE 3

Figure 5A:
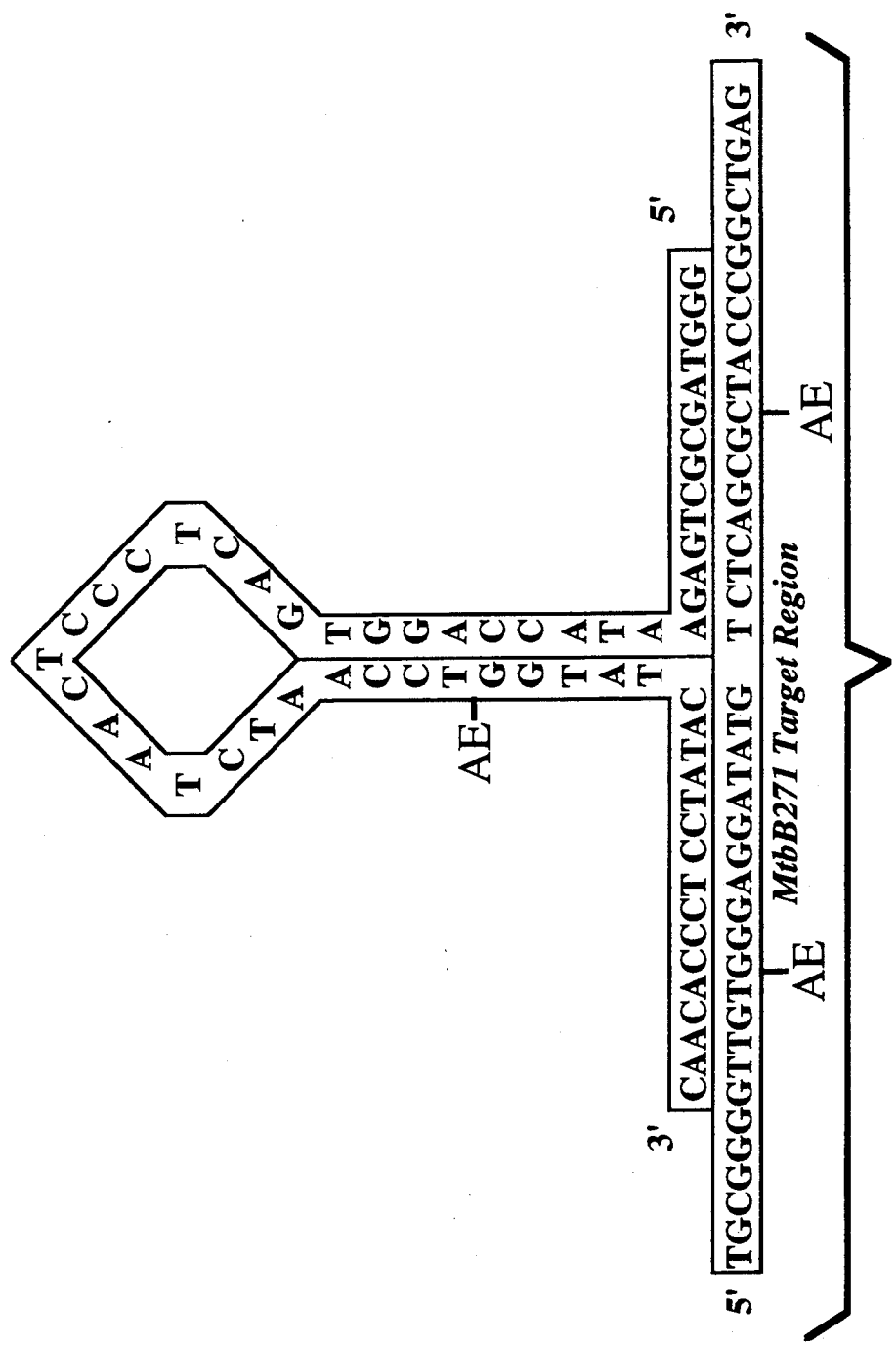
Figure 5B:
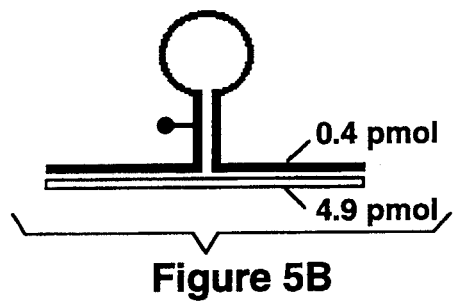
Figure 5E:
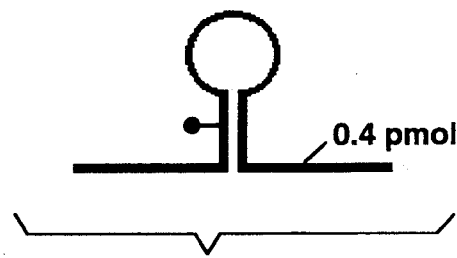
Figure 5C:
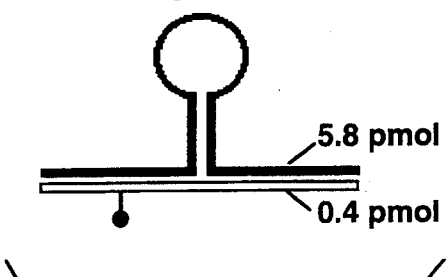
Figure 5F:
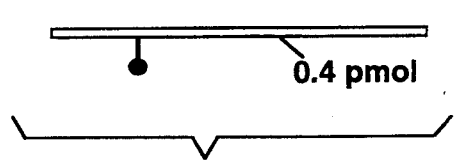
Figure 5D:
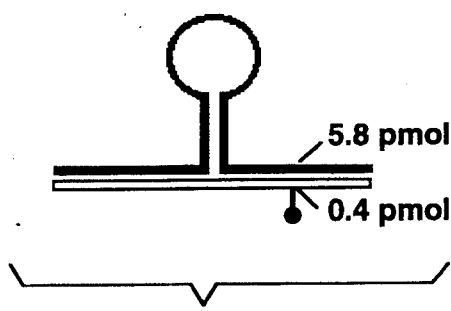
Figure 5G:
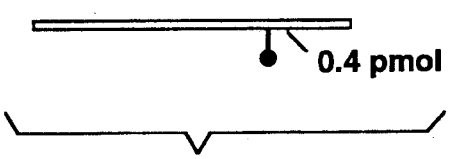

An example of the general structure shown in FIG. 4 is shown in FIG. 5A. The target strand is a synthetic DNA oligomer 43 bases in length with a sequence corresponding to a region of the 23S rRNA subunit of *Mycobacterium tuberculosis*. All oligomers were synthesized and AE-labeled as described in Example 1 above. The branched nucleic acid probe forms a 3-way junction with the target strand as shown in FIG. 5A. A single AE is covalently tethered to the probe between a T and an G residue as shown. An AE was also placed in the target strand at one of the two locations indicated in certain analyses as described below.

Hybridization characteristics of the structures depicted in FIGS. 5B–5G were evaluated using DH and Tm analysis protocols described in Example 1; the amounts of each component used in the respective annealing reactions are listed in FIGS. 5B–5G. The following results were obtained:

| Sample | Hydrolysis Half-life | | D.H. Ratio |
| --- | --- | --- | --- |
|  | Hybrid | Control |  |
| 1 | 5.8 | 1.2 | 4.8 |
| 2 | 10.2 | 0.32 | 31.9 |
| 3 | 8.1 | 0.56 | 14.5 |

These data demonstrate that the duplex formed between arm regions is more stable in the presence of target than the absence of target, as revealed by the increased AE stability. The relative difference in stability is large enough to be used to clearly detect the presence of target nucleic acid, but is not as great as that seen in either Example 1 or 2. Comparing the control hydrolysis rates of samples 1, 2 and 3, it is clear that the arms are interacting slightly under the operating conditions of this experiment. This interaction can be essentially eliminated by optimizing the operating conditions (e.g., higher operating temperature, inosine residues included in the arm regions, or phosphorothioate linkages included in the arm regions). This improves discrimination between the target present and target absent cases.

Other configurations of branched nucleic acid probes used for the detection of target nucleic acids are shown schematically in FIGS. 6A–6H. In these configurations the probe consists of three or more nucleic acid strands which form one or more nucleic acid junctions with the target nucleic acid. As above, such structures can be designed within a single nucleic acid molecule. Virtually any combination of junctions is possible as long as the arm regions form a stable duplex only in the presence of target (the possibility of some of the arm regions forming a stable duplex even in the absence of target will be discussed later). The guidelines for designing such a system are essentially the same as those described above for the configuration shown in FIG. 1. In the case of four way junctions (or even higher order junctions), some of the strands of the probe will contain only arm regions and no target specific regions. Since the sequence(s) of the strand(s) that contains only arm regions is independent of target sequence, this sequence(s) can be used in combination with a variety of specific probe strands for detection of a variety of target sites. This "universal detection" approach has several advantages, including the ability to use very few (or even only one) AE-labeled universal detection oligomer for the detection of all target sequences (this greatly minimizes design and synthesis time, therefore minimizing cost) and freedom to select the sequence that yields optimal differential hydrolysis, completely independent of target sequence.

As described above, AE can be placed in some or all of the arm regions as well as some or all of the probe regions. One advantage of this configuration is that there are many sites for AE, thus greatly increasing the label amplification potential of the assay. In one particular usage, the sequence around the AE site can be the same for each arm region, leading to uniformity of AE hydrolysis characteristics (AE hydrolysis rates are sequence dependent) and improving overall precision of the assay. The lengths of the probe regions can be manipulated to achieve certain assay performance goals. For instance, cross-reaction with closely related targets can be minimized by adjusting the lengths of the various probe segments. As an example, in FIGS. 6A, 6B, and 6C, probe regions 30, 32 of probe strands 1 and 3 can be relatively long and therefore form stable duplexes with target and even closely related non-target nucleic acids that possess homologous sequences in these regions. Probe region 34 of probe strand 2 can be relatively short, and span a region that contains one or more mismatches 36 to non-target nucleic acids. This probe segment will form a stable duplex with perfectly matched target, but by virtue of its relative shortness will not form a stable duplex with mismatched targets.

The above examples show three way junctions between an arm and two target regions. Four way junctions can be created with three probes (although they may be formed is a single molecule) as shown in FIGS. 6E and 6F with separate arm regions (labelled A) and probe regions (P). Similar examples are shown in FIGS. 6H and 6G.

EXAMPLE 4

Figure 6A:
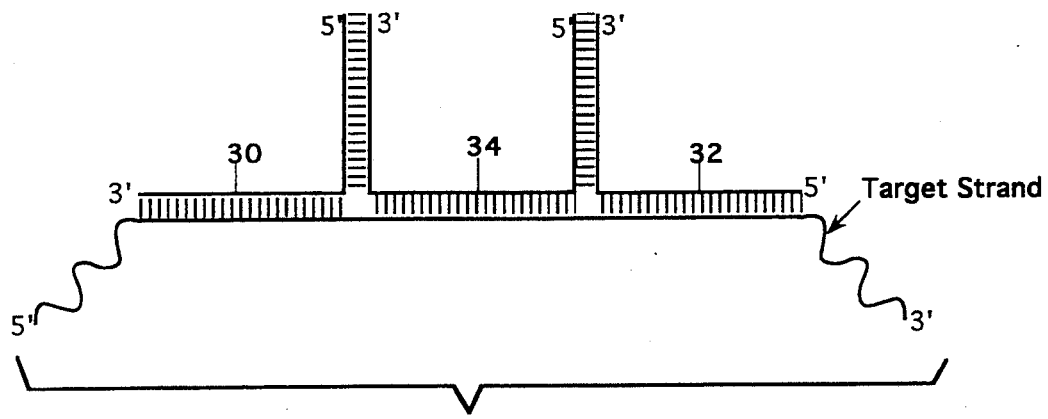
Figure 6B:
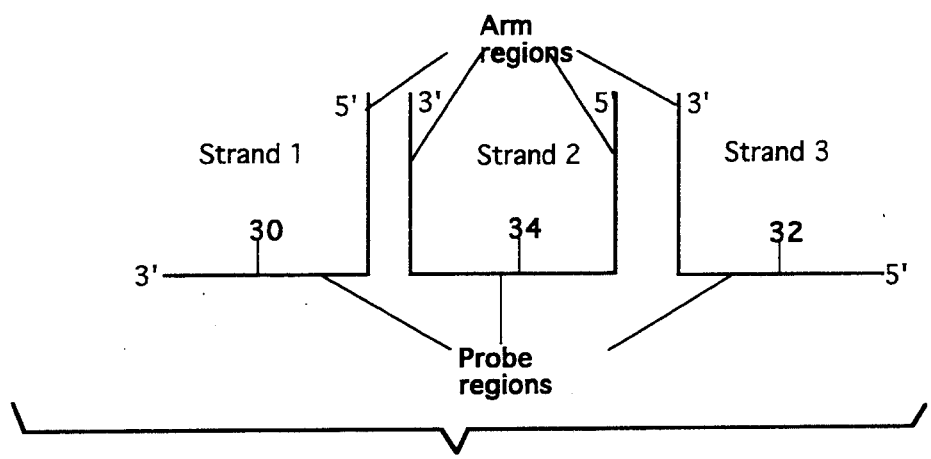
Figure 6C:
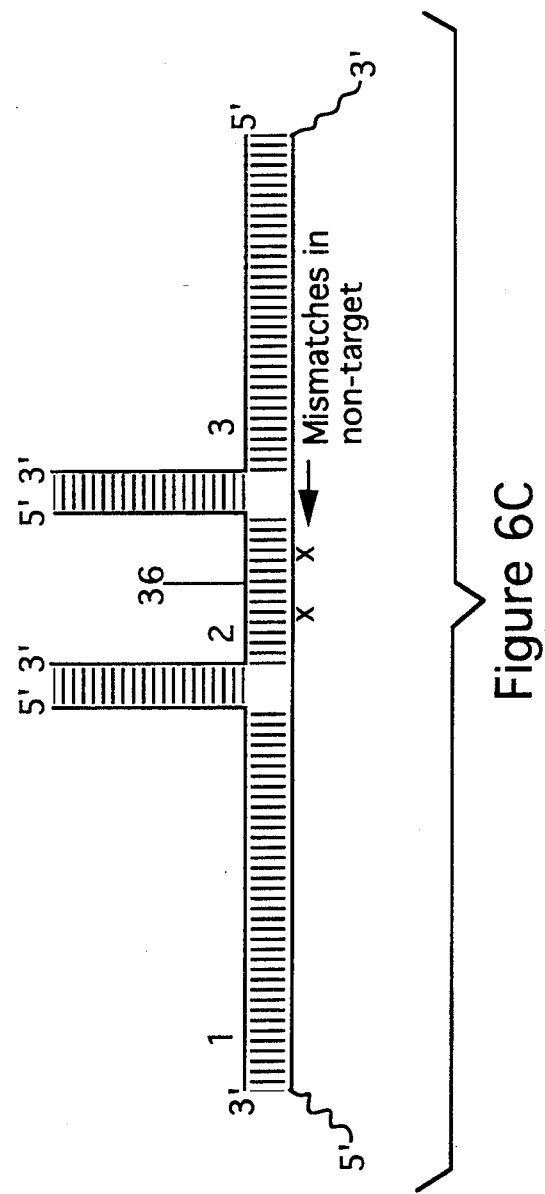
Figure 6D:
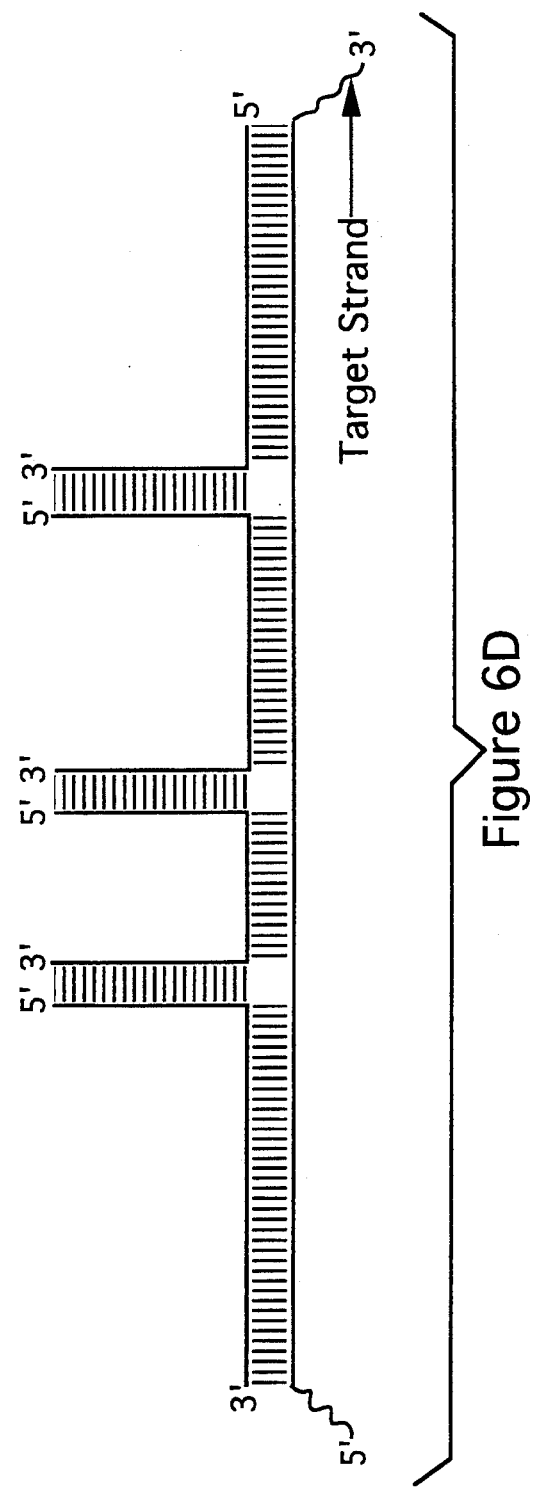
Figure 6E:
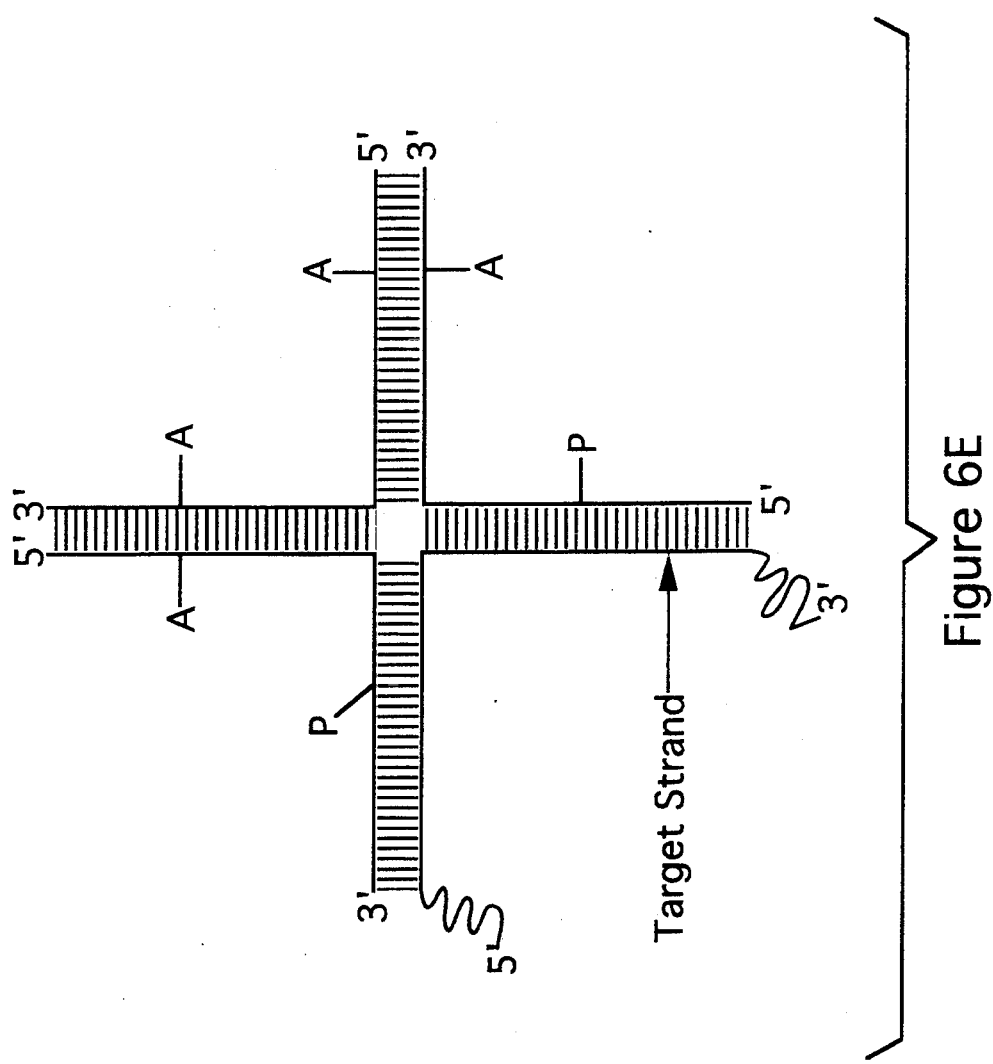
Figure 6G:
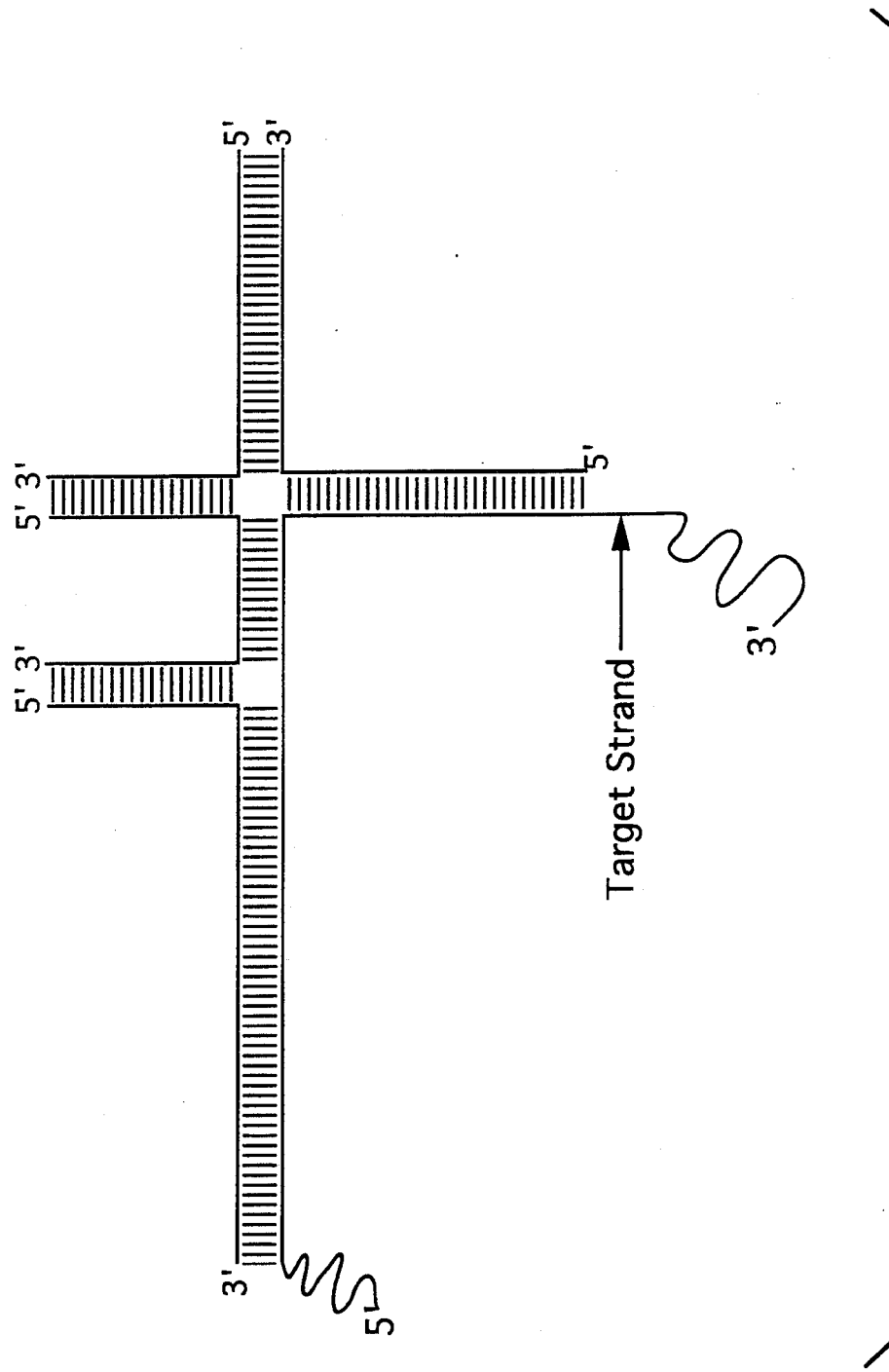
Figure 6H:
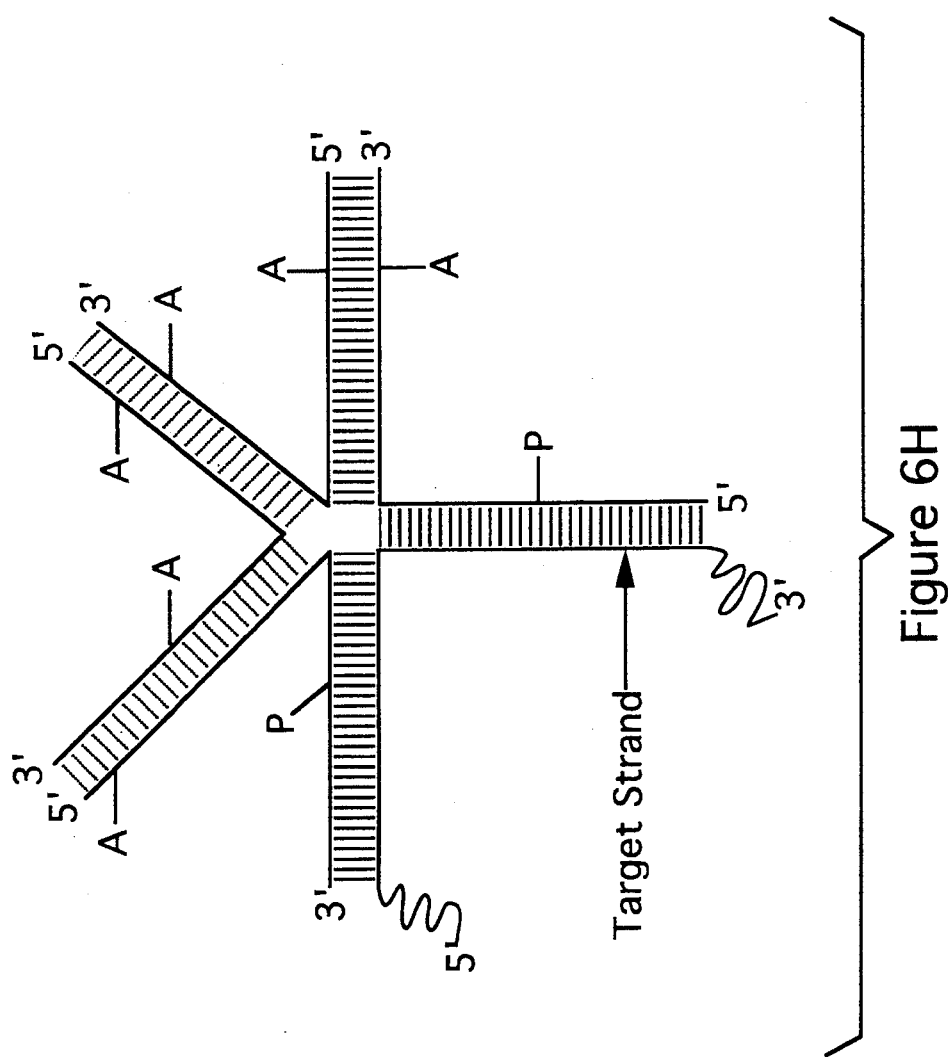
Figure 7:
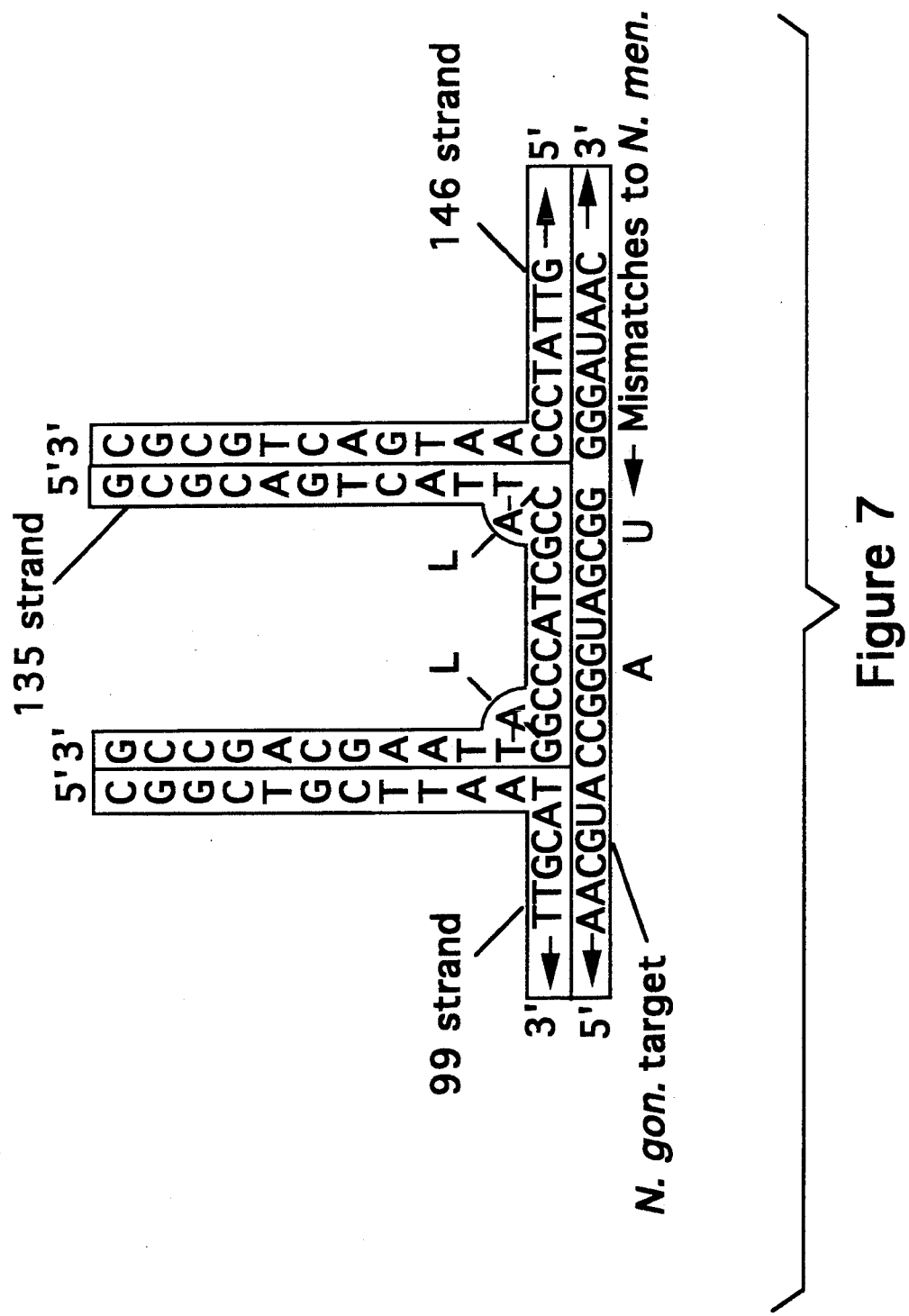

A specific example of the general configuration shown in FIG. 6A is shown in FIG. 7. The probes are labelled 99 strand, 135 strand and 146 strand. As in Example 2, ribosomal RNA (rRNA) from *Neisseria gonorrhoeae* is the target nucleic acid. All oligomers were synthesized and AE-labeled as described in Example 1 above. Two basic designs were evaluated, both containing three probe strands that form two three-way nucleic acid junctions with the target strand. The only difference between the two designs is that one contains loop-out (L) bases at the junctions as indicated in FIG. 7. (More loop bases can be included in probes of this invention if desired; as can non-nucleotide bases. In addition, probes may be formed which create a non-fixed, or mobile, junction.)

A variety of linker-arm placements were evaluated, as indicated below. Furthermore, the exactly complementary target nucleic acid (*N. gonorrhoeae*) as well as a potentially cross-reacting target nucleic acid with 2 mismatches (*N. meninqitidis*) were evaluated.

Hybridization characteristics of the different regions were evaluated using differential hydrolysis and Tm analyses as described in Example 1 with the following specific conditions: Structures 1–18 represented schematically in FIG. 8 were analyzed always using 0.6 pmol of the target strand, 0.1 pmol of AE-labeled probe strands, and 2 pmol of unlabeled probe strands; in samples 10–12 the target was *N. meningitidis*; in all the other samples, the target was *N. gonorrhoeae*; samples 1, 2, 4–6, 10, 11, 13, 14, 16 and 17 contained loop-out bases as shown in FIG. 7; the remaining samples did not contain loop-out bases. The resulting data are represented in tabular form in FIG. 8.

These data demonstrate that multiple arm regions can form in the presence of target, and only in the presence of target. Furthermore, multiple AE labels can be used in a single design, thus providing label amplification. Also, these structures can form with and without the loop-out bases shown in FIG. 7.

Figure 8:
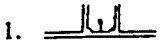
Figure 8:
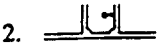
Figure 8:
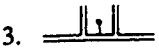
Figure 8:
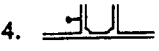
Figure 8:
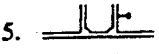
Figure 8:
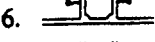
Figure 8:
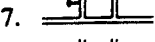
Figure 8:
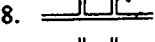
Figure 8:
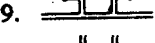
Figure 8:
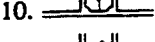
Figure 8:
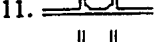
Figure 8:
Figure 8:
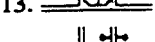
Figure 8:
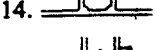
Figure 8:
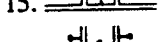
Figure 8:
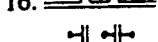
Figure 8:
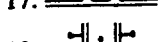
Figure 8:
Figure 9A:
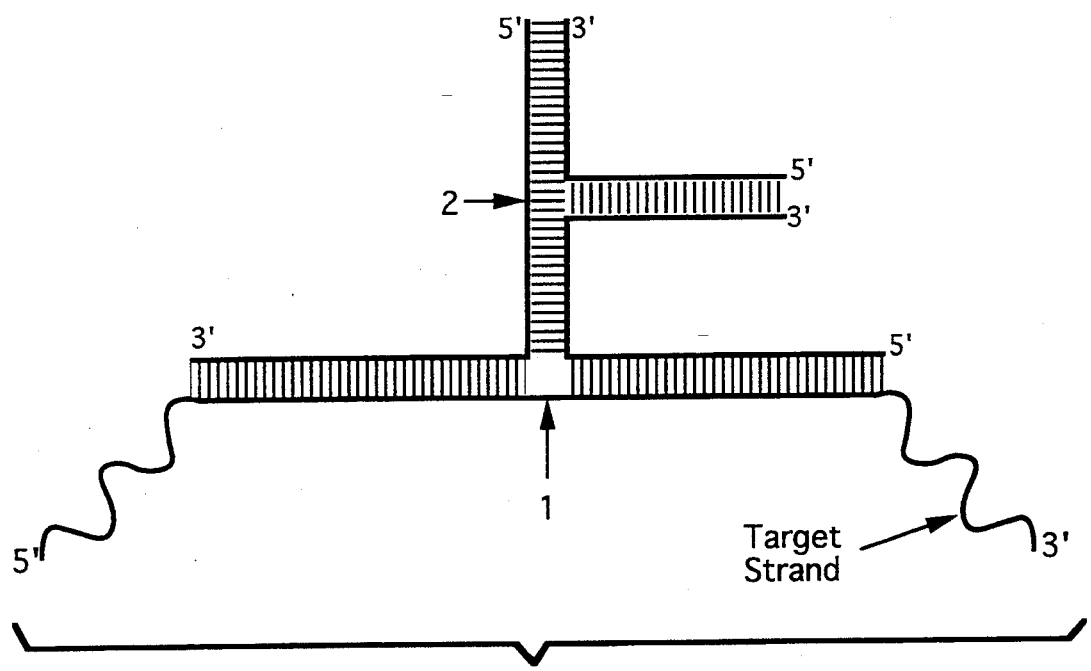
Figure 9B:
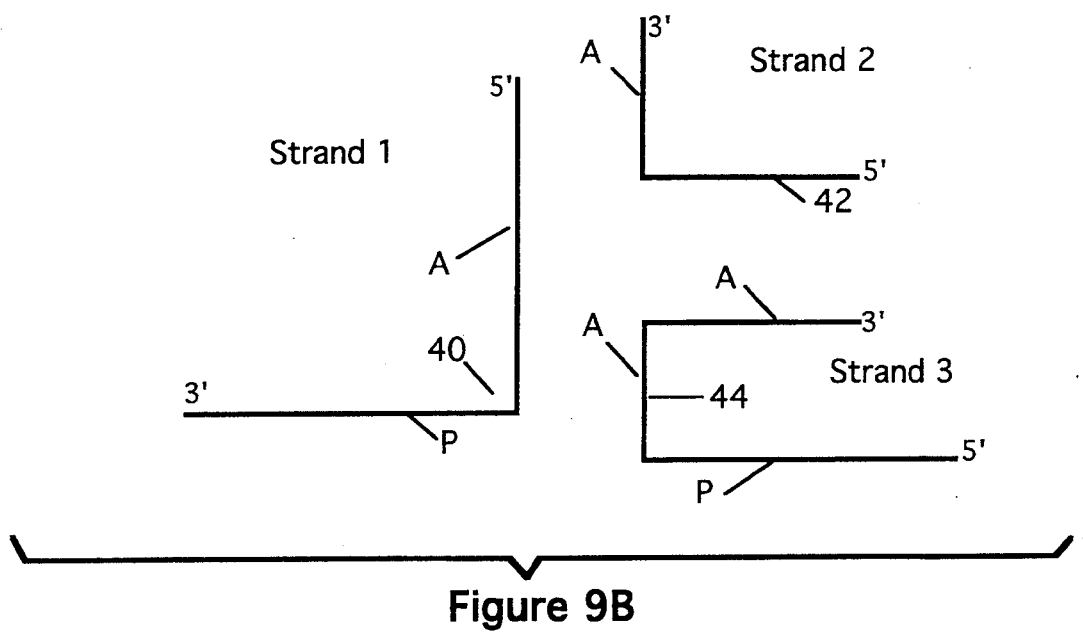
Figure 9C:
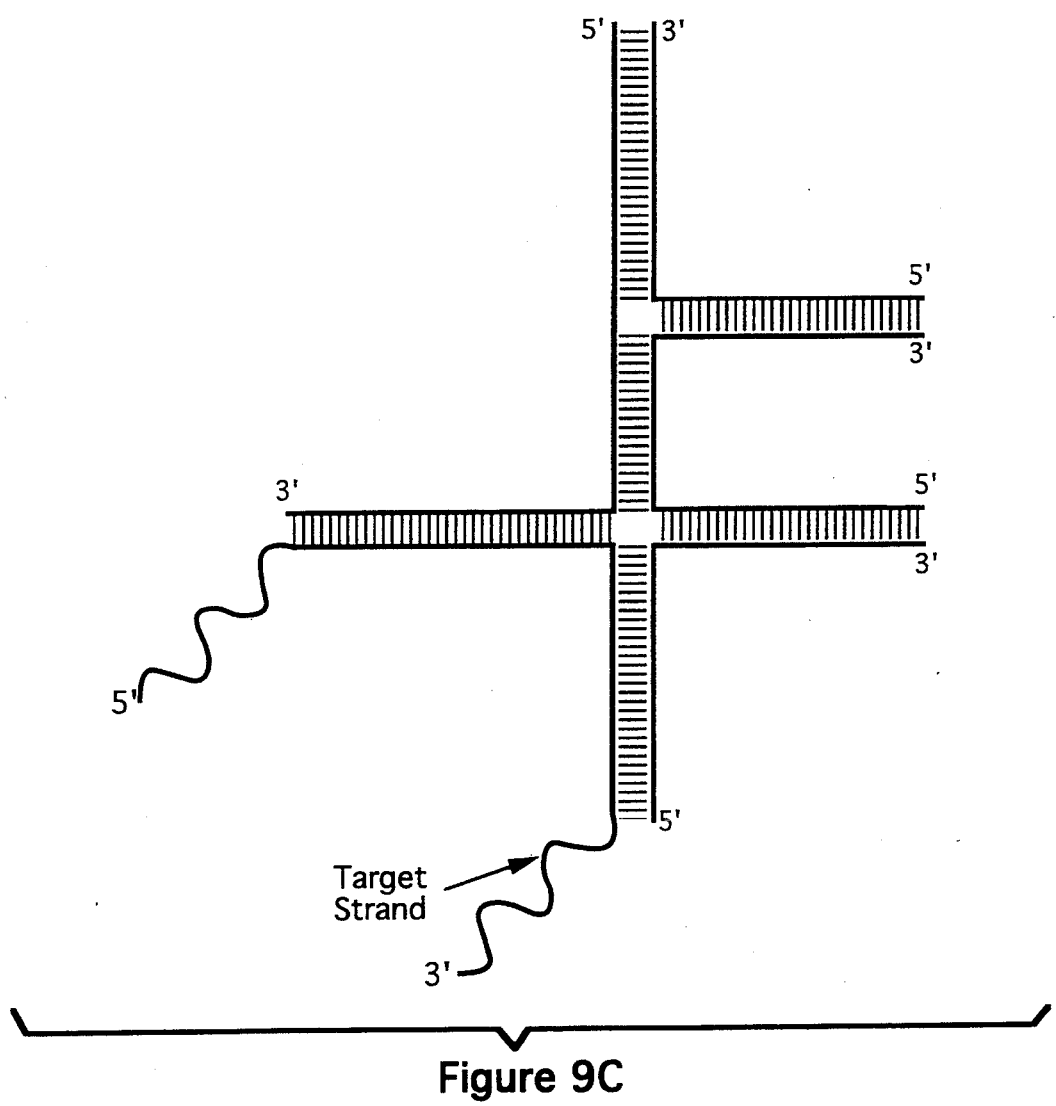
Figure 9D:
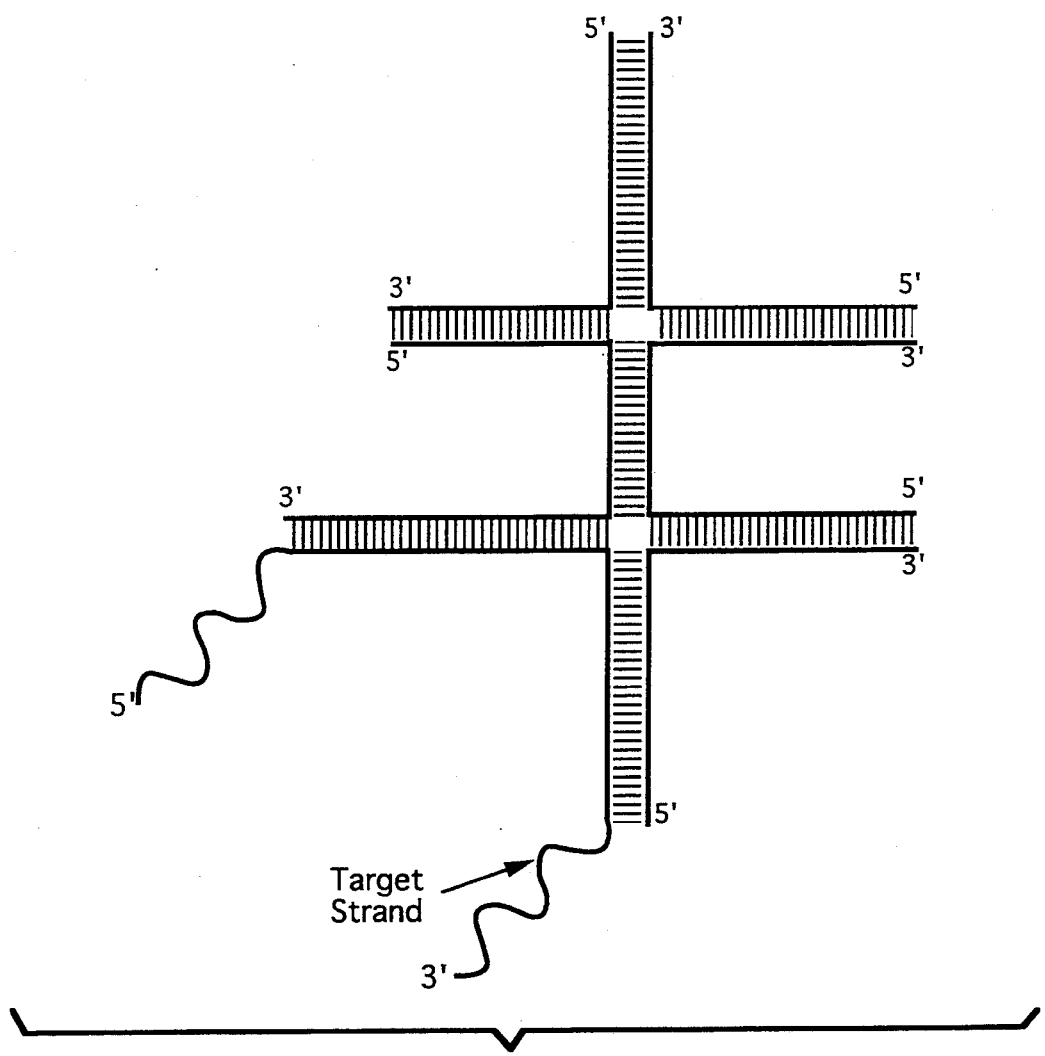
Figure 9E:
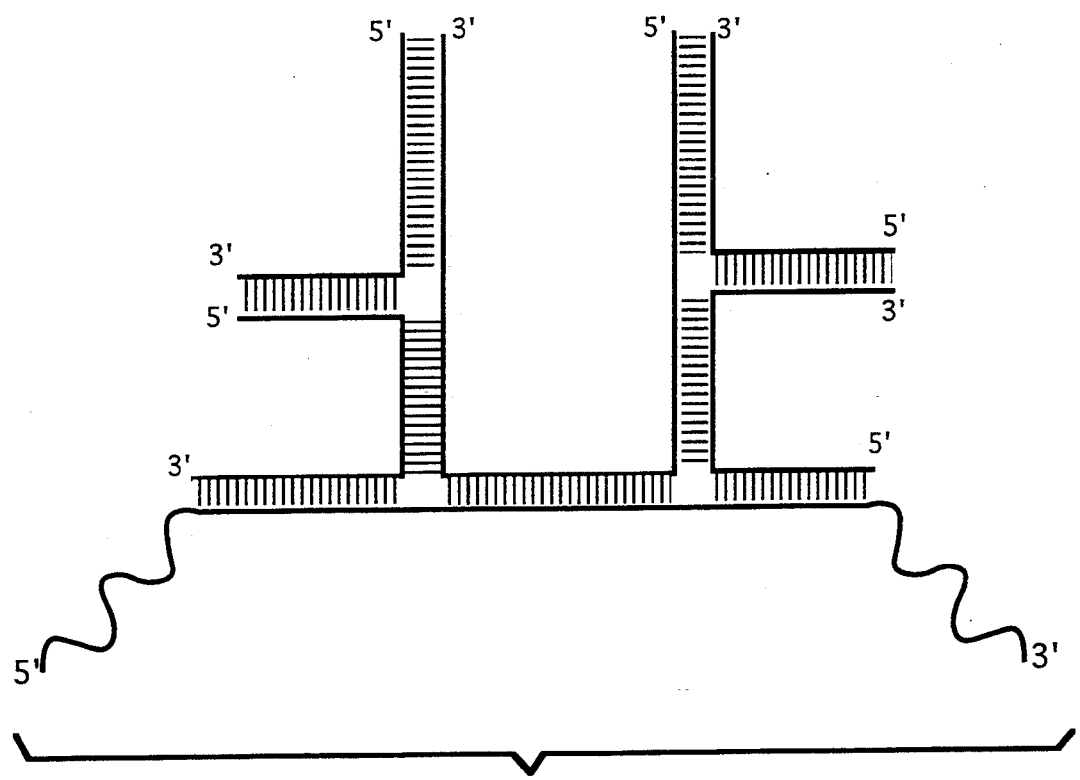
Figure 9F:
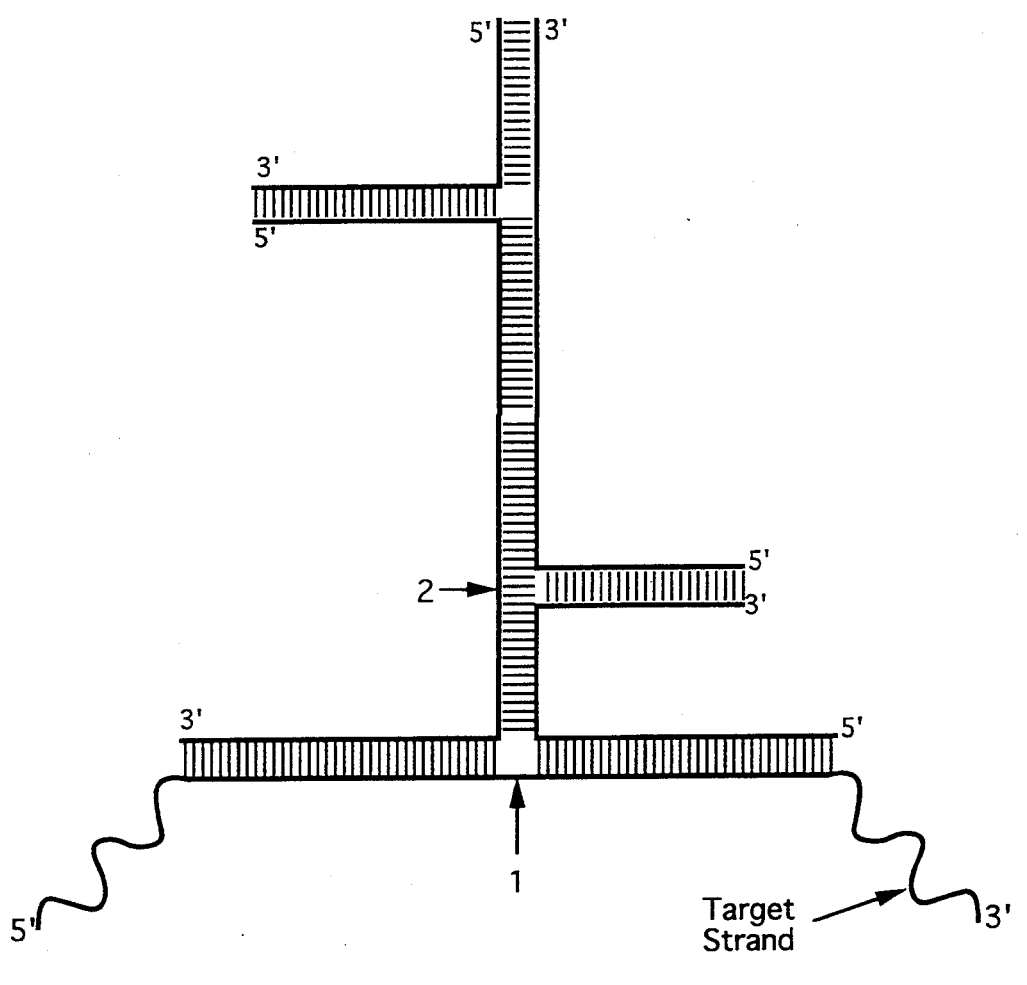

Selected structures from those shown in FIG. 8 were also evaluated for their ability to detect target nucleic acid (*N. qonorrhoeae*); cross-reaction with *N. meningitidis* was also tested. The general assay format was the same as that used in Example 3, with the following probe amounts: AE-labeled strands—0.1 pmol; non-labeled probe strands—2 pmol. The amounts of the target nucleic acids assayed and results are indicated below:

| Structure (See FIG. 8) | 10-2 μg N. gon. | 10-2 μg N. men. | No target control |
|---|---|---|---|
| 1 | 29,820 | 817 | 726 |
| 4 | 28,564 | 1302 | 683 |
| 5 | 15,540 | 1892 | 1127 |
| 16 | 90,000 | 1309 | 1211 |

These data demonstrate that the designs shown here are useful in detecting small amounts of nucleic acid in a full assay format. Furthermore, significant label amplification is demonstrated in structure 16, which contains 3 AE-labeled strands instead of 1 (as in probe structures 1, 4 and 5). Cross-reaction with the very closely related *N. meningitidis* RNA is minimal for structure 16; the slight cross-reaction seen in the other structures could be reduced to minimal levels by slightly increasing the operating temperature of the assay, which was selected as the optimal for structure 16.

Non-target Junction Probes

Another configuration of branched nucleic acid probe used for the detection of target nucleic acids is represented schematically in FIGS. 9A–9F. This configuration is very similar to the one just described above in that the probe consists of three or more nucleic acid strands, e.g., shown as 40, 42, 44, which form two or more nucleic acid junctions, but in this case one or more of the junctions are formed with the target nucleic acid (such as 1 in FIG. 9A) and one or more of the junctions are not associated with the target (such as junction 2 in FIG. 9A) but are still formed only in the presence of target. Virtually any combination of junctions is possible as long as the arm regions form a stable duplex only in the presence of target (the possibility of some of the arm regions forming a stable duplex even in the absence of target is discussed infra). Several examples of structures of this nature are represented schematically in FIGS. 9A–9F.

The guidelines for designing such a system are essentially the same as those for the configurations described above. The best combination of lengths and sequence of each region of each strand are typically determined experimentally by testing a variety of structures until the optimal combination is achieved. The design variables and the advantages of this configuration are essentially the same as those described above for the configuration represented by FIG. 6.

EXAMPLE 5

Figure 10:
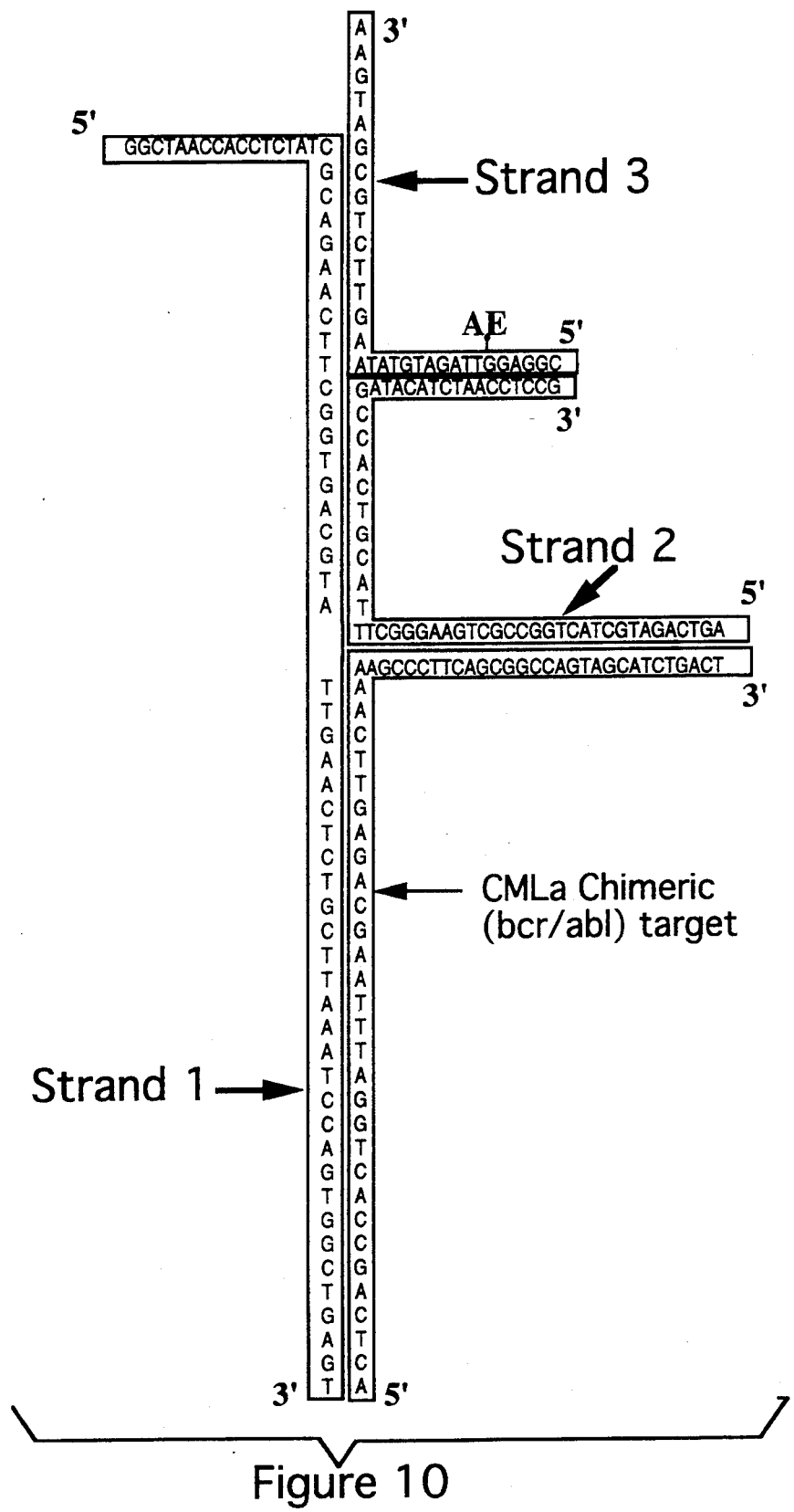

A specific example of the general configuration shown in FIG. 9 is shown in FIG. 10. The target is a synthetic DNA 60 mer (T) with a sequence corresponding to the major genetic translocation associated with chronic myelogenous leukemia (see Example 6 below). The probe consists of three strands, two of which form a 3-way junction with the target, and one of which forms a 3-way junction with the other two. This third strand contains only arm regions, and as such is a potential universal detection oligomer as discussed above. A single AE labeling site is detailed in this example, but AE can be placed in other regions as well.

To evaluate performance of this system, DH and Tm analyses were performed as described in Example 1 with the following specific conditions: target strand=0.5 pmol; unlabeled probe strands=2 pmol; AE-labeled probe strand=0.1 pmol; differential hydrolysis was performed at 50° C. The results were as follows:

| Half-life (min) | | | Tm (°C.) | |
| --- | --- | --- | --- | --- |
| Hybrid | Control | Ratio | Hybrid | Control |
| 45.7 | 0.97 | 47.1 | 59.8 | 46.2 |

These data demonstrate that the two junctions of this structure form only in the presence of target (at the operating temperature) as evidenced by the lack of protection against AE hydrolysis of the AE-labeled strand. This is a unique situation in which the hybridization of a strand that does not even come into contact with the target strand is completely target dependent. This clearly demonstrates the concept of the universal detection oligomer discussed above. This also demonstrates the ability to form multiple junctions in response to target.

Chimetic Probes

Figure 11A:
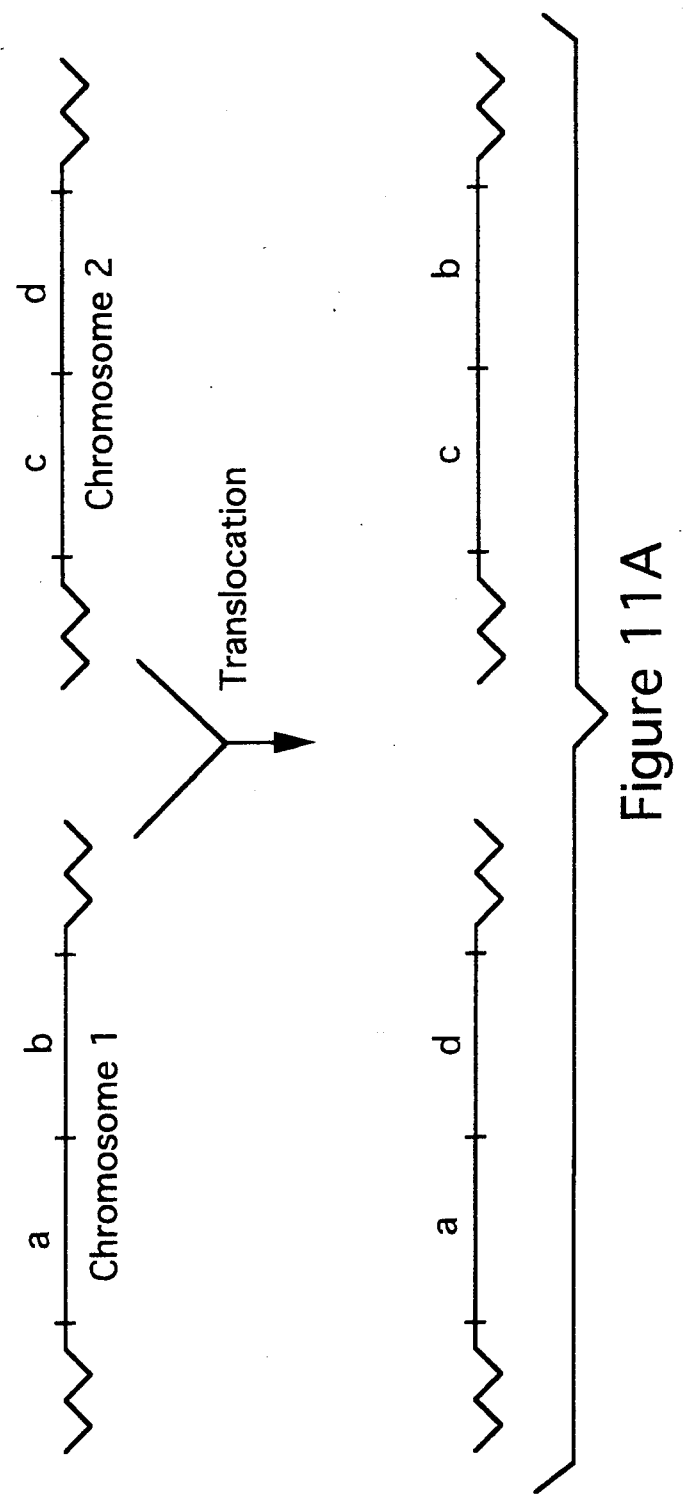
Figure 11B:
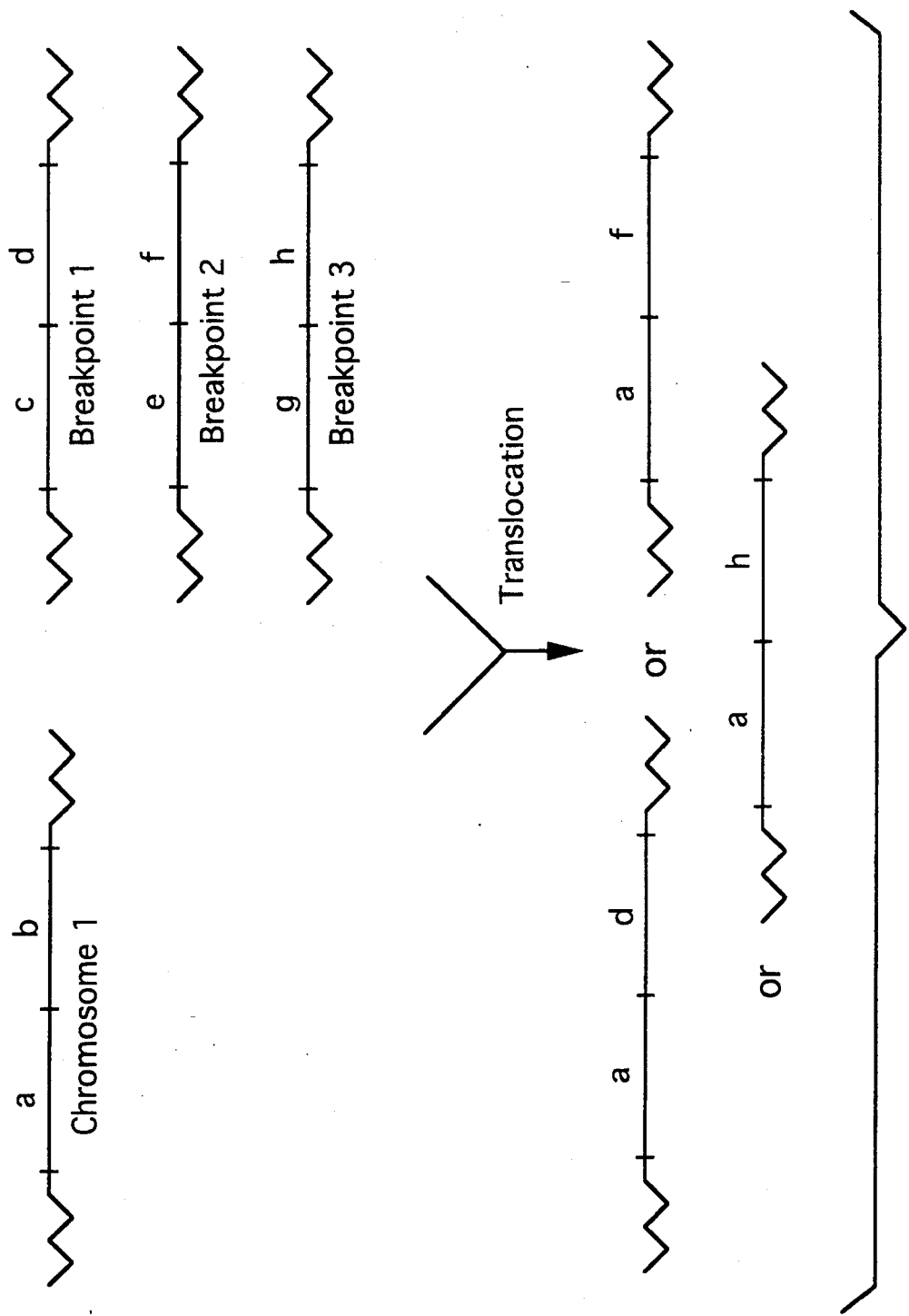
Figure 11C:
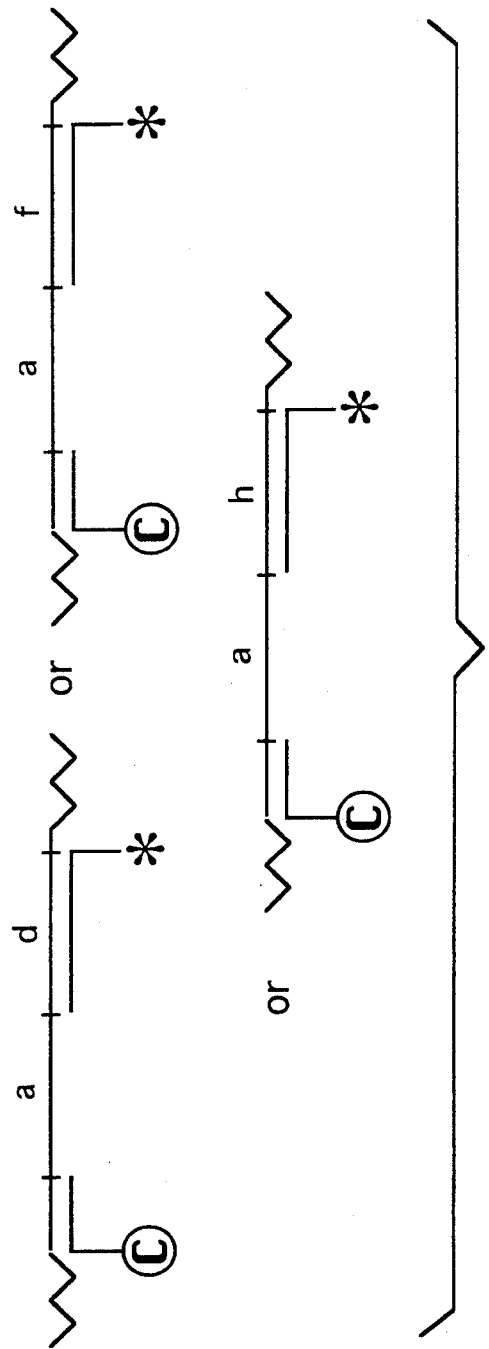
Figure 11D:
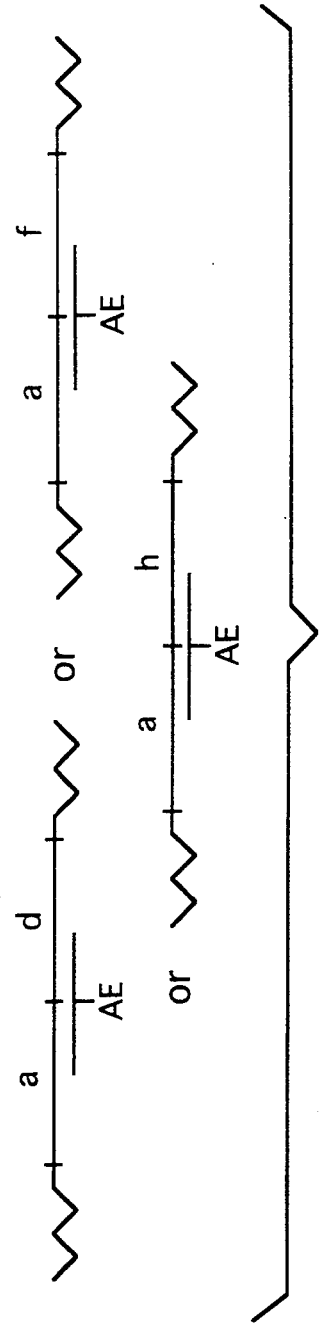
Figure 11E:
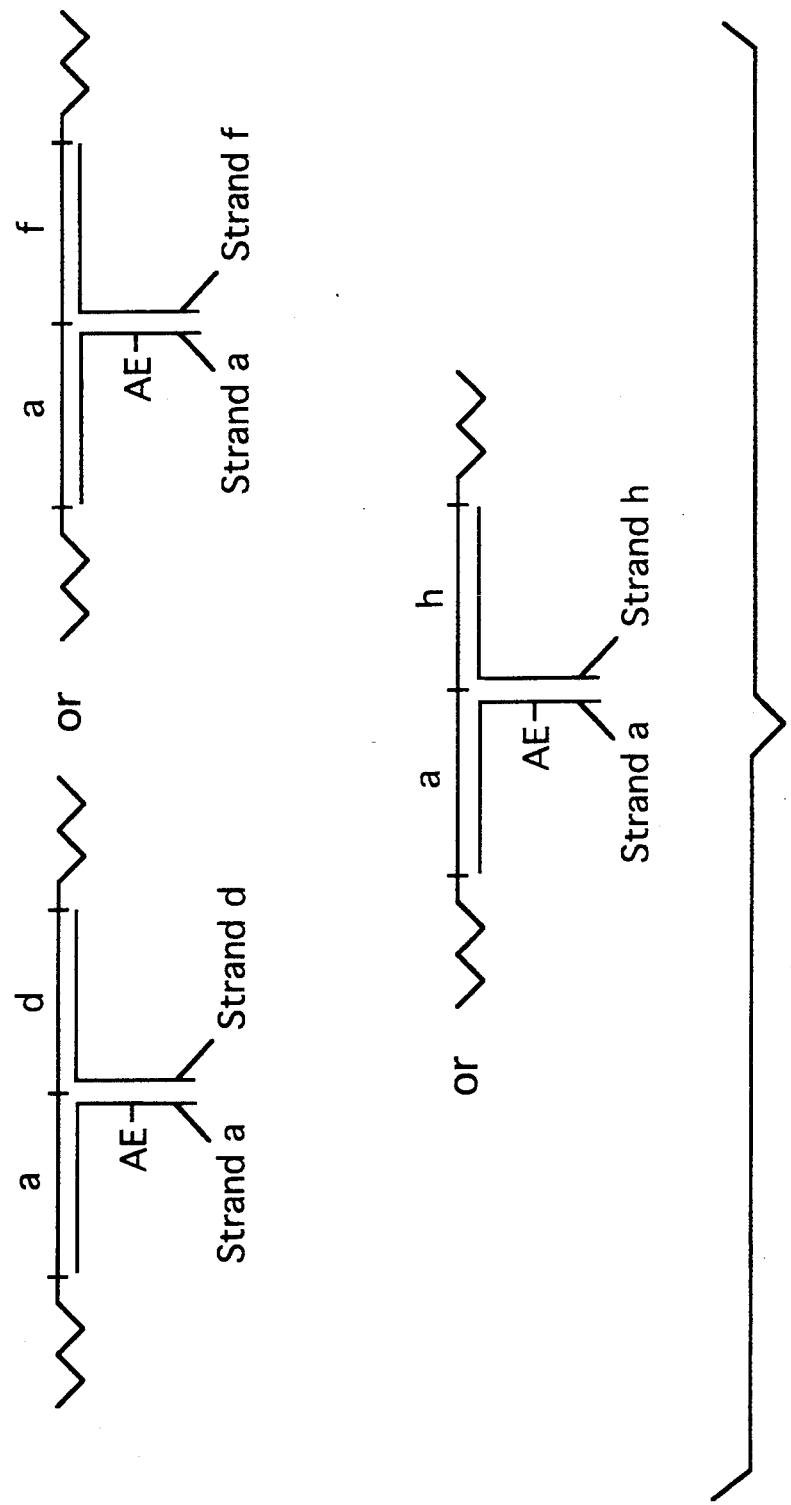
Figure 11F:
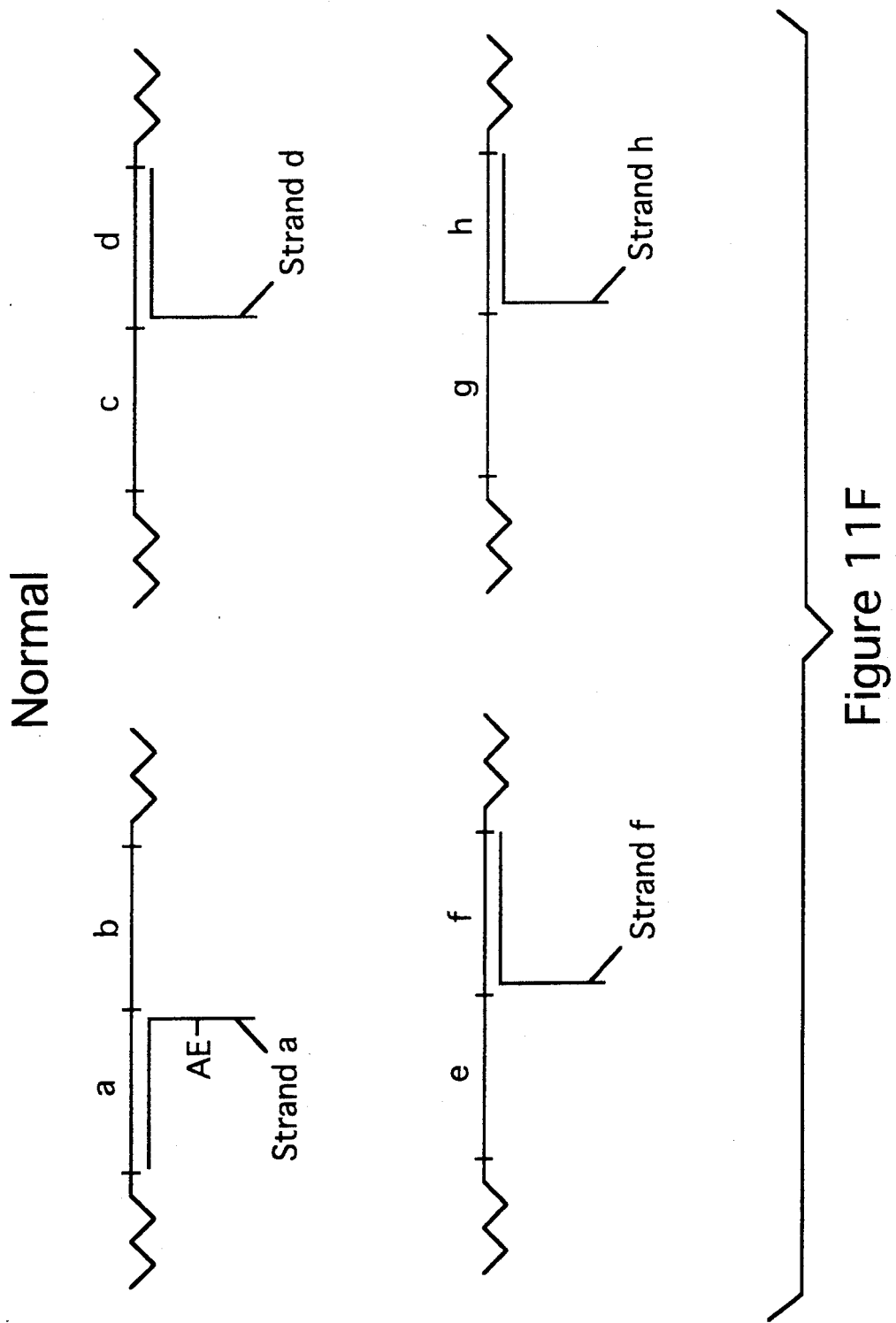

In another configuration, a branched nucleic acid probe can be used to detect a chimeric nucleic acid target. A chimeric nucleic acid is a nucleic acid made up two or more segments that each originate from different sources or are otherwise unique (e.g., the chimeric DNA only exists in a portion of a population of organisms) in some way. An example of such a chimeric target is the product of a genetic translocation as represented schematically in FIG. 11A. In this case, a segment of one chromosome is translocated onto another chromosome (and vice-versa in a reciprocal translocation), creating a chimeric DNA molecule (this may or may not result in a chimeric mRNA). This type of translocation can occur with multiple breakpoints (with one or both chromosomes), resulting in multiple chimeric DNA's. FIG. 11B represents a case in which 3 separate breakpoints on chromosome 2 reassociate with one breakpoint on chromosome 1.

Chimetic targets of this kind can be detected in a number of ways, examples of which are given in FIGS. 11C–11F. Method 1 (FIG. 11C) is a sandwich assay that requires a physical separation step. This method utilizes a capture probe specific for chromosome 1 (this capture probe is labeled with a specific capture agent, C, which allows it to be specifically removed from solution; for example, C may be biotin and the specific capture support may be avidin agarose), and 3 separate detection oligomers (each labeled with a reporter group) specific for the three different translocated regions of chromosome 2.

Method 2 (FIG. 11D) is a homogeneous assay that utilizes an AE-labeled probe specific for each translocation product (this is accomplished by designing the probes to "bridge" the breakpoint junction).

Method 3 (FIG. 11E and 11F) utilizes the method of this invention, in which a branched nucleic acid structure is formed around the breakpoint junction (other structures are possible, such as those shown in previous FIGS. in this application). Strand a is universal for all translocation products, and strands d, f and h are specific for the corresponding translocation products. In this particular example, strand a is the only strand that is AE-labeled. This system has several advantages, including the following: it is homogeneous, not requiring the physical separation steps required in Method 1; it has a universal sequence for AE protection, leading to uniform differential hydrolysis characteristics for each target; it has only 1 AE-labeled strand, minimizing complexity and cost and lowering backgrounds; it is less sensitive to mismatches (which can occur in the breakpoint junction region) than Method 2 (see Example 7). The guidelines for designing such a system are essentially the same as those for the configuration described in FIG. 1 above.

EXAMPLE 6

Figure 12A:
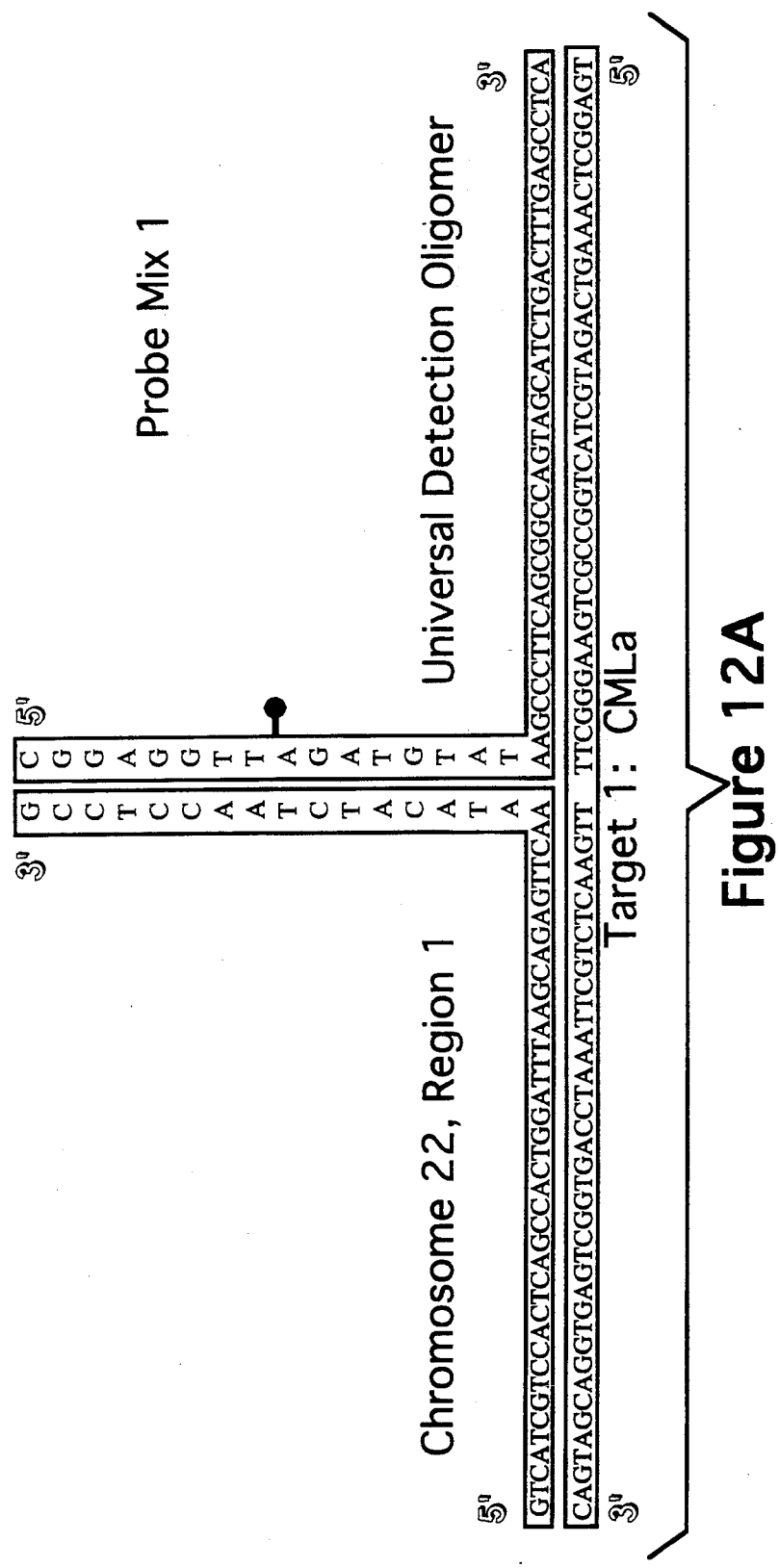
Figure 12B:
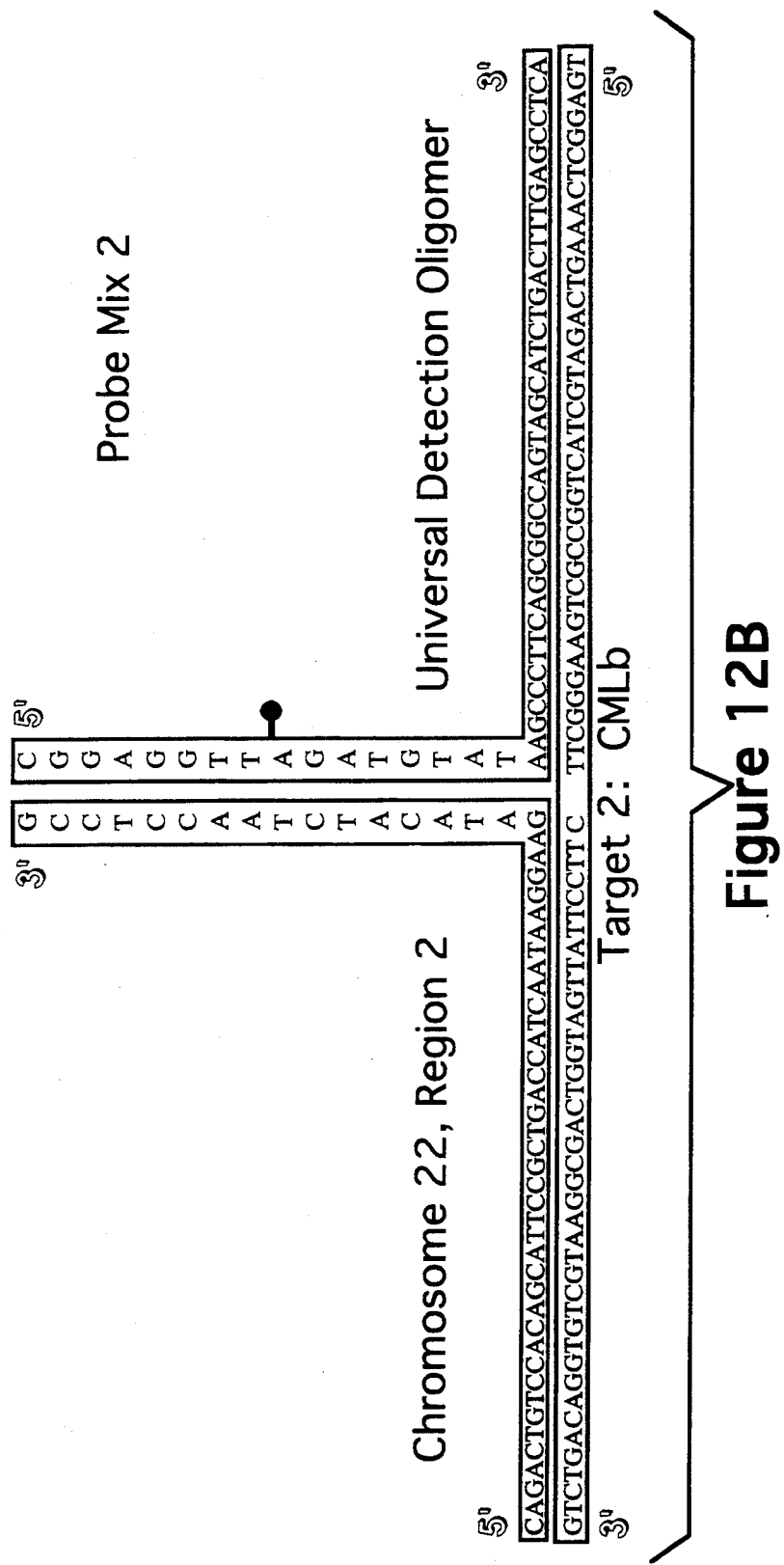
Figure 12C:
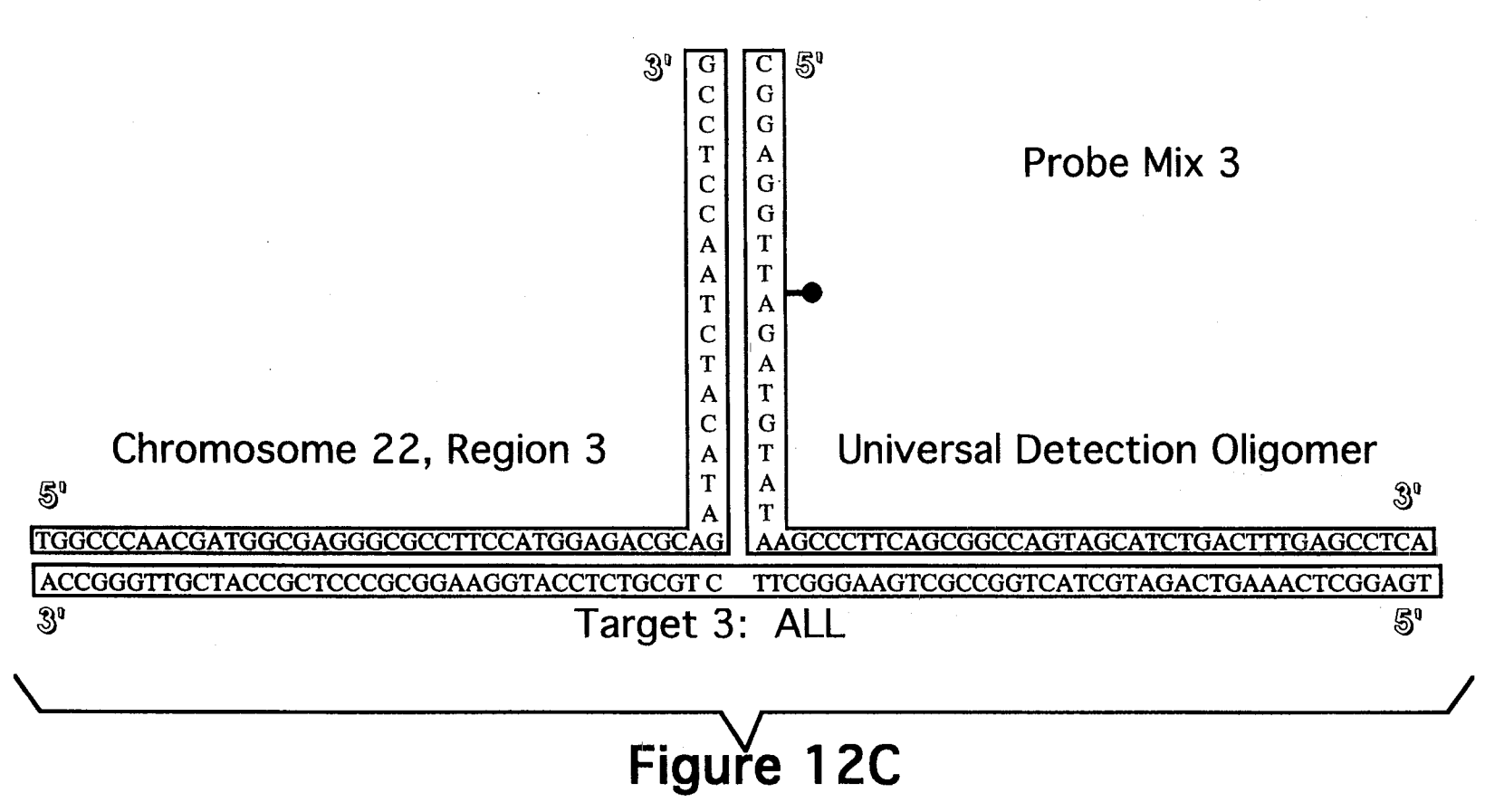

A specific example of the general configuration shown in FIGS. 11 is shown in FIGS. 12A–12C. The chimeric targets are synthetic DNA oligomers (80 mers) homologous to 3 different genetic translocations between a constant abl region of chromosome 22 and various regions of chromosome 9. Two are the most common translocations associated with chronic myelogenous leukemia (CML) and one is associated with acute lymphocytic leukemia (ALL). Each chimeric target contains an identical abl region, whereas all regions from chromosome 22 are different. An 80 mer corresponding to the normal abl gene (bridging the breakpoint 40 bases on either side) was also synthesized.

A single AE-labeled strand specific for the abl region was designed as shown in FIGS. 12A–12C. Three different strands were designed to contain a probe region specific for one of the translocated chromosome 22 regions as well as an arm region complementary to the arm region of the universal detection oligomer.

Performance of these 3 designs were first evaluated by measuring the differential hydrolysis rates and Tm's for each using the protocol described in Example 1 (target—0.5 pmol; AE-labeled probe strand—0.1 pmol; unlabeled probe strand—2 pmol). The results appear below:

| Structure | Half-life (min) | | DH Ratio | Tm (°C.) |
| --- | --- | --- | --- | --- |
| | Hybrid | Control | | |
| 1 | 18.3 | 0.636 | 28.8 | 71.5 |
| 2 | 18.4 | 0.640 | 28.8 | — |
| 3 | 18.6 | 0.640 | 29.1 | — |

Next, the ability of the 3 probe mixes to detect the appropriate target sequences (and not react with inappropriate target sequences) was evaluated. The assay format described in Example 4 was used (target—20 fmol; AE-labeled probe strand—0.1 pmol; unlabeled probe strand—2 pmol). The results appear below (average of quadruplicate reactions):

| Target | Probe mix 1 | Probe mix 2 | Probe mix 3 | AE-labeled strand only |
| --- | --- | --- | --- | --- |
| 1 | 202,187 | 1,354 | 1,265 | 889 |
| 2 | 2,950 | 167,614 | 1,343 | 1,107 |
| 3 | 1,307 | 2,319 | 131,670 | 729 |
| normal abl | 1,491 | 1,248 | 1,094 | 886 |
| no target | 624 | 614 | 506 | 451 |

The probe mixes detect only the correct chimeric targets and do not cross-react significantly with either of the other two chimeric targets or the normal abl sequence, thus demonstrating the utility of this configuration for the detection of chimeric nucleic acid targets, and the use of a single AE-labeled probe strand for the detection of multiple targets.

Mismatch Probes formed at three different temperatures (60°, 55° or 50° C.; see below). The results are as follows:

| Probe | AE-Strand | Target | NOM* | Temp | Half-life (min) Hybrid | Control | DH Ratio | |
|---|---|---|---|---|---|---|---|---|
| | | | | | | | | % Hyb |
| 1 | 1 | 1 | 0 | 60 | 4.3 | 0.56 | 7.7 | — |
| | 2 | | | | 10.2 | 0.82 | 12.4 | — |
| | 1 & 2 | | | | 7.4 | 0.75 | 9.8 | — |
| | 1 | 1 | 0 | 60 | 5.9 | 0.77 | 7.7 | 95 |
| | | 2 | 3 | | 7.7 | 0.77 | 10 | 59 |
| | | 3 | 4 | | 6.1 | 0.77 | 7.8 | 65 |
| | | 4 | 6 | | 10.0 | 0.77 | 13 | 6 |
| | 1 | 1 | 0 | 55 | 16.5 | 1.1 | 15 | 85 |
| | | 2 | 3 | | 13.9 | 1.1 | 12.6 | 79 |
| | | 3 | 4 | | 13.6 | 1.1 | 12.4 | 85 |
| | | 4 | 6 | | 9.8 | 1.1 | 8.9 | 57 |
| | 1 | 1 | 0 | 50 | 30.3 | 1.7 | 17.8 | 91 |
| | | 2 | 3 | | 41.6 | 1.7 | 24.5 | 76 |
| | | 3 | 4 | | 32.2 | 1.7 | 18.9 | 87 |
| | | 4 | 6 | | 17.8 | 1.7 | 10.5 | 82 |
| | | | | | | | | Tm(°C.) |
| 2 | 1 | 1 | 0 | 60 | 10.3 | 0.87 | 11.8 | 74 |
| | 2 | | | | 9.8 | 1.5 | 6.5 | 71 |
| | 1 & 2 | | | | 9.9 | 0.58 | 17 | 70 |
| 2§ | 1 & 2 | 1 | 0 | 60 | 9.3 | 0.66 | 14.1 | |
| | | 2 | 3 | | 9.6 | 0.66 | 14.6 | |
| | | 3 | 4 | | 9.5 | 0.66 | 14.4 | |
| | | 4 | 6 | | 7.2 | 0.66 | 10.9 | |

*Number of Mismatches.
DH Temperature (°C.).
§Separate experiment

In another configuration, a branched nucleic acid probe is used to detect a variety of targets with related but non-identical sequences. Typically, DNA probe-based assays are designed to detect a specific target and to not cross-react with closely related targets. In fact great effort has been expended to develop assays that will be sensitive to as little as one mismatch. However, there are cases when an assay needs to be relatively insensitive to mismatches. An example of such a case is the detection of viruses such as HIV, which display significant genomic variation.

EXAMPLE 7

Figure 13:
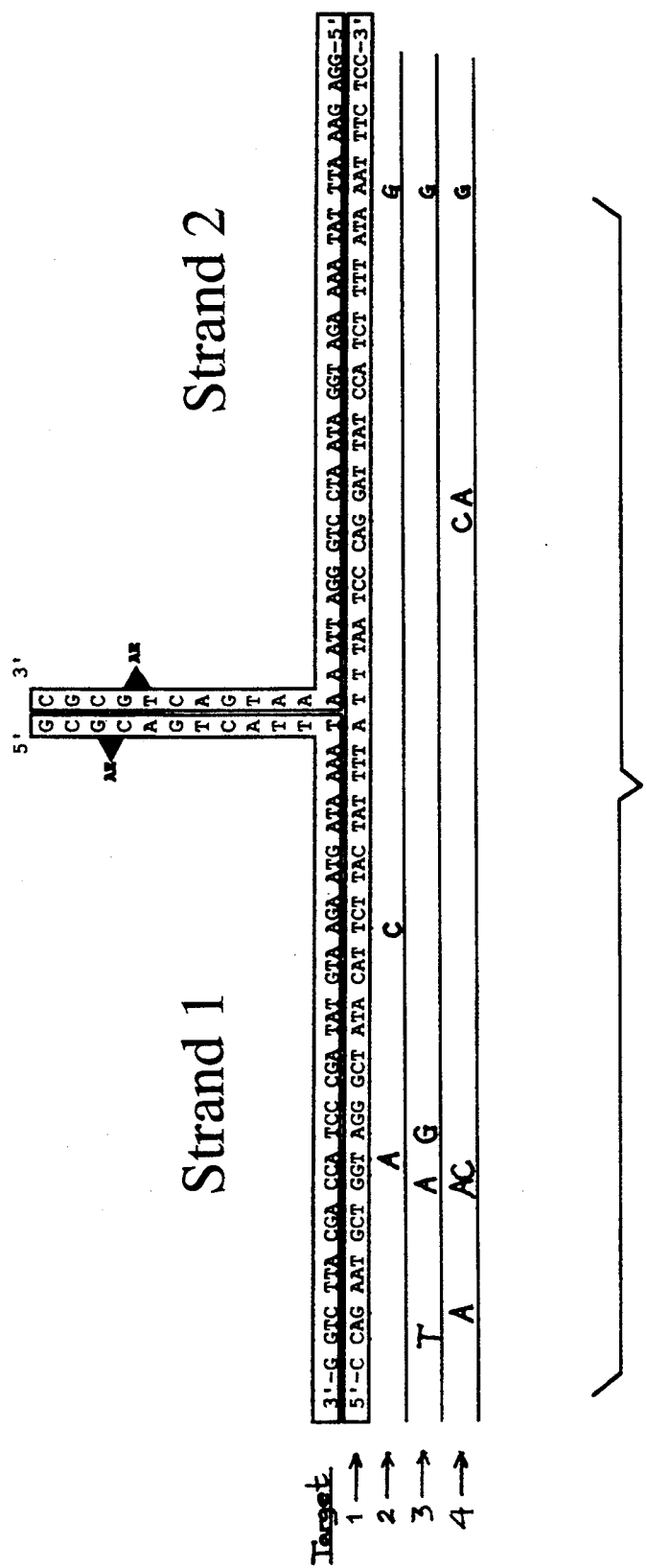
FIGS. 13 and 14 are specific examples of mismatched probes.
Figure 14:
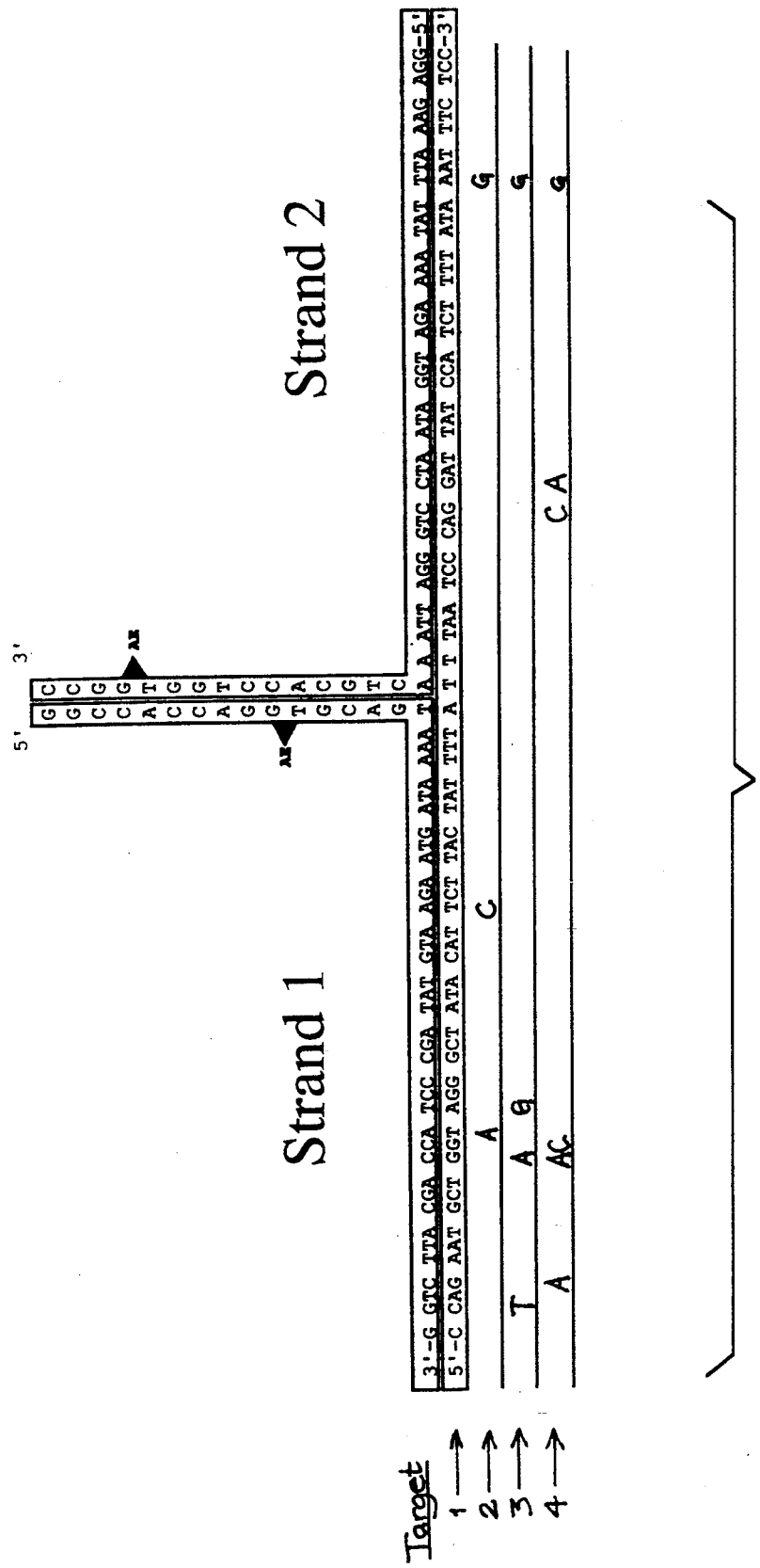

A specific example of the general configuration discussed above is shown in FIG. 13. The exact target strand is a synthetic DNA oligomer 78 bases in length with a sequence corresponding to a region of the gag gene in HIV-1. Other synthetic 78mers were also constructed to contain a variety of mismatches as shown in FIG. 13 (these sequences correspond to various HIV strains that have been isolated and sequenced). Two branched nucleic acid structures were evaluated, which have identical probe regions but different arm regions (see FIG. 14). The probe regions were designed to be very stable at the operating temperature, thus increasing the overall stability of the branched nucleic acid structure once formed with the target. The stability of each region, including the stability added by the arm regions (once hybridized), buffers against loss of stability in other regions caused by mismatches, thus decreasing the sensitivity of the overall structure to mismatches. All oligomers were synthesized and AE-labeled as described in Example 1 above.

Differential hydrolysis ratios and Tm's of these designs were determined using the general protocols given in Example 1 above with the following specific conditions: target strand—0.5 pmol; AE-labeled strand(s)—0.1 pmol; unlabeled strand—2 pmol; hybridizations and corresponding DH ratio analyses were per- These results demonstrate that the branched nucleic acid probes can tolerate 3 and 4 mismatches with little or no effect on performance characteristics, and can tolerate 6 mismatches with only a small decrease in performance characteristics. Therefore branched nucleic acid probes can be used in assay formats that require relative insensitivity to mismatches. Furthermore, these data again demonstrate the ability to include multiple AE's per probe design (i.e., label amplification).

Structure 2 was further evaluated by detecting decreasing amounts of the perfectly matched target (target 1) in a full format assay as described in Example 4 (strands 1 and 2 AE labeled, 0.1 pmol each strand used; target concentrations given below). The results are as follows:

| [Target] (fmol) | Signal (RLU) |
|---|---|
| 30 | 840172 |
| 10 | 339581 |
| 3 | 114496 |
| 1 | 35022 |
| 0.3 | 11175 |
| 0.1 | 3755 |

These data demonstrate that the branched nucleic acid probe shown here is capable of detecting small quantities of target nucleic acid in a full format assay.

Detection of Branch Duplex

The target-dependent formation of a duplex between complementary arm regions of a branched nucleic acid probe can be detected using techniques other than the AE-label/differential hydrolysis technique discussed above. Furthermore, this differential duplex formation can give rise to a wide variety of biological or the chemical properties which are target-dependent. The two-strand branched nucleic acid probe described in FIG. 1 will be used as a model to discuss some examples of these properties, including alternate modes of detection. However, it will be readily recognized that these properties are applicable to any number of different branched nucleic acid probe configurations as long as the basic criterion that the arm regions in question form a stable duplex only in the presence of target is met.

EXAMPLE 8

Restriction Endonuclease Cleavage

In one system (FIG. 15A), arm region duplex formation creates an active (double-stranded) restriction enzyme cleavage site (R) removed from the target strand. Cleavage at this site with a restriction endonuclease can be detected in a variety of ways. For example, one or both of the strands can be labeled with $^{32}P$, and cleavage products can be detected using gel electrophoresis or other separation techniques. Alternatively, one or both of the strands can be labeled on one side of the cleavage site with a capture agent (such as biotin), and the other side of the cleavage site can be labeled with a reporter group (e.g., $^{32}P$, AE). After cleavage, the strands are captured (with avidin agarose, for example), and reporter group associated with capture support indicates no cleavage, whereas reporter group associated with the supernatant indicates cleavage. Alternatively, a detection probe can be designed to react with the uncleaved strand but not the cleaved strand. This can be performed in a homogeneous or a separation assay (the homogeneous format is depicted in FIG. 15B). In one particular aspect of this system, the cleavage site is designed to be close to the base (i.e., the portion near the junction) of the arm region duplex. Upon cleavage with the restriction nuclease, the arm regions are almost entirely removed from the 3-way branched nucleic acid structure, thus reducing the stability of the overall structure. If the probe regions are designed to be stable only in the presence of intact arm duplex, once cleavage occurs the probe regions will melt off of the target. This will then allow uncleaved probe strands to hybridize with the target and start the process over again, thus increasing assay sensitivity by cycling multiple probes through a single target site.

EXAMPLE 9

DNA/RNA Polymerase Extensions

In another system (FIG. 15C), the arm regions are designed so as to create a site for extension by a polymerase. This filled-in region can be detected by first $^{32}P$ labeling the shorter strand and then detecting any extended primer strand using gel electrophoresis or other separation techniques. The filled-in sequence can also be detected using an AE-labeled probe specific for the extension product in a differential hydrolysis format. If a restriction site is included near the base of the arm region duplex, this system also has the potential for cycling as described above.

EXAMPLE 10

Amplification

In another system (FIG. 15D) fill-in with a polymerase creates an active T7 RNA promoter site. Subsequent to fill-in, T7 RNA polymerase will transcribe multiple copies of the template strand, thus yielding an amplification of detectable products and thus an increase in assay sensitivity. These strands can be detected, e.g., by incorporation of radiolabeled ribonucleotides and subsequent separation (e.g., by gel precipitation), or by differential hydrolysis of a complementary AE-labeled probe. If a restriction site is included near the base of the arm region duplex, this system also has the potential for cycling as described above. RNA transcripts are detected, e.g., with an AE-labelled probe.

EXAMPLE 11

Selective Degradation

In another system (FIG. 15E), one arm region is DNA and the other arm region (or portions thereof) is RNA. Formation of the arm duplex creates an active RNAse H cleavage site. Cleavage with RNAse H can be detected as described above for system 1. This system also has the potential for cycling as described above.

EXAMPLE 12

Chemical Cleavage

In another system (FIG. 15F), a chemical cleavage agent (X, such as Fe.EDTA or Cu.phenanthroline) specific for double-stranded nucleic acid is tethered to the arm region of one of the probe strands. When the arm region duplex is formed, cleavage of the nucleic acids in the immediate vicinity occurs (cleavage pattern is dependent on chemical cleaver and exact location and attachment chemistry). This cleavage can be detected as described above. This system also has the potential for cycling as described above.

Any other system that discriminates between single and double stranded nucleic acid is potentially applicable to the configuration generally described above, e.g., specific monoclonal antibodies for double stranded nucleic acid.

EXAMPLE 13

Figure 15A:
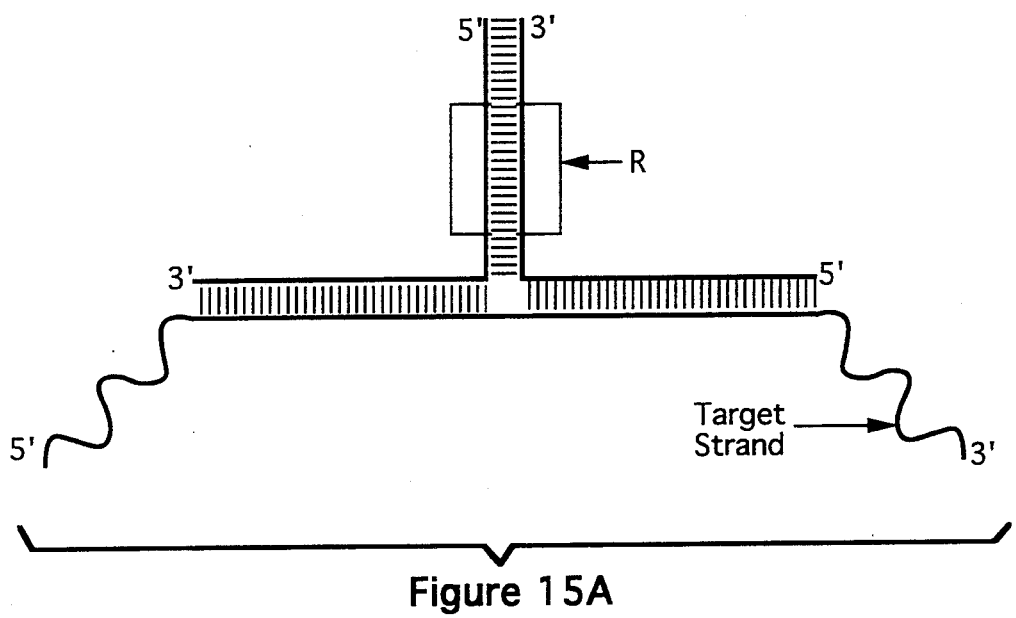
Figure 15B:
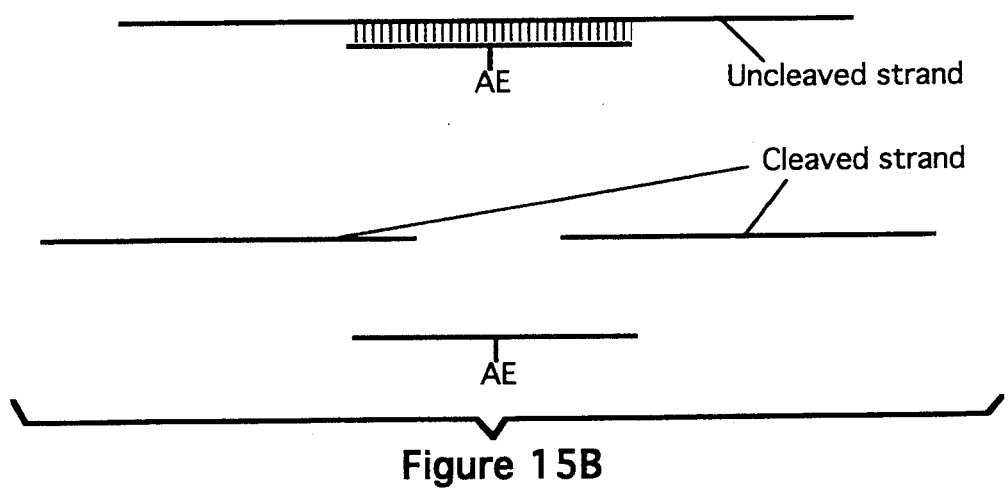
Figure 16:
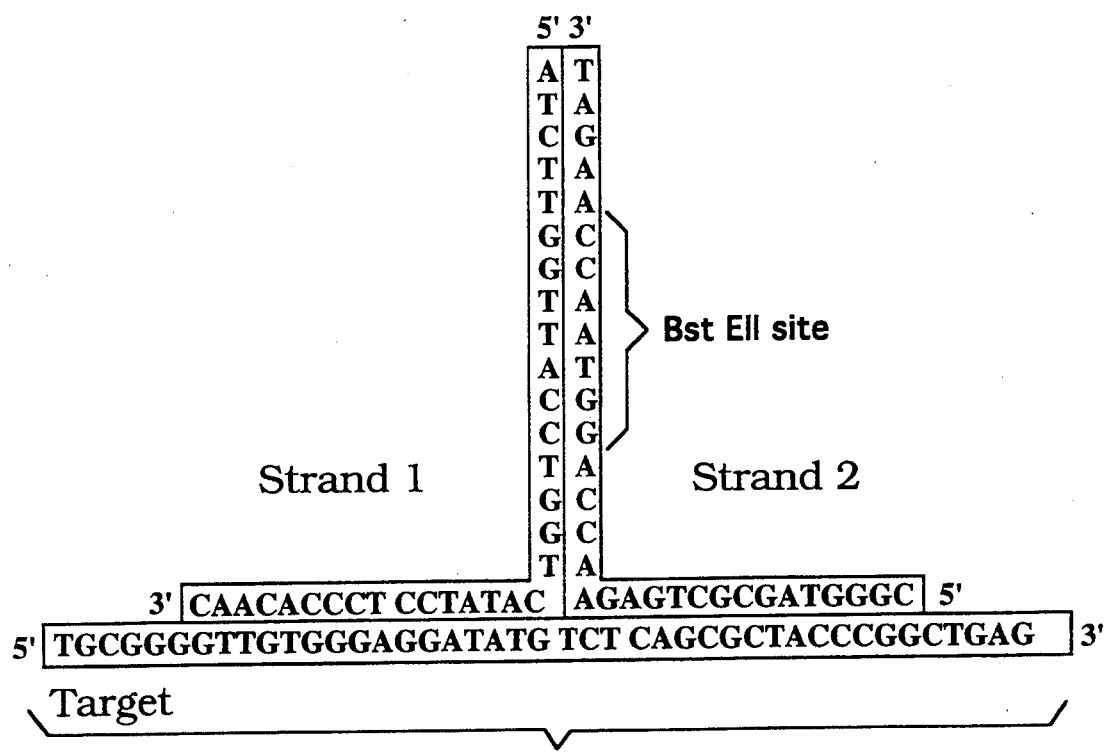
FIG. 16 is a specific example of probes detectable by restriction endonuclease treatment.

A specific example of the system shown in FIG. 15A is shown in FIG. 16. This structure is the same as that shown in FIG. 2, except that the AE label is not included. A BstEII restriction endonuclease site is engineered into the arm regions as shown. To analyze cutting of the arm regions ±target nucleic acid, strand 2 of the probe was first labeled with $^{32}P$ using the standard kinasing protocol. Probe was then hybridized with target using the following conditions: Hybrid: 0.6 pmol $^{32}P$-labeled strand 2; 15 pmol strand 1; 3 pmol target strand. Control: Same as hybrid, except no target. As a control of enzymatic activity, strand 2 was evaluated-±an exactly complementary DNA target strand. These controls will be referred to as Linear-Hybrid and Linear-Control. The amounts used were the same as above (0.6 pmol $^{32}P$-labeled strand 2;±3 pmol target strand). These annealing reactions were incubated for 60 min at 60° C. in 60 μl of 50 mM Tris buffer, pH 7.9 (at 25° C.), 500 mM NaCl. Aliquots of each annealing reaction were then digested with BstEII under the following conditions: 10 μl of each reaction above diluted to 100 l with the final conditions of 50 mM Tris buffer, pH 7.9 (at 25° C.), 100 mM NaCl, 10 mM $MgCl_2$, 1 mM DTT. The samples were incubated with either 10, 5, 1 or 0.2 units of BstEII (New England Biolabs) for 60 min at 60° C. Aliquots were then analyzed using standard polyacrylamide gel electrophoresis (20% gel, 500 V, 15 mA, 2.5 hours). A standard autoradiogram of the gel was then performed.

Figure 17:
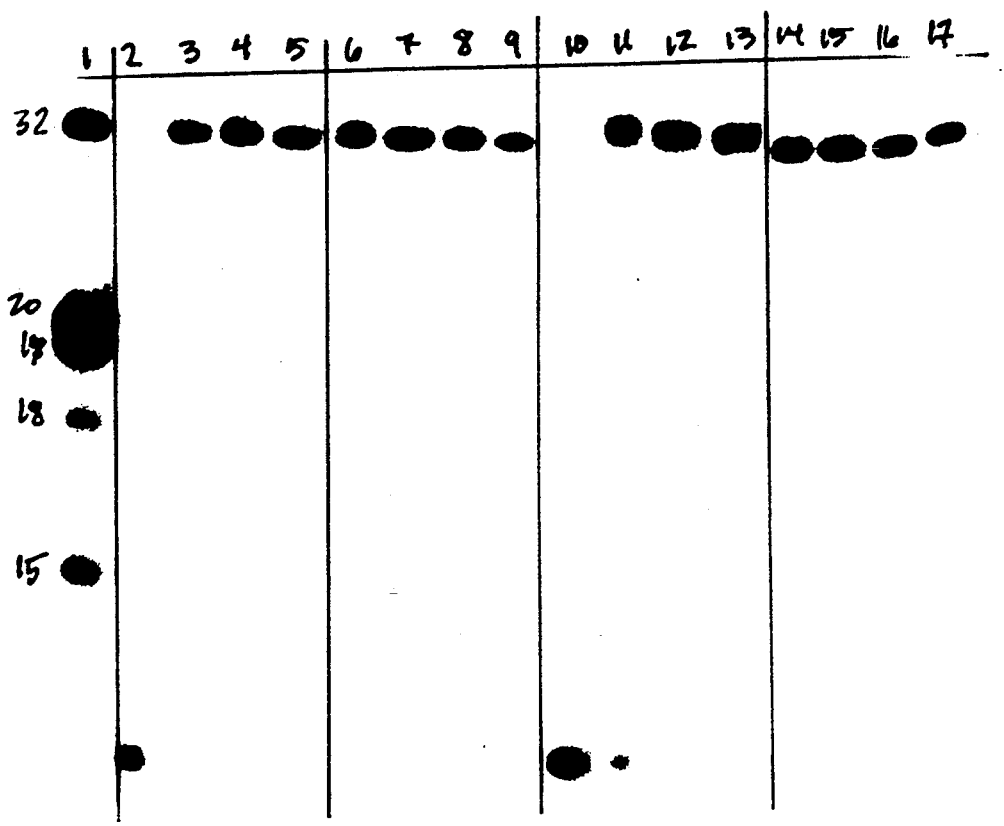
FIG. 17 is an autoradiogram of a test with a probe shown in FIG. 16.

The results are shown in FIG. 17 and demonstrate target-dependent cleavage of the arm region duplex at 10 and 5 units of BstEII. Furthermore, this restriction site can be any one that is desired since the sequence of the arm regions is independent of the target sequence. In this manner, use of a restriction enzyme will not be dependent on finding the correct recognition sequence in the target to be analyzed.

EXAMPLE 14

Figure 15C:
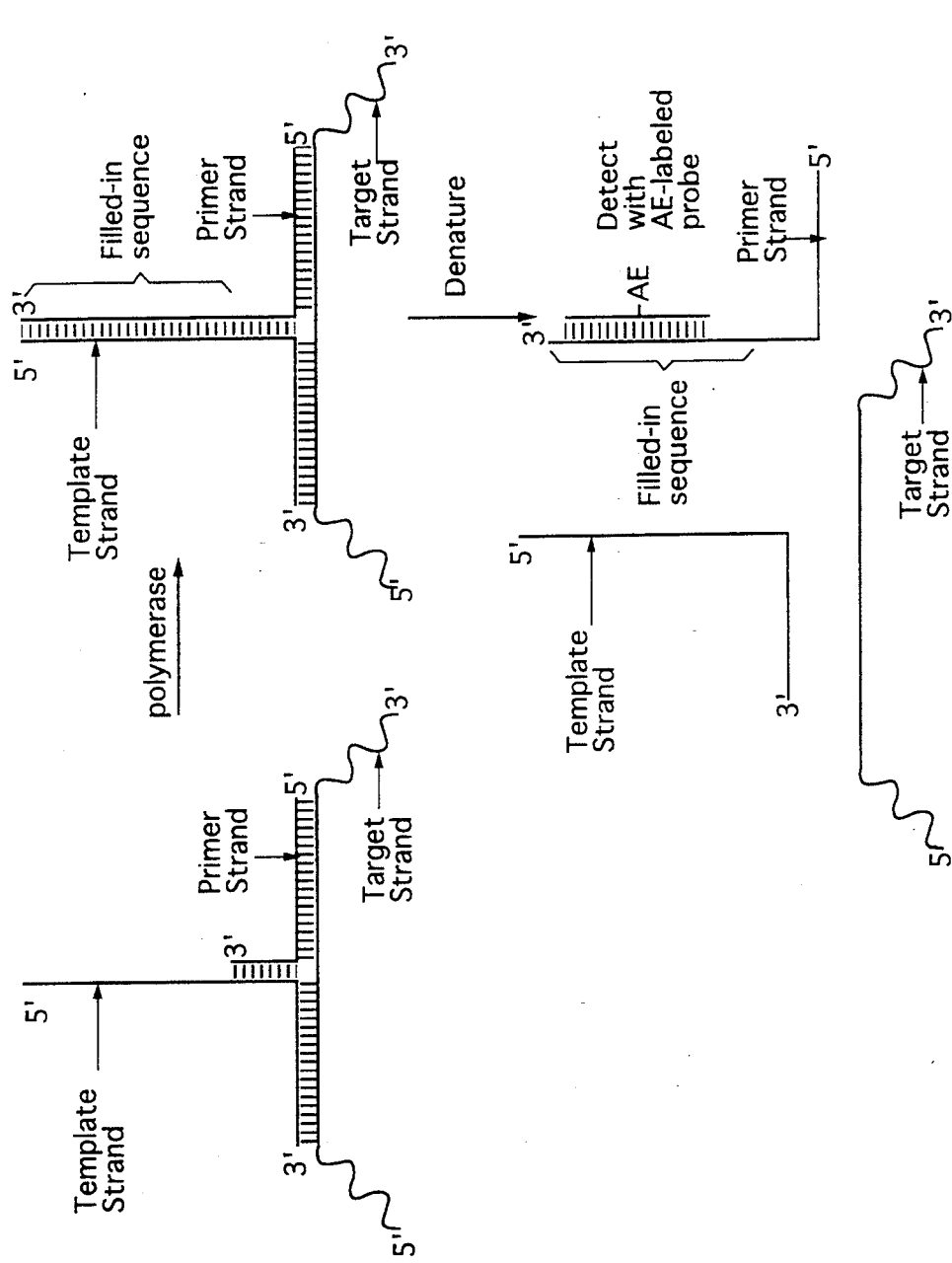
Figure 15D:
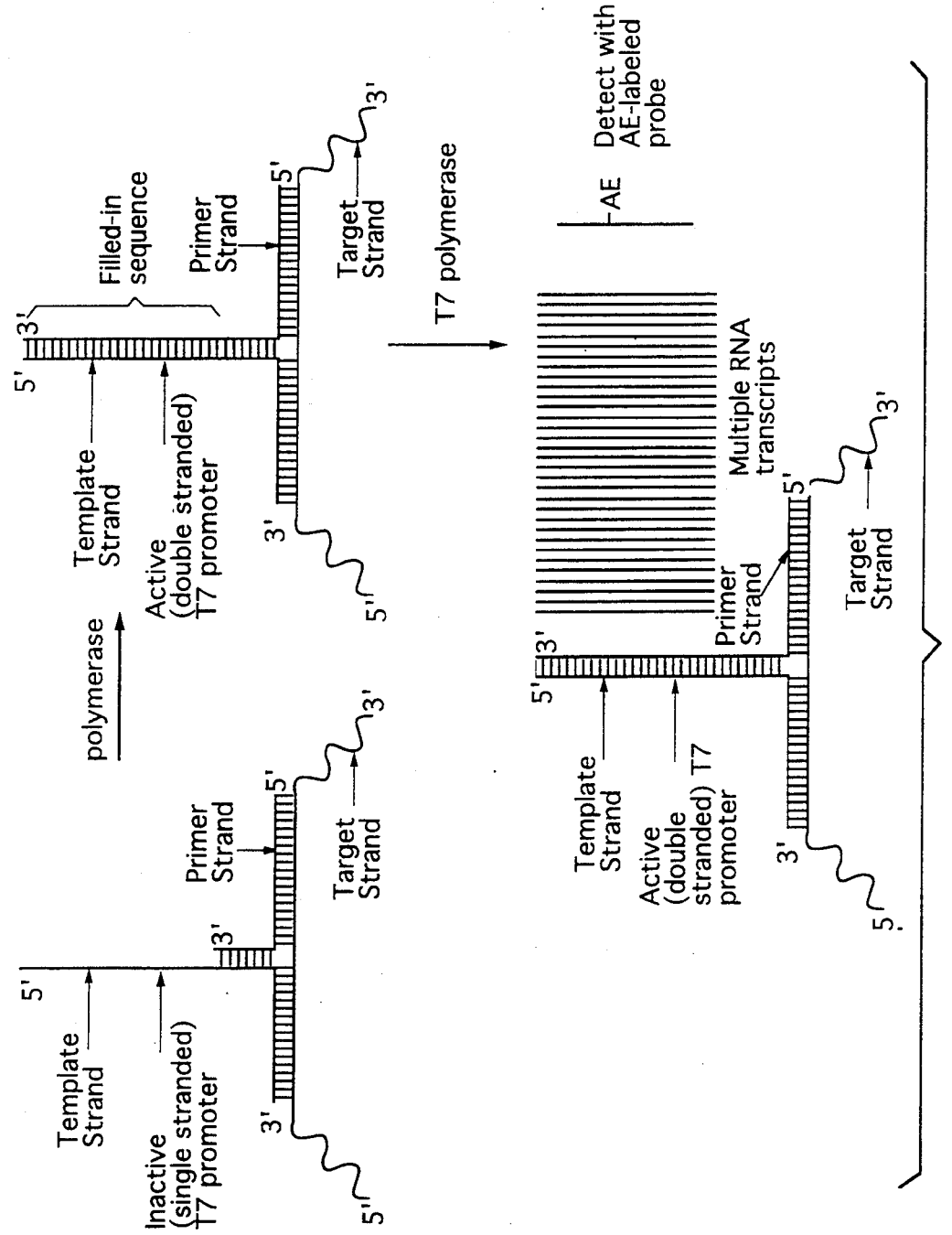
Figure 18:
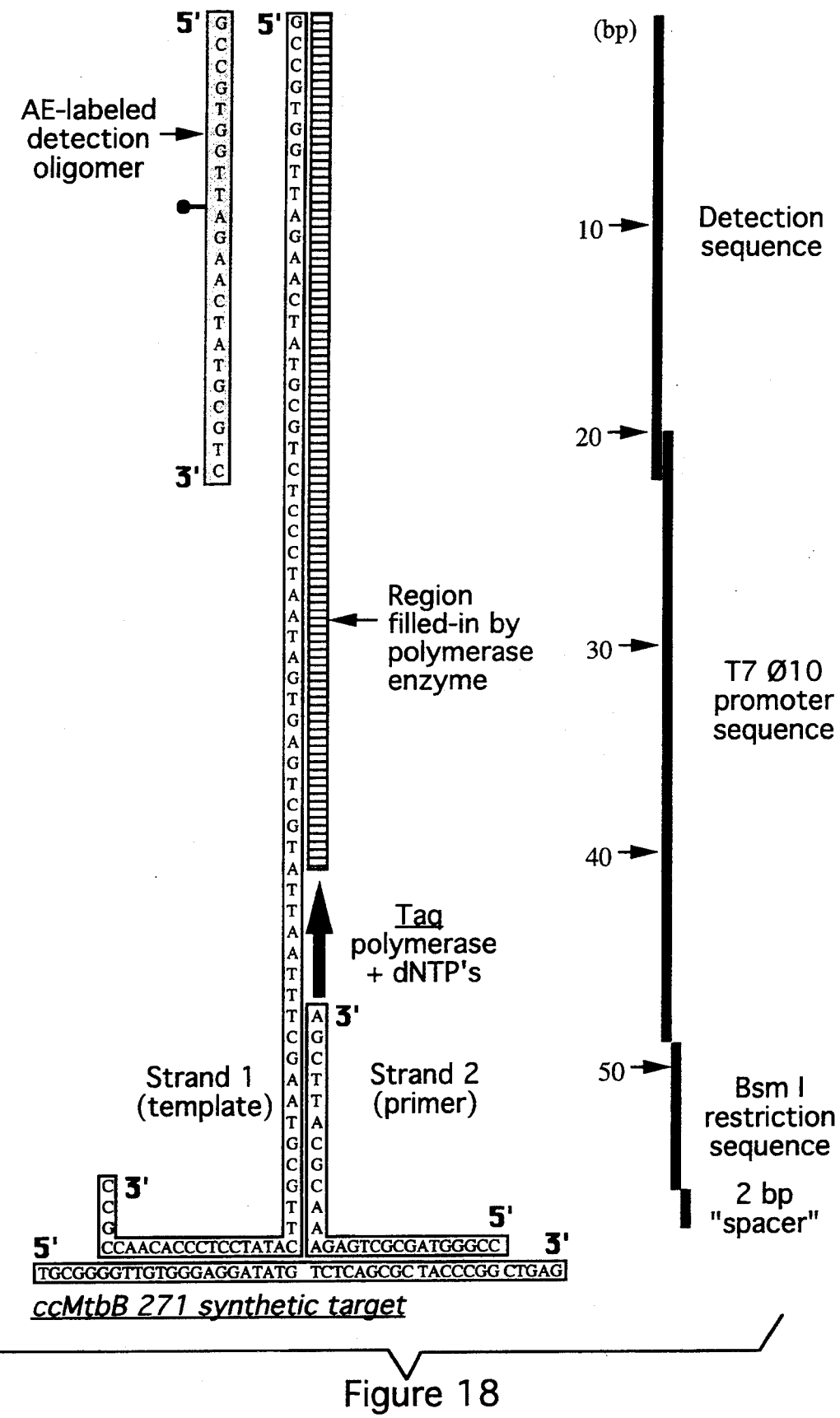
FIG. 18 is a specific example of a probe detectable by enzymatic amplification.

A specific example of systems shown in FIGS. 15B and 15C is shown in FIG. 18. This structure contains a template strand (strand 1) and a primer strand (strand 2). The template strand contains a detection sequence at its 5' end as well as a T7 promoter site 3' of the detection sequence (see FIG. 18). Upon hybridization of both strands to the target, the arm regions form a stable duplex, and the 3' end of strand 2 becomes an active primer extension site for a polymerase enzyme. The enzyme fills-in the complement to the template strand, which can then be denatured and detected using the AE-labeled detection oligomer shown in FIG. 18. Fill-in with the polymerase also creates an active (double-stranded) T7 promoter region with the same detection sequence template region. A T7 RNA polymerase enzyme can then transcribe multiple RNA copies off of the template, which are also detected with the AE-labeled detection oligomer.

The probe was first hybridized with the target strand by incubating 0.3 pmol of strand 1, 0.9 pmol of strand 2 and 0.1 pmol of the target strand in 50 mM Tris buffer, pH 7.9 (@25° C.), 0.5M NaCl (10 µl final volume) at 60° C. for 60 minutes (Control sample contained no target). This sample was then diluted to 50 µl for extension with DNA polymerase under the following conditions: 20 mM Tris buffer, pH 7.9 (at 25° C.), 0.15M NaCl, 3 mM MgSO$_4$, 1% TX-100, 1 mM DTT, 2 mM dATP, 2 mM dTTP, 2 mM dGTP, 2 mM dCTP and 4 units of Taq polymerase (Cetus Corp.). The reaction was incubated at 60° C. for one hour. A 5 µl aliquot of the sample was then mixed with 25 µl of 6% lithium lauryl sulfate, 60 mM sodium phosphate buffer, pH 6.8, 2 mM EDTA and 2 mM EGTA and 20 µl of water. This sample was incubated at 95° C. for 5 minutes, cooled to 60° C. or lower, and then mixed with 50 µl of 200 mM lithium succinate buffer, pH 5.2, 17% lithium lauryl sulfate, 2 mM EDTA, 2 mM EGTA and 0.1 pmol of AE-labeled detection oligomer. This reaction mixture was incubated for 60 minutes at 60° C. Next, 300 µl of 0.15M sodium borate buffer, pH 7.6, containing 5% Triton X-100 detergent was added, and the sample was incubated at 60° C. for 10 minutes. The chemiluminescence was measured in a luminometer (LEADER I, Gen-Probe, CA) by the automatic injection of 200 µl of 1 mM HNO$_3$, 0.1% H$_2$O$_2$, then 200 µl of 1N NaOH, 2% Zwittergent followed by measurement of signal for 2 seconds.

For transcription with T7 polymerase, 5 µl of the extension mixture was added to 45 µl of a transcription mixture such that the final conditions were as follows: 40 mM Tris buffer, pH 7.9 (at 25° C.), 6 mM MgCl$_2$, 2 mM spermidine, 10 mM DTT, 2.5 mM rCTP, 2.5 mM rUTP, 6.5 mM rATP, 6.5 mM rGTP and 400 units of T7 RNA polymerase (United States Biochemical Corporation). A 5 µl aliquot of this sample was assayed using the AE-labeled detection oligomer as described above.

The following results were obtained:

| Activity | AE-probe assay (RLU) | |
|---|---|---|
| | Hybrid | Control |
| Taq polymerase | 74,125 | 1,083 |
| T7 RNA polymerase | 641,753 | 97,218 |

These data demonstrate that sites for Taq polymerase and T7 RNA polymerase can be created separate from the target region, yet the activity of these sites is modulated by hybridization to target.

EXAMPLE 15

A specific example of the general configuration shown in FIG. 6E is shown in FIG. 21. The target strand is a synthetic 38 mer oligomer; the probe strands form a 4-way junction with the target strand as shown. All oligomers were synthesized as described in Example 1 above. Hybridization characteristics of the structures shown in FIGS. 22A-22I (various schematic representations of the structure shown in FIG. 21) were evaluated using DH analysis protocols described in Example 1; all operations were performed at 50° C. The amounts of the different strands used were always the same (even if not all the strands were used) and were as follows: target strand—1.5 pmol; strand 1—0.1 pmol; strand 2—6.5 pmol; strand 3—1.0 pmol. The following results were obtained:

| Structure (Fig. Number) | Hydrolysis Half-life (min.) |
|---|---|
| 22A | 37.0 |
| 22B | 0.54 |
| 22C | 1.7 |
| 22D | 0.72 |
| 22E | 0.69 |
| 22F | 0.60 |
| 22G | 1.7 |
| 22H | 42.7 |
| 22I | 0.55 |

These data demonstrate that the AE is not protected from ester hydrolysis in the absence of target but is protected from ester hydrolysis in the presence of target (and the other probe strands). In this particular example, all four strands must be present to form a stable duplex between the arm regions of probe strands 1 and 2.

Target Independent Probe Amplification

Figure 19A:
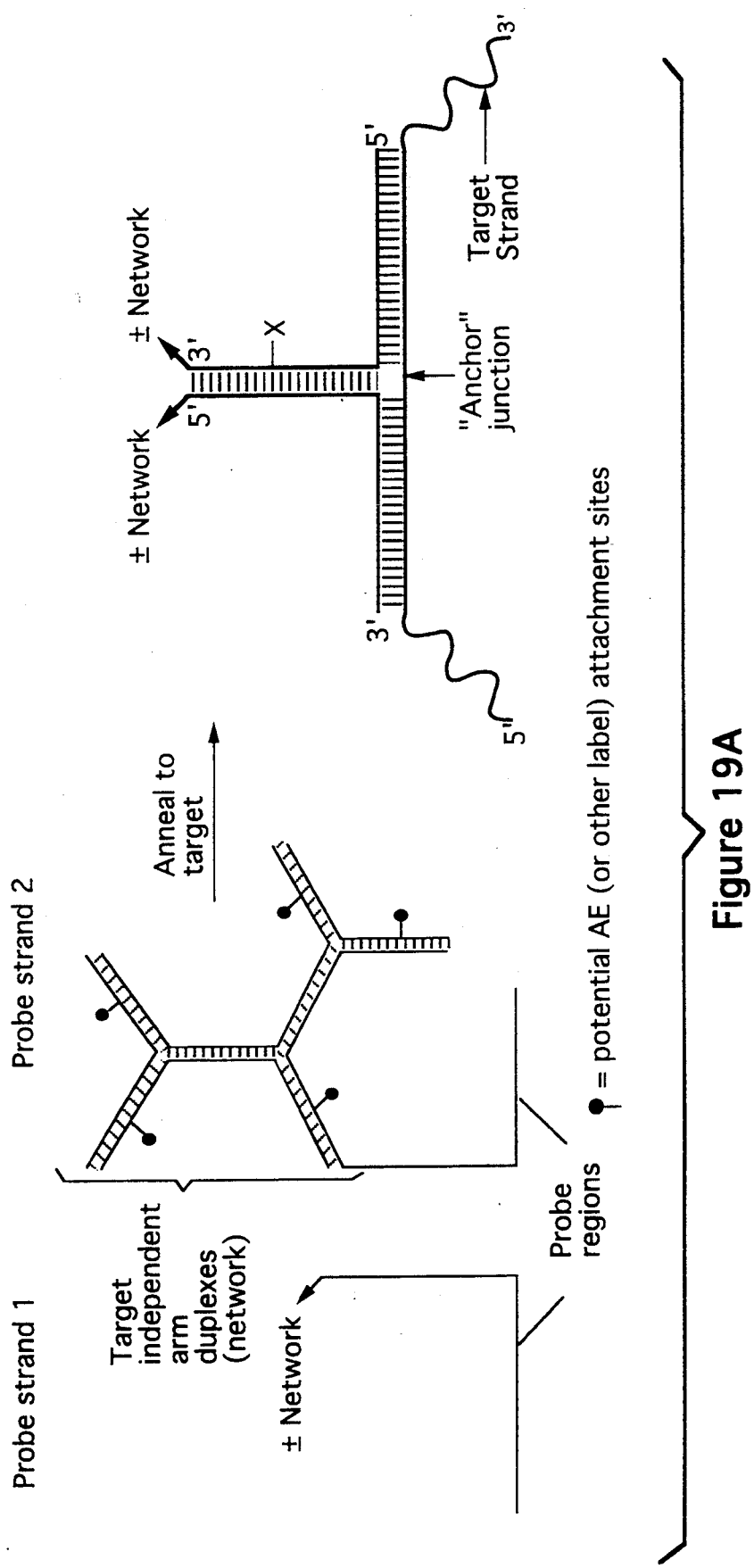
Figure 19B:
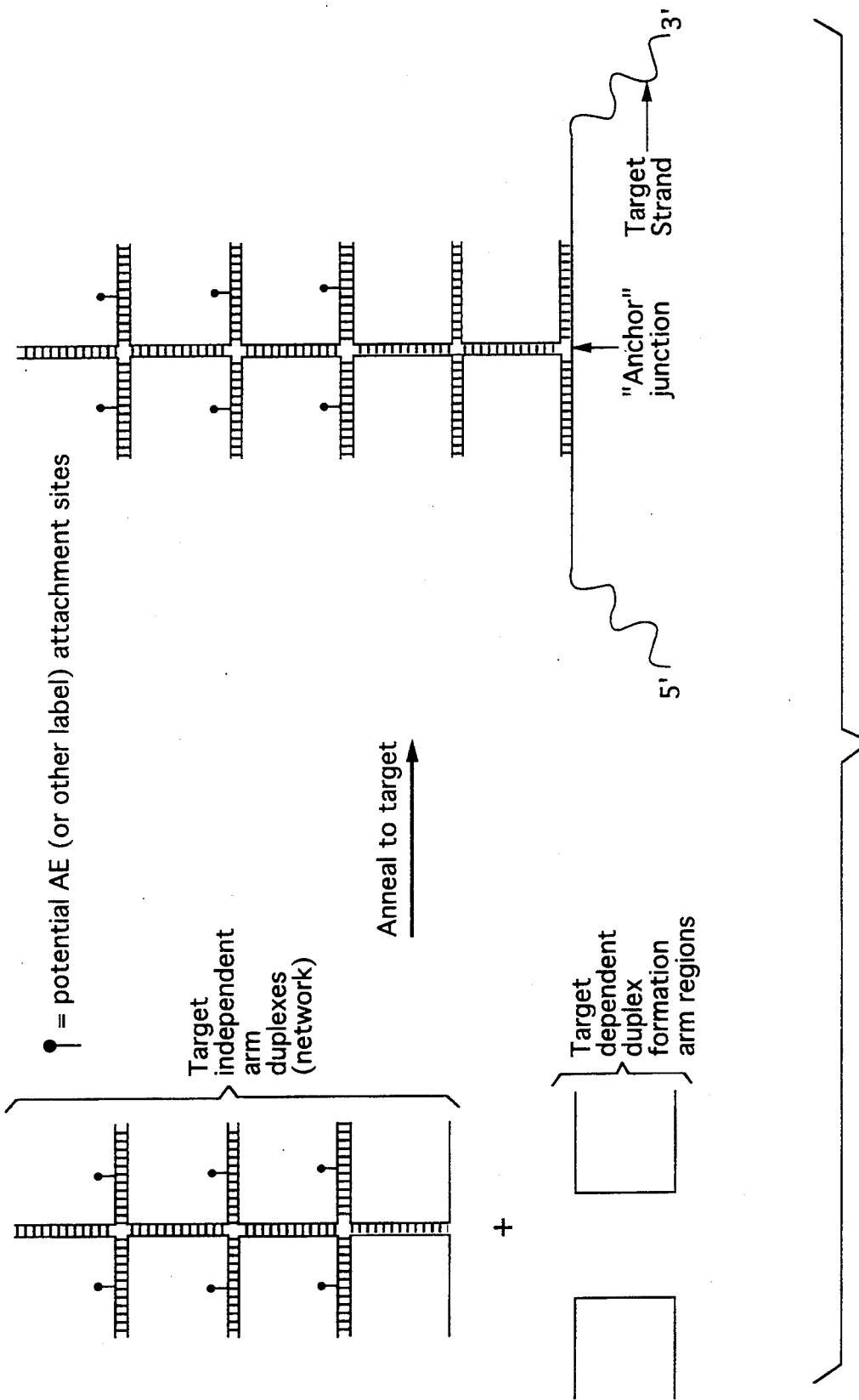

In another configuration, some of the duplexes formed between complementary arm regions are formed independent of target (as long as at least one such duplex is formed only in the presence of target). Some examples of this configuration are shown in FIGS. 19A-19B. One of the utilities of this configuration is label amplification, since AE or another label can be placed in multiple regions of a "network" of branched nucleic acid structures. Furthermore, when AE is the label, this configuration allows for a universal detection complex that could be used for any desired target site. This structure will become associated with the target molecule when the two (or more) probe regions hybridize to target, thus stabilizing the "anchor" junction (as depicted in FIGS. 19A and 19B). The target with this associated label amplification network will then typically have to be separated from unassociated network by some heterogeneous method (e.g., sandwich assay, hydroxyapatite capture of target nucleic acid). The number of junctions formed with target can be unlimited (at least up to 5, or even 10, and depending on the size of the probe, can be several thousands, so long as the hybridized probes do not precipitate from solution), as can the formation of a detection network which may associate with probe before or after hybridization to target.

Figure 20C:
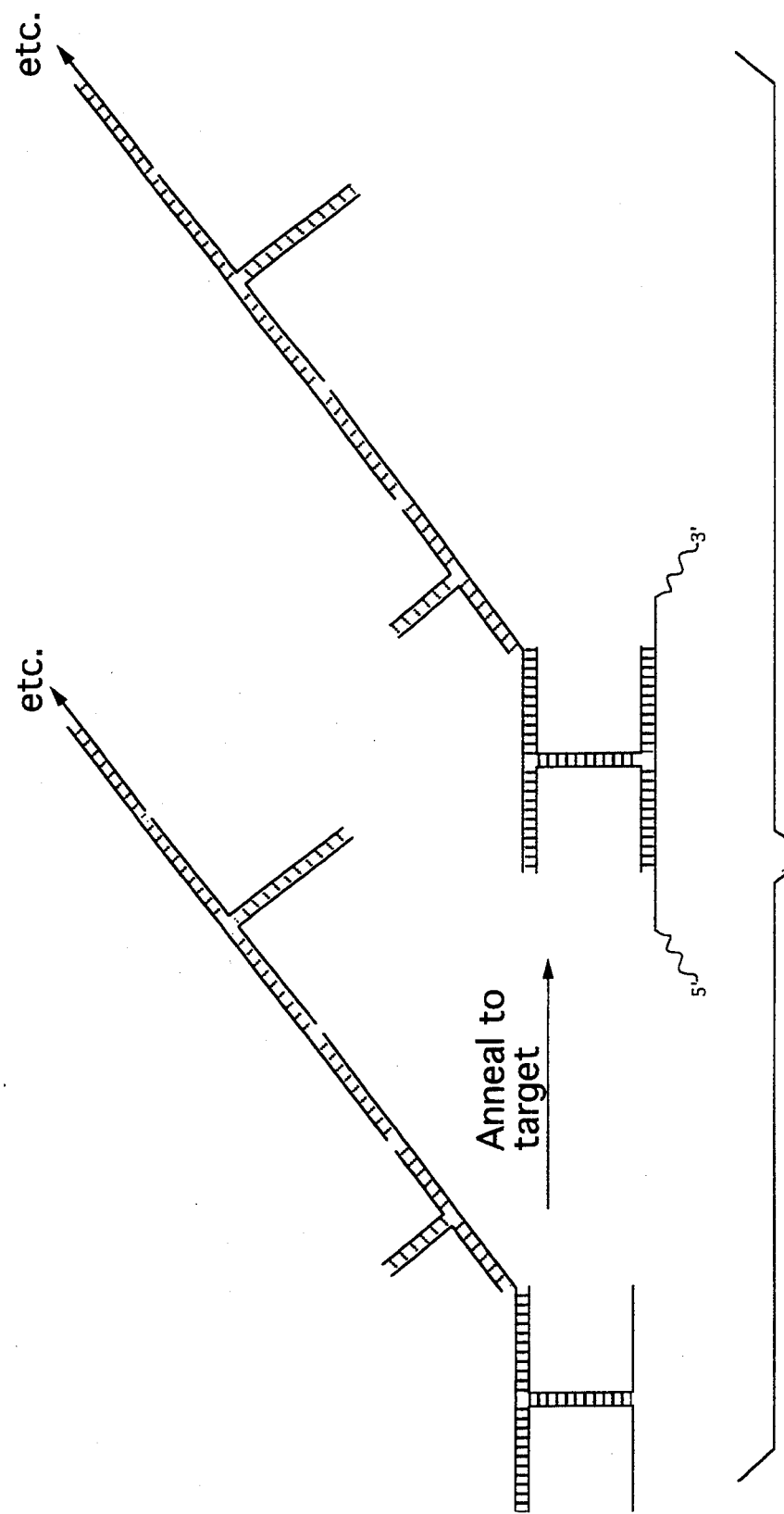

In one case of the configuration discussed above, all the junctions could form in a target-independent manner. Some examples of this configuration are shown in FIGS. 20A–20C. This would allow for label amplification, using the branched nucleic acid structures to create networks, thereby allowing the incorporation of multiple labels per target site. This strategy can be used with a probe that forms a nucleic acid junction with the target strand (this junction is target dependent in the sense that the full junction cannot form in the absence of target, but the duplex formed between associated arm regions is target independent in that they form even in the absence of target), or a probe that does not form a nucleic acid junction with the target strand.

Therapeutic Probes

In addition to the detection and quantitation of nucleic acid targets, the branched nucleic acid probe configurations described herein can also be utilized in a variety of therapeutic applications. For example, the general configuration shown in FIG. 15, system 3, could be utilized by designing the probe regions to be specific for, e.g., an infectious organism, or specific cancer cells, and the arm regions to code for a biologically active molecule. The probes will hybridize with the target site, the template strand filled in by endogenous polymerases (this step might be unnecessary), producing an active coding region which will then generate (again via endogenous activities) a biologically active molecule, such as an inhibitor of an essential transcription or translation factor, a peptide or other small molecule that is toxic to the organism or cell, or an antigen that renders the cell susceptible to removal by the immune system.

Alternatively, the arm regions may form a double-stranded RNA region in a target-dependent manner, which in turn stimulates interferon activity. As another example, the junction formed with a target nucleic acid can be designed to form a site such that (at least) the target strand is cleaved by an endogenous resolvase enzyme. The probe will target a site where this cleavage would be lethal to the organism, or cell.

As another example, the duplex arm regions may create a recognition site for an endogenous nuclease that binds to this recognition site but cleaves at a distal site located on the target strand, with this cleavage leading to death of the organism, or cell. Alternatively, the arm region duplex will create a recognition site that competes for the binding of an essential endogenous regulation protein, or interferes with the assembly of an essential regulation complex in a sequence specific manner. Further, various combinations of probes could be designed to form stable branch points with an essential region of the target nucleic acid, thus blocking binding of sequence specified processing factors and thereby inhibiting replication.

Other embodiments are within the following claims.

---

We claim:

1. A purified nucleic acid probe comprising one or more nucleic acid molecules together comprising at least two separate target regions which hybridize with a target nucleic acid under a predetermined environmental condition comprising a hybridization temperature, and at least two arm regions, wherein said arm regions, under said predetermined environmental condition, do not hybridize with said target nucleic acid, or with each other in the absence of said target nucleic acid, but in the presence of said target nucleic acid do hybridize with each other to form a detectable duplex which does not contain labels interacting to produce a detectable signal.

2. The probe of claim 1 wherein said one or more nucleic acid molecules comprises an intercalating molecule which is susceptible to chemical modification by an acid or a base when said molecule forms part of a single stranded nucleic acid molecule or a double stranded nucleic acid molecule and is not susceptible to such chemical modification when said molecule is present in the other of said single stranded nucleic acid molecule or double stranded nucleic acid molecule.

3. The probe of claim 2 wherein said intercalating agent is an acridinium ester.

4. The probe of claim 1 wherein said at least one of said one or more nucleic acid molecules comprise a target region comprising between eight and thirty complementary bases able to complex with a region of fifty contiguous bases of said target nucleic acid.

5. The probe of claim 1 wherein said at least one of said one or more nucleic acid molecules comprise a target region comprising between eight and one hundred complementary bases able to complex with a region of one thousand contiguous bases of said target nucleic acid.

6. The probe of claim 1 wherein said arm regions form a duplex in the absence of target nucleic acid with a melting temperature 4° C. lower than the hybridization temperature in said predetermined environmental condition.

7. The probe of claim 1 wherein said arm regions form a duplex in the absence of target nucleic acid with a melting temperature at least 7° C. lower than said hybridization temperature in said predetermined environmental condition.

8. The probe of claim 1 wherein said arm regions form a duplex in the-absence of target nucleic acid with a melting temperature at least 10° C. lower than said hybridization temperature in said predetermined environmental condition.

9. The probe of claim 1 wherein said arm regions form a duplex in the presence of target nucleic acid with a melting temperature 4° C. higher than the hybridization temperature in said predetermined environmental condition.

10. The probe of claim 1 wherein said arm regions form a duplex in the presence of target nucleic acid with a melting temperature 7° C. higher than the hybridization temperature in said predetermined environmental condition.

11. The probe of claim 1 wherein said arm regions form a duplex in the presence of target nucleic acid with a melting temperature 10° C. higher than the hybridization temperature in said predetermined environmental condition.

12. The probe of claim 1 wherein only one nucleic acid molecule is provided and said nucleic acid molecule comprises a loop region connecting at least two said arm regions.

13. The probe of claim 1 wherein said one or more nucleic acid molecules consists of two nucleic acid molecules each comprising a target region and an arm region.

14. The probe of claim 1 wherein said one or more nucleic acid molecules consists of three nucleic acid molecules each having at least one arm region and at least two of said nucleic acid molecules comprising a separate target region, wherein said three nucleic acid molecules hybridize with said target nucleic acid to form at least two separate hybridized pairs of arm regions.

15. The probe of claim 1 wherein said one or more nucleic acid molecules consists of four nucleic acid molecules each comprising at least one arm region, and at least two said nucleic acid molecules comprising separate target regions, wherein said four nucleic acid molecules and said target nucleic acid hybridize to form at least three separate duplexes formed between said arm regions.

16. The probe of claim 1, wherein said one or more nucleic acid molecules comprises five nucleic acid molecules each comprising at least one arm region, and at least two said nucleic acid molecules comprising separate target regions, wherein said five nucleic acid molecules and said target nucleic acid hybridize to form at least four separate duplexes between said arm regions.

17. The probe of claim 1, wherein said target regions hybridize with said target nucleic acid, said arm regions hybridize together to form an arm, and a junction is formed at the base of the arm between said two separate target regions,
wherein said one or more nucleic acid molecules or said target nucleic acid may include nucleic acid adjacent said junction which does not form a duplex with said arm regions or said target regions or said target nucleic acid and loops out from said junction, or wherein said target regions include along their length or at the ends distant from said arm regions nucleic acid which does not form a duplex with said target nucleic acid and therefore either loops from a duplex formed between said target nucleic acid and said target region or extends as a single stranded region from the end of said target region, or wherein said arm regions comprise nucleic acid which does not form a duplex with said other arm region and forms a loop extending from said arm region or extends as a single stranded molecule from the end of said arm region distant from said target region.

18. The probe of claim 1 wherein said target regions hybridize with said target nucleic acid and said arm regions hybridize together to form an arm, wherein a junction is formed at the base of the arm between said two separate target regions, wherein one said arm region further comprises a single strand region at the end furthest from a said target region which fails to hybridize to said other arm region and is available for duplex formation with another nucleic acid molecule to form a second arm.

19. The probe of claim 18 wherein both said arm regions comprise a said single stranded region.

20. The probe of claim 19 wherein said one or more nucleic acid molecules includes a nucleic acid molecule able to form a duplex with said single stranded region to form a second or third arm and a second junction between said arms.

21. The probe of claim 1 wherein said at least two arm regions form an arm when hybridized with said target nucleic acid, wherein said arm comprises a biologically or chemically active site.

22. The probe of claim 21 wherein said biologically active site is a restriction endonuclease site.

23. The probe of claim 21 wherein said biologically active site comprises a duplex region and a single stranded region, wherein said duplex region acts as a primer for a DNA polymerase.

24. The probe of claim 21 wherein said biologically active site comprises a promoter for an RNA polymerase.

25. The probe of claim 24 wherein said promoter can be transcribed to form a plurality of RNA transcripts.

26. The probe of claim 21 wherein said biologically active site comprises a DNA/RNA duplex susceptible to cleavage by RNAseH.

27. The probe of claim 21 wherein said chemically active site comprises a chemical active site to cleave adjacent duplex nucleic acid.

28. The probe of claim 27 wherein said chemical comprises Fe.EDTA.

29. The probe of claim 27 wherein said chemical comprises phenanthroline.

30. The probe of claim 1 further comprising other nucleic acid molecules able to hybridize with said arm regions or with single stranded regions extending from said arm regions to form one or more arms.

31. The probe of claim 30 wherein said other nucleic acid molecules are able to hybridize among themselves to form a plurality of arm regions.

32. The probe of claim 1, wherein one of said one or more nucleic acid molecules comprises phosphorothioate.

33. The probe of claim 1, wherein one of said one or more nucleic acid molecules comprises a single stranded nucleic acid region able to form a triple-stranded nucleic acid molecule with one said arm region or said target region hybridized to a complementary nucleic acid molecule.

34. The probe of claim 1, wherein at least one of said one or more nucleic acid molecules does not contain a label which is detectable only in the presence of another label.

35. The probe of claim 1, wherein at least one of said one or more nucleic acid molecules consists of nucleotide bases covalently joined together and one or more radioactive reporter group.

36. The probe of claim 1, wherein at least one of said one or more nucleic acid molecules consists of nucleotide bases covalently joined together.

37. The probe of claim 36, wherein said nucleic acid molecules contain one or more phosphorothioate linkage.

* * * * *

UNITED STATES PATENT AND TRADEMARK OFFICE
CERTIFICATE OF CORRECTION

PATENT NO. : 5,424,413
DATED : June 13, 1995
INVENTOR(S) : Hogan

It is certified that error appears in the above-indentified patent and that said Letters Patent is hereby corrected as shown below:

Column 4, Line 12, the dash between the words "the complimentary" should be omitted;

Column 11, Line 59, in Sample 2 under the column Hybrid "6.1" should read --6.5--;

Column 17, Line 21, the title "Chimetic Probes" should read --Chimeric Probes--;

Column 17, Line 40, the word "Chimetic" should read --Chimeric--;

Column 22, Line 48, the dash after the word "evaluated" should be omitted;

Column 22, Line 49, correct "$\pm$an" by putting a space betweeen "$\pm$" and "an";

Column 22, Line 58, correct "l" to read --ul--;

In column 1, Line 37, correct "use it" to read --use. It--;

UNITED STATES PATENT AND TRADEMARK OFFICE
CERTIFICATE OF CORRECTION

PATENT NO. : 5,424,413
DATED : June 13, 1995
INVENTOR(S) : Hogan

It is certified that error appears in the above-indentified patent and that said Letters Patent is hereby corrected as shown below:

Column 1, line 41, correct "molecule:;) to read --molecules)--.

Signed and Sealed this

Twenty-sixth Day of November 1996

Attest:

BRUCE LEHMAN

*Attesting Officer*     *Commissioner of Patents and Trademarks*